US010583128B2

(12) United States Patent
Collard et al.

(10) Patent No.: US 10,583,128 B2

(45) Date of Patent: Mar. 10, 2020

(54) TREATMENT OF DISEASES RELATED TO ALPHA SUBUNITS OF SODIUM CHANNELS, VOLTAGE-GATED (SCNXA) WITH SMALL MOLECULES

(75) Inventors: Joseph Collard, Delray Beach, FL (US); Olga Khorkova Sherman, Tequesta, FL (US); Jane H. Hsiao, Miami, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 14/343,890

(22) PCT Filed: Aug. 28, 2012

(86) PCT No.: PCT/US2012/052685

§ 371 (c)(1), (2), (4) Date: Mar. 10, 2014

(87) PCT Pub. No.: WO2013/036403

PCT Pub. Date: Mar. 14, 2013

(65) Prior Publication Data

US 2014/0309181 A1 Oct. 16, 2014

Related U.S. Application Data

(60) Provisional application No. 61/531,361, filed on Sep. 6, 2011.

(51) Int. Cl.

| | |
|---|---|
| ***A61K 31/7048*** | (2006.01) |
| ***A61K 31/4545*** | (2006.01) |
| ***A61K 31/496*** | (2006.01) |
| ***A61K 31/58*** | (2006.01) |
| ***A61K 31/495*** | (2006.01) |
| ***A61K 31/5513*** | (2006.01) |
| ***A61K 31/436*** | (2006.01) |
| ***A61K 31/5375*** | (2006.01) |
| ***A61K 31/519*** | (2006.01) |
| ***A61K 31/4985*** | (2006.01) |
| ***A61K 31/4409*** | (2006.01) |
| ***A61K 31/4439*** | (2006.01) |
| ***A61K 31/4422*** | (2006.01) |
| ***A61K 31/365*** | (2006.01) |
| ***A61K 31/64*** | (2006.01) |
| ***A61K 31/41*** | (2006.01) |
| ***A61K 31/135*** | (2006.01) |
| ***A61K 31/165*** | (2006.01) |
| ***A61K 31/4245*** | (2006.01) |

(52) U.S. Cl.

CPC .......... *A61K 31/436* (2013.01); *A61K 31/135* (2013.01); *A61K 31/165* (2013.01); *A61K 31/365* (2013.01); *A61K 31/41* (2013.01); *A61K 31/4245* (2013.01); *A61K 31/4409* (2013.01); *A61K 31/4422* (2013.01); *A61K 31/4439* (2013.01); *A61K 31/4545* (2013.01); *A61K 31/495* (2013.01); *A61K 31/496* (2013.01); *A61K 31/4985* (2013.01); *A61K 31/519* (2013.01); *A61K 31/5375* (2013.01); *A61K 31/5513* (2013.01); *A61K 31/58* (2013.01); *A61K 31/64* (2013.01); *A61K 31/7048* (2013.01); *Y02A 50/401* (2018.01)

(58) Field of Classification Search

CPC .. A61K 31/135; A61K 31/165; A61K 31/365; A61K 31/41; A61K 31/4245; A61K 31/4409; A61K 31/4422; A61K 31/4439; A61K 31/4545; A61K 31/519; A61K 31/5375; A61K 31/5513; A61K 31/58; A61K 31/64; A61K 31/7048; A61K 31/436

USPC .............. 514/27, 176, 221, 237, 237.8, 250, 514/254.05, 254.07, 255.04, 291, 318

See application file for complete search history.

(56) References Cited

U.S. PATENT DOCUMENTS

| | | | |
|---|---|---|---|
| 4,252,951 A * | 2/1981 | Jackson | A61K 31/545 540/220 |
| 4,683,195 A | 7/1987 | Mullis et al. | |
| 4,683,202 A | 7/1987 | Mullis | |
| 4,754,065 A | 6/1988 | Levenson et al. | |
| 4,800,159 A | 1/1989 | Mullis et al. | |
| 5,034,506 A | 7/1991 | Summerton et al. | |
| 5,138,045 A | 8/1992 | Cook et al. | |
| 5,218,105 A | 6/1993 | Cook et al. | |
| 5,288,512 A | 2/1994 | Seiden | |
| 5,288,514 A | 2/1994 | Ellman | |
| 5,319,080 A | 6/1994 | Leumann | |
| 5,393,878 A | 2/1995 | Leumann | |

(Continued)

FOREIGN PATENT DOCUMENTS

| | | |
|---|---|---|
| CA | 2686933 | 4/2008 |
| EP | 335451 A3 | 3/1988 |

(Continued)

OTHER PUBLICATIONS

The Merck Manual, 1992, pp. 1526-1527 and pp. 1488-1490.*
Yamamoto et al, Journal of Neurochemistry, 1997, 68, 1655-1662.*
Catterral et al, Pharmacological Reviews, 2005, 57(4), 397-409.*
Duff et a, l Molecular Pharmacology, 1992, 42(4), 570-74.*
The Merck Manual , 1992, pp. 1488-1490, 1526-1527.*
Scheffer et al, Brain & Development, 2009, 31, 394-400.*
Braga et al, Chem. Comm. 2005, 29, 3635-3645.*
Miyama et al, Pediatric Neurology, 2008, 39(2), 120-122.*

(Continued)

*Primary Examiner* — Ganapathy Krishnan

(74) *Attorney, Agent, or Firm* — CuRNA, Inc.; Monte R. Browder

(57) ABSTRACT

Small compounds that modulate the expression of and/or function of sodium channel, voltage-gated, alpha subunit (SCNxA) are presented. Pharmaceutical compositions containing such small molecules and their use in treating diseases and disorders associated with the expression of SCNxA are also presented.

2 Claims, 1 Drawing Sheet

Specification includes a Sequence Listing.

(56) References Cited

U.S. PATENT DOCUMENTS 5,432,272 A 7/1995 Benner et al.
5,457,189 A 10/1995 Crooke et al.
5,459,255 A 10/1995 Cook et al.
5,474,796 A 12/1995 Brennan
5,491,084 A 2/1996 Chalfie et al.
5,506,337 A 4/1996 Summerton et al.
5,519,134 A 5/1996 Acevedo et al.
5,525,735 A 6/1996 Gallop et al.
5,539,083 A 7/1996 Cook et al.
5,549,974 A 8/1996 Holmes
5,569,588 A 10/1996 Ashby et al.
5,576,302 A 11/1996 Cook et al.
5,593,853 A 1/1997 Chen et al.
5,605,662 A 2/1997 Heller et al.
5,661,134 A 8/1997 Cook et al.
5,708,161 A 1/1998 Reese
5,739,119 A 4/1998 Galli et al.
5,739,311 A 4/1998 Lackey et al.
5,756,710 A 5/1998 Stein et al.
5,849,902 A 12/1998 Arrow et al.
5,891,725 A 4/1999 Soreq et al.
5,902,880 A 5/1999 Thompson
5,908,779 A 6/1999 Carmichael et al.
5,965,721 A 10/1999 Cook et al.
5,972,894 A * 10/1999 Sinackevich .......... A61K 38/05 514/17.8
5,985,663 A 11/1999 Bennett et al.
6,005,095 A 12/1999 Capaccioli et al.
6,013,639 A 1/2000 Peyman et al.
6,013,786 A 1/2000 Chen et al.
6,034,233 A 3/2000 Ecker et al.
6,100,090 A 8/2000 Monia et al.
6,140,492 A 10/2000 Morelli et al.
6,147,200 A 11/2000 Manoharan et al.
6,165,712 A 12/2000 Foulkes et al.
6,165,990 A 12/2000 Singh et al.
6,175,409 B1 1/2001 Nielsen et al.
6,221,587 B1 4/2001 Ecker et al.
6,239,265 B1 5/2001 Cook
6,242,589 B1 6/2001 Cook et al.
6,268,490 B1 7/2001 Imanishi et al.
6,303,374 B1 10/2001 Zhang et al.
6,307,040 B1 10/2001 Cook et al.
6,316,198 B1 11/2001 Skouv et al.
6,335,434 B1 1/2002 Guzaev et al.
6,376,541 B1 4/2002 Nixon et al.
6,403,566 B1 6/2002 Wang
6,444,464 B1 9/2002 Wyatt
6,451,991 B1 9/2002 Martin et al.
6,525,191 B1 2/2003 Ramassamy
6,528,262 B1 3/2003 Gilad et al.
6,528,631 B1 3/2003 Cook et al.
6,617,122 B1 9/2003 Hayden et al.
6,617,442 B1 9/2003 Crooke et al.
6,630,315 B1 10/2003 Miwa et al.
6,639,059 B1 10/2003 Kochkine et al.
6,656,730 B1 12/2003 Manoharan
6,667,337 B2 12/2003 Wilson
6,670,461 B1 12/2003 Wengel et al.
6,710,174 B2 3/2004 Bennett et al.
6,734,291 B2 5/2004 Kochkine et al.
6,762,169 B1 7/2004 Manoharan
6,794,499 B2 9/2004 Wengel et al.
6,833,361 B2 12/2004 Hong et al.
6,861,514 B2 3/2005 Cook et al.
6,867,294 B1 3/2005 Sanghvi et al.
6,936,467 B2 8/2005 Kmiec et al.
6,936,593 B1 8/2005 Agrawal et al.
6,977,295 B2 12/2005 Belotserkovskii et al.
6,986,988 B2 1/2006 Gilad et al.
7,034,133 B2 4/2006 Wengel et al.
7,034,145 B2 4/2006 Shen et al.
7,053,195 B1 5/2006 Goff
7,053,199 B2 5/2006 Imanishi et al.
7,053,207 B2 5/2006 Wengel
7,060,809 B2 6/2006 Wengel et al.
7,084,125 B2 8/2006 Wengel
7,087,589 B2 8/2006 Jacobson et al.
7,125,982 B1 10/2006 Frayne
7,144,995 B2 12/2006 Wise et al.
7,144,999 B2 12/2006 Ward et al.
7,148,204 B2 12/2006 Bennett et al.
7,153,954 B2 12/2006 Koch et al.
7,169,916 B2 1/2007 Krotz et al.
7,199,107 B2 4/2007 Dobie et al.
7,202,357 B2 4/2007 Crooke et al.
7,217,572 B2 5/2007 Ward et al.
7,220,549 B2 5/2007 Buzby
7,226,785 B2 6/2007 Kmiec et al.
7,229,974 B2 6/2007 Peyman et al.
7,229,976 B2 6/2007 Dobie et al.
7,235,534 B2 6/2007 Tanguay et al.
7,235,653 B2 6/2007 Bennett et al.
7,238,858 B2 7/2007 Marraccini et al.
7,276,599 B2 10/2007 Moore et al.
7,285,288 B1 10/2007 Tormo et al.
7,297,786 B2 11/2007 McCray et al.
7,314,923 B2 1/2008 Kaneko et al.
7,320,965 B2 1/2008 Sah et al.
7,321,828 B2 1/2008 Cowsert et al.
7,335,764 B2 2/2008 Crooke et al.
7,335,765 B2 2/2008 Kaneko et al.
7,339,051 B2 3/2008 Crooke et al.
7,371,833 B1 5/2008 Weiss
7,399,845 B2 7/2008 Seth et al.
7,402,434 B2 7/2008 Newman et al.
7,402,574 B2 7/2008 Iversen et al.
7,420,050 B2 9/2008 Park et al.
7,423,142 B2 9/2008 Vornlocher
7,425,545 B2 9/2008 Crooke et al.
7,427,675 B2 9/2008 Capaldi et al.
7,456,154 B2 11/2008 Soreq et al.
7,462,642 B2 12/2008 Wang et al.
7,468,431 B2 12/2008 Bhanot et al.
7,510,830 B2 3/2009 Baguley et al.
7,541,344 B2 6/2009 Bhat et al.
7,547,684 B2 6/2009 Seth et al.
7,569,575 B2 8/2009 Sorensen et al.
7,569,686 B1 8/2009 Bhat et al.
7,572,582 B2 8/2009 Wengel et al.
7,582,745 B2 9/2009 Sah et al.
7,585,893 B2 9/2009 Baguley et al.
7,589,190 B2 9/2009 Westergaard et al.
7,598,227 B2 10/2009 Crooke et al.
7,605,251 B2 10/2009 Tan et al.
7,622,453 B2 11/2009 Frieden et al.
7,662,948 B2 2/2010 Kurreck et al.
7,666,854 B2 2/2010 Seth et al.
7,674,895 B2 3/2010 Reich et al.
7,687,617 B2 3/2010 Thrue et al.
7,691,995 B2 4/2010 Zamore et al.
7,695,902 B2 4/2010 Crooke
7,696,345 B2 4/2010 Allerson et al.
7,709,456 B2 5/2010 Corey et al.
7,709,630 B2 5/2010 Gaarde et al.
7,713,738 B2 5/2010 Hansen et al.
7,718,629 B2 5/2010 Bumcrot et al.
7,723,508 B2 5/2010 Crooke et al.
7,732,422 B2 6/2010 Gleave et al.
7,732,590 B2 6/2010 Bhanot et al.
7,737,264 B2 6/2010 Thrue et al.
7,737,265 B2 6/2010 Akinc et al.
7,741,305 B2 6/2010 Crooke et al.
7,741,309 B2 6/2010 Hansen et al.
7,741,457 B2 6/2010 Seth et al.
7,745,609 B2 6/2010 Bennett et al.
7,749,978 B2 7/2010 Sah et al.
2003/0055036 A1 3/2003 Werner
2003/0139359 A1 7/2003 Dobie
2003/0186920 A1 10/2003 Sirois
2003/0191075 A1 10/2003 Cook et al.
2003/0228618 A1 12/2003 Levanon et al.
2003/0233670 A1 12/2003 Edgerton et al.
2004/0006031 A1 1/2004 Dean et al.

(56) References Cited

U.S. PATENT DOCUMENTS

2004/0033480 A1 2/2004 Wong
2004/0101858 A1 5/2004 Ward et al.
2004/0137423 A1 7/2004 Hayden et al.
2004/0138155 A1 7/2004 Baird et al.
2004/0175803 A1 9/2004 Meritet et al.
2004/0180336 A1 9/2004 Gilad et al.
2004/0254137 A1 12/2004 Ackermann et al.
2005/0009771 A1 1/2005 Levanon et al.
2005/0026160 A1 2/2005 Allerson et al.
2005/0113326 A1 5/2005 Siwkowski et al.
2005/0143357 A1 6/2005 Pousette et al.
2005/0153286 A1 7/2005 Clements
2005/0215504 A1 9/2005 Bennett et al.
2005/0222029 A1 10/2005 Bartel et al.
2006/0009410 A1 1/2006 Crooke et al.
2006/0142196 A1 6/2006 Klein et al.
2006/0178333 A1 8/2006 Soreq et al.
2007/0082848 A1 4/2007 Alitalo et al.
2007/0191462 A1* 8/2007 Hettiarachchi .... A61K 31/4035 514/416
2007/0197459 A1 8/2007 Milner
2007/0213274 A1 9/2007 Salonen
2007/0213292 A1 9/2007 Stoffel et al.
2007/0231816 A1 10/2007 Chaussabel et al.
2007/0248590 A1 10/2007 Milne et al.
2008/0146788 A1 6/2008 Bhat et al.
2008/0171746 A1* 7/2008 Klein .................. A61K 31/519 514/243
2008/0221051 A1 9/2008 Becker et al.
2008/0293142 A1 11/2008 Liu et al.
2009/0163451 A1* 6/2009 Porreca ................. A61K 31/40 514/165
2009/0191263 A1 7/2009 Reich et al.
2009/0192106 A1 7/2009 Dobie et al.
2009/0208479 A1 8/2009 Jaye et al.
2009/0233912 A1* 9/2009 Castile ................ A61K 9/0043 514/220
2009/0258925 A1 10/2009 Wahlestedt
2009/0318536 A1 12/2009 Freier et al.
2009/0326041 A1 12/2009 Bhanot et al.
2010/0105760 A1 4/2010 Collard et al.
2010/0130487 A1* 5/2010 Chafeev ............... C07D 491/10 514/232.8
2010/0323359 A1* 12/2010 MacDonald ......... C12Q 1/6897 435/6.14

FOREIGN PATENT DOCUMENTS

EP 335451 A2 10/1989
WO WO-1984/03564 9/1984
WO WO-1991/19735 12/1991
WO WO-1992/00091 1/1992
WO WO-1992/08796 5/1992
WO WO-1993/20242 10/1993
WO WO-1994-026887 A1 11/1994
WO WO-1994/28143 12/1994
WO WO-1995-015373 A2 6/1995
WO WO-1995/22618 8/1995
WO WO-1995/25116 10/1995
WO WO-1995/35505 12/1995
WO WO-1996-027663 A2 9/1996
WO WO-1997-039120 A1 10/1997
WO WO-1999-014226 A1 3/1999
WO WO-1999-039352 A1 8/1999
WO WO 2000-057837 A1 10/2000
WO WO-2000-061770 A2 10/2000
WO WO-2001-000669 A2 1/2001
WO WO 2001-21631 A2 3/2001
WO WO-2001-025488 A2 4/2001
WO 2001038564 A2 5/2001
WO WO-2001-038564 A2 5/2001
WO WO-2001-051630 A1 7/2001
WO WO 2002-062840 A1 8/2002
WO WO-2002-068688 A1 9/2002
WO WO-2004-016255 A1 2/2004
WO WO-2004-024079 A2 3/2004
WO WO-2004-030750 A1 4/2004
WO WO-2004-041838 A1 5/2004
WO WO-2004-104161 A2 12/2004
WO WO 2005-045034 A2 5/2005
WO WO-2005-070136 A2 8/2005
WO WO-2005-079862 A1 9/2005
WO WO 2007-028065 A2 3/2007
WO WO-2007-071182 A1 6/2007
WO WO-2007-087113 A2 8/2007
WO WO-2007-138023 A1 12/2007
WO WO-2008-057556 A2 5/2008
WO WO-2008-066672 A2 6/2008
WO WO-2008-087561 A2 7/2008
WO WO-2010-002984 A1 1/2010
WO WO-2010-040571 A2 4/2010
WO WO-2010-054364 A1 5/2010
WO WO-2010-058227 A2 5/2010
WO 2011163499 A2 12/2011
WO 2011163499 A3 12/2011

OTHER PUBLICATIONS

Ausubel, Current Protocols in Molecular Biology vol. 1, 1994, 6.0.1-6.4.10.

Barak, et al., "A βArrestin/Green Fluorescent Protein Biosensor for Detecting G Protein-Coupled Receptor Activation," J. Biol. Chem. 272:27497-27500 (1997).

Barber, et al., "Delivery of membrane-impermeant fluorescent probes into living neural cell populations by lipotransfer," Neuroscience Letters 207:17-20 (1996).

Baum, "Solid-phase synthesis of benzodiazepines," C&EN News, Jan. 18, p. 33-34 (1993).

Bernstein, E., et al., "Role for a Bidentate Ribonuclease in the Initiation Step of RNA Interference," Nature 409:363-366 (2001).

Boutla, A., et al., "Short 5'-phosphorylated double-stranded RNAs induce RNA interference in *Drosophila,*" Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biology vol. 30, Taylor and Wang (eds) p. 157-192 (1989).

Bright, et al., "Delivery of Macromolecules into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480:2-16 (2000).

Chabala, J.C., "Solid-phase combinatorial chemistry and novel tagging methods for identifing leads," Curr Opin Biotechnol. 6:632-639 (1995).

Cech J., "Ribozymes and Their Medical Implications," American. Med Assoc. 260:3030-3035 (1988).

Chen, et al., "Expression of ssDNA in Mammalian Cells," BioTechniques 34:167-171 (2003).

(56) References Cited

OTHER PUBLICATIONS

Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleotide resolution," Science 308:5725:1149-1154 (2005).
Cho, et al., "An Unnatural Biopolymer," Science 261:1303-1305 (1993).
Christiensen, N.K. et al., "A Novel Class of Oligonucleotide Analogues Containing 2'-O,3'-C-Linked [3.2.0] Bicycloarabinonucleoside Monomers: Synthesis, Thermal Affinity Studies, and Molecular Modeling," J. Am. Chem. Soc., 120:5458-5463 (1998).
Cubitt, et al. , "Understanding, improving and using green fluorescent proteins," Trends in Biochemical Science 20:448-455 (1995).
Curiel, D. T. et al., "Adenovirus Enhancement of Transferrin-Polylysine-Mediated Gene Delivery," PNAS 88:8850-8854 (1991).
Dai et al., "SIRT1 Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Duff, H. J., et al., "Class I and IV Antiarrhythmic Drugs and Cytosolic Calcium Regulate mRNA Encoding the Sodium Channel α Subunit in Rat Cardiac Muscle", Molecular Pharmacology, vol. 42, No. 4, pp. 570-574, (1992).
Dykxhoorn, D., et al., "Determinants of Specific RNA Interference-Mediated Silencing of Human β-Globin Alleles Differing by a Single Nucleotide Polymorphism," PNAS, vol. 103, No, 15, pp. 5953-5958, (2006).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidontimetic and organic synthetic combinatorial libraries," Med Res Rev 15:481-496 (1995).
Espeseth, et al., "A genome wide analysis of ubiquitin ligases in APP processing identifies a novel regulator of BACE1 mRNA levels," Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geeler A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A.: 90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "Fluorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: All approach to nonpeptide, nonoligomeric chemical diversity," Proc. Nat. Acad. Sci. USA 90:6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).

(56) References Cited

OTHER PUBLICATIONS

Kenan, et al., “Exploring molecular diversity with combinatorial shape libraries,” Trends Biochem Sci 19:57-64 (1994).
Kornberg, A., DNA Replication, W.H. Freeman & Co., San Francisco, pp. 75-77, (1980).
Larson, et al., “Rapid DNA Fingerprinting of Pathogens by Flow Cytometry,” Cytometry, 2000, 41:203-208 (2000).
Larsson, et al., “High-Throughput Protein Expression of cDNA Products as a Tool in Functional Genomics,” J. Biotechnology., 80:143-157 (2000).
Lebl, et al., “One-bead-one-structure combinatorial libraries,” Biopolymers 37:177-198 (1995).
LeGal Lasalle el al., “An Adenovirus Vector for Gene Transfer into Neurons and Glia in teh Brain,” Science 259:988-990 (1993).
Letsinger, et al., “Cholesteryl-conjugated oligonucleotides: Synthesis, Properties, and Activity as Inhibitors of Replication of Human Immunodeficiency Virus in Cell Culture,” PNAS 86:6553-6556 (1989).
Li et al., “Control of APP processing and Aβ generation level by BACE1 enzymatic activity and transcription,” Faseb J 20; 285-292 (2006).
Li, et al., J. Neurochem 89 1308-1312 (2004).
Liang, et al., “Parallel Synthesis and Screening of a Solid Phase Carbohydrate Library,” Science 274:1520-1522 (1996).
Luther, “Role of endogenous antisense RNA in cardiac gene regulation,” J. Mol. Med. 83:26-32 (2005).
Madden, et al., “Serial analysis of gene expression: from gene discovery to target identification,” Drug Discov. Today 5:415-425 (2000).
Makalowska I, Lin CF, Makalowski W., “Overlapping genes in vertebrate genomes,” Comput Biol. Chem 29:1:1-12 (2005).
Mannino and Gould-Fogerite, “Liposome Mediated Gene Transfer,” BioTechniques 6:682-690 (1988).
Manoharan et al., “Lipidic Nucleic Acids,” Tetrahedron Lett 36:3651-3654 (1995).
Manoharan, et al., “Chemical Modifications to Improve Uptake and Bioavailability of Antisense Oligonucleotides,” Ann. N.Y. Acad. Scie 660:306-309 (1992).
Manoharan, et al., “Introduction of a Lipophilic Thioether in teh Minor Groove of Nucleic Acids for Antisense Applications,” Bioorg. Med. Chem. Let 3:2765-2770 (1993).
Manoharan, et al., “Cholic Acid-Oligonucleotide Conjugates for Antisense Applications,” Bioorg. Med. Chem. Let 4;1053 (1994).
Manoharan, et al., “Oligonucleotide Conjugates: Alteration of the Pharmacokinetic Properties of Antisense Agents,” Nucleosides & Nucleotides 14:969-973 (1995).
Manoharan, M., “2'-Carbohydrate modifications in antisense oligonucleotide therapy: importance of conformation, configurationj and conjugation,” Biochemica et Biophysica Acta 1489:117-139 (1999).
Mattick, J. S. “RNA regulation: a new genetics?” Nat. Rev. Genet 5:4:316-323 (2004).
Maurer, R. A., “Cationic Liposome-Mediated Transfection of Primary Cultures of Rat Pituitary Cells,” Bethesda Res. Lab. Focus 11:2:25 (1989).
McNeil in Methods in Cell Biology vol. 29, Taylor and Wang (eds.) p. 153-173 (1989).
Morelli et al., “The antisense bel-2-IgH transcript is an optimal target for synthetic oligonucleotides,” PNAS USA 94:8150-8155 (1997).
Moussaoui, S., et al., “The Antioxidant Ebselen Prevents Neurotoxicity and Clinical Symptoms in a Primate Model of Parkinson’s Diseasr” , Experimental Neurology, vol. 166, No. 2, pp. 235-245, (2000).
Nielsen, et al., “Sequence-Selective Recognition of DNA by Strand Displacement with a Thymine-Substituted Polyamide,” Science 254:1497-1500 (1991).
Oberhauser, et al., “Effective incorporation of 2'-O-methyl-oligoribonucleotides into liposomes and enhanced cell association through modification with thiocholesterol,” Nucl. Acids Res. 20:533-538 (1992).
Petit et al., “Wild-type PINK1 Prevents Basal and Induced Neuronal Apoptosis, a Protective Effect Abrogated by Parkinson Disease-Related Mutations”, Journ. Biol. (Chem., vol. 280, No. 40, pp. 34025-334032 (2005).
Prasanth, et al., “Regulating Gene Expression through RNA Nuclear Retention,” Cell 123, 249-263 (2005).
Prashar & Weissman, “READS: A Method for Display of 3'-End Fragments of Restriction Enzyme-Digested cDNAs for Analysis of Differential Gene Expression,” Methods Enzymol., 303:258-272 (1999).
Quantin, et al., “Adenovirus as an expression vector in muscle cells in vivo,” PNAS 89:2581-2584 (1991).
Rosenfeld, et al., “In Vivo Transfer of the Human Cystic Fibrosis Transmembrane Conductance Regulator Gene to the Airway Epithelium,” Cell, 68:143-155 (1992).
Rosok and Sioud, “Systematic identification of sense-antisense transcripts in mammalian cells,” Nature Biotech. 22(1):104-108 (2004).
Saison-Behmoaras, et al., “Short modified antisense oligonucleotides directed against Ha-ras point mutation induce selective cleavage of the mRNA and inhibit T24 cells proliferation,” EMBO J. 10:1111-1118 (1991).
Sanghvi, V.S., in Crooke, S.T. and LeBleu, B., eds., Antisense Research and Applications, CRC Press, Boca Raton, 1993, p. 276-278.
Scheele et al., “The Human PINK1 Locus is Regulated and Vivo by a Non-Coding Natural Araisense RNA During Modulation of Mitochondrial Function”, BMC Genomics, vol. 8, No. 1, p. 74 (2007).
Schena, et al., “Parallel human genome analysis: Microarray-based expression monitoring of 1000 genes,” PNAS 93:10614-10619(1996).
Shea, et al., “Synthesis, hybridization properties and antiviral activity of lipid-oligodeoxynucleotide conjugates,” Nucl. Acids Res 18:3777-3783 (1990).
Shen, T., et al., “Modification of Globin Gene Expression by RNA Targeting Strategies,” Experimental Hematology, vol. 35, No. 8, pp. 1209-1218, (2007).
Shimomura, et al., “Semi-synthenc aequorin,” J. of Biochemistry (Tokyo) 251:405-410 (1988).
Singer, et al., “Targeting BACE1 with siRNAs ameliorates Alzheimer disease neuropathology in a transgenic model,” Nat Neurosci 8:1343-1349 (2005).
Southwick, et al., “Cyanine Dye Labeling Reagents-Carboxymethylindocyanine Succinimidyl Esters,” Cytometry 11:418-430 (1990).
Stratford-Perricadet, et al., “Widespread Long-term Gene Transfer to Mouse Skeletal Muscles and Heart,” J. Clin. Invest., 90:626-630 (1992).
Sullenger, et al., “Overexpression of TAR sequences Renders Cells Resistant to Human Immunodeficiency Virus Replication,” Cell63:601-608 (1990).
Sun, et al., “Downregulation of Sirt1 by antisense oligonucleotides induces apoptosis and enhances radiations sensitization in A549 lung cancer cells,” Lung Cancer 58(1):21-29 (2007).
Sutcliffe, et al., “TOGA: An automated parsing technology for analyzing expression of nearly all genes,” PNAS, 97:1976-1981 (2000).
Sutton, et al., “TIGR Assembler: A New Tool for Assembling Large Shotgun Sequencing Projects,” Genome Science & Tech., 1:9-19 (1995).
Svinarchuk, et al., “Inhibition of HIV proliferation in MT-4 cells by antisense oligonucleotide conjugated to lipophilic groups,” Biochimie 75:49-54 (1993).
Tamagno, et al., “The various aggregation states β-amyloid 1-42 mediate different effects on oxidative stress, neurodegeneration, and BACE-1 expression,” Free Radic Biol Med 41:202-212 (2006).
Thakker, D.R., et al., “siRNA-mediated knockdown of the serotonin transporter in the adult mouse brain,” Mol Psychiatry 10:782-789 (2005).
Thakker, et al., “Neurochemical and behavioral consequences of widespread gene knockdown in the adult mouse brain by using nonviral RNA interference,” PNAS 101:17270-17275 (2004).

(56) References Cited

OTHER PUBLICATIONS

Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al., "The role of cell-derived oligomers of Aβ in Alzheimer's disease and avenues for therapeutic intervention," Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Ward, J. W., "Pinacidil Monotherapy for Hypertension", Br. J. Clin. Pharmac., vol. 18, No. 2, pp. 223-225, (1984).
Wiesenhofer, et al., "Glial cell line-derived neurotrophic factor (GDNP) is a proliferation factor for rat C6 glioma cells; evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Antisense (NOS3AS) Gene Encodes an Autophagy-Related Protein (APG9-like2) Highly Expressed in Trophoblast", The Journal of Biological Chemistry, vol. 280, No. 18, pp. 18283-18290 (2005).
Yamamoto, et al., "Up-Regulation of Sodium Channel Subunit mRNAs and Their Cell Surface Expression by Antiepileptic Valproic Acid: Activation of Calcium Channel and Catecholamine Secretion in Adrenal Chromaffin Cells", J. Neurochem., vol. 68, No. 4, pp. 1655-1662, (1997).
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; 1-10 (2012).
EP Application No. 06850393.7 Examination Report dated Oct. 18, 2011.
International Search Report and Written Opinion for PCT Application No. PCT/US2010/033078 dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
PCT/US96/10287 (WO97/000271) The Regents of the University of California Jan. 3, 1997.
International Search Report corresponding to PCT/US2012/052685 dated Aug. 28, 2012.
Takahashi, H., et al., "Effectiveness of Topiramate in Eleven Patients with Dravet Syndrome", No to Hattatsu, vol. 42, No. 4, pp. 273-276, (2010). Abstract.
Yakuri, R., "The Effect of Benidipine Hydrochloride on Essential Hypertension", Jpn J Clin Pharmacol Ther, vol. 31, No. 2, pp. 375-376, (2000), Abstract.
Ward, J.W., "Pinacidil Monotherapy for Hypertension", Br. J. Clin. Pharmac., vol. 18, pp. 223-225, (1984).
Moussaoui, S., et al., "The Antioxidant Ebselen Prevents Neurotoxicity and Clinical Symptoms in a Primate Model of Parkinson's Disease", Experimental Neurology, vol. 166, No. 2, pp. 235-245, (2000).
Ploughman, PhD, M., et al., "Brain-Derived Neurotrophic Factor Contributes to Recovery of Skilled Reaching After Focal Ischemia in Rats", Stroke Journal of the American Heart Association, vol. 40, pp. 1490-1495, (2009).
Chan, J. H.P., et al., "Antisense Oligonucleotides: From Design to Therapeutic Application", Clinical and Experimental Pharmacology and Physiology, vol. 33, pp. 533-540, (2006).
Kandimalla, E. R., et al,. "Design, Biochemical, Biophysical and Biological Properties of Cooperative Antisense Oligonuleotides", Nucleic Acids Research, vol. 23, No. 17, pp. 3578-3584, (1995).
Fujiwara, T., "Clinical Spectrum of Mutations in SCN1A Gene: Severe Myoclonic Epilepsy in Infancy and Related Epilepsies", Epilepsy Research, vol. 70s, pp. 223-230, (2006).
Scheffer, I. E., et al., "Dravet Syndrome or Genetic (Generalized) Epilepsy with Febrile Seizures Plus?", Brain & Development, vol. 31, pp. 394-400, (2009).
Bender, A. C., et al., "Cognitive Deficits Associated with Nav1.1 Alterations: Involvement of Neuronal Firing Dynamics and Oscillations", PLOS One, vol. 11, No. 3, pp. e0151538, (2016).
Lal, D., et al., "Evaluation of Presumably Disease Causing SCN1A Variants in a Cohort of Common Epilepsy Syndromes", PLOS One, vol. 11, No. 3, e0150426, (2016).
Fry, A. E., et al., "Pathogenic Copy Number Variants and SCN1A Mutations in Patients with Intellectual Disability and Childhood-Onset Epilepsy", BMC Medical Genetics, No. 17, vol. 34, DOI 10.1186/s12881-016-0294-2, pp. 1-9, (2016).
Long, Y-S, et al., "Identification of the Promoter Region and the 5'-untranslated Exons of the Human Voltage-Gated Sodium Channel Nav1.1 Gene (SCN1A) and Enhancement of Gene Expression by the 5'-untranslated Exons", Journal of Neuroscience Research, vol. 86, Issue 15, pp, 3375-3381, (2008).
Akiyama, M., et al., "Dravet Syndrome:A Genetic Epileptic Disorder", Acta Medica Okayama, vol. 66, No. 5, pp. 369-376, (2012).
Parihar, R. et al., "The SCN1A Gene Variants and Epileptic Encephalopathies", Journal of Human Genetics, vol. 58, pp. 573-580, (2013).
Saitoh, M., et al., "Missense Mutations in Sodium Channel SCN1A and SCN2A Predispose Children to Encephalopathy with Severe Febrile Seizures", Epilepsy Research, vol. 117, pp. 1-6, (2015).
Aiba, I., et al., "Spreading Depolarization in the Brainstem Mediates Sudden Cardiorespiratory Arrest in Mouse SUDEP Models", Science Translational Medicine, vol. 7, No. 282, pp. 282ra46, (2015).
Schuele, S.U., "Effects of Seizures on Cardiac Function", Journal of Clinical Neurophysiology, vol. 26, No. 5, pp. 302-308, (2009).
Chiron, C., "Current Therapeutic Procedures in Dravet Syndrome" Developmental Medicine & Child Neurology, vol. 53, No. 2, pp. 16-18, (2011).
Depienne C., et al., "Parental Mosaicism Can Cause Recurrent Transmission of SCN1A Mutations Associated With Severe Myoclonic Epilepsy of Infancy", Human Mutation, Online vol. 890, pp. 1-10, (2006).

(56) References Cited

OTHER PUBLICATIONS

Marban, E., et al., "Structure and Function of Voltage-Gated Sodium Channels", Journal of Physiology,vol. 508 , No. 3, pp. 647-657, (1998).
Tabb, J., et al., "Suppression of Sodium: Channel Function in Differentiating C2 Muscle Cells Stably Overexpressirig Rat Androgen Receptors", The Journal of Neuroscience, vol. 14, No. 2, pp. 763-773, (1994).
Tinsley, J., et al., "Daily Treatment with SMTC1100, a Novel Small Molecule Utrophin Upregulator, Dramatically Reduces the Dystrophic Symptoms in the mdx Mouse", PLOS ONE, vol. 6, No. 4, pp. e19189, (2011).
Sun, Y., et al., "A Deleterious Nav1.1 Mutation Selectively Impairs Telencephalic Inhibitory Neurons Derived From Dravet Syndrome Patients", eLife Research Article, DOI: 10.7554, eLife 13073, (2016).
Mathes, S., et al., "The Use of Skin Models in Drug Development", Advanced Drug Delivery Review, vol. 69-70, pp. 81-102, (2014).

* cited by examiner

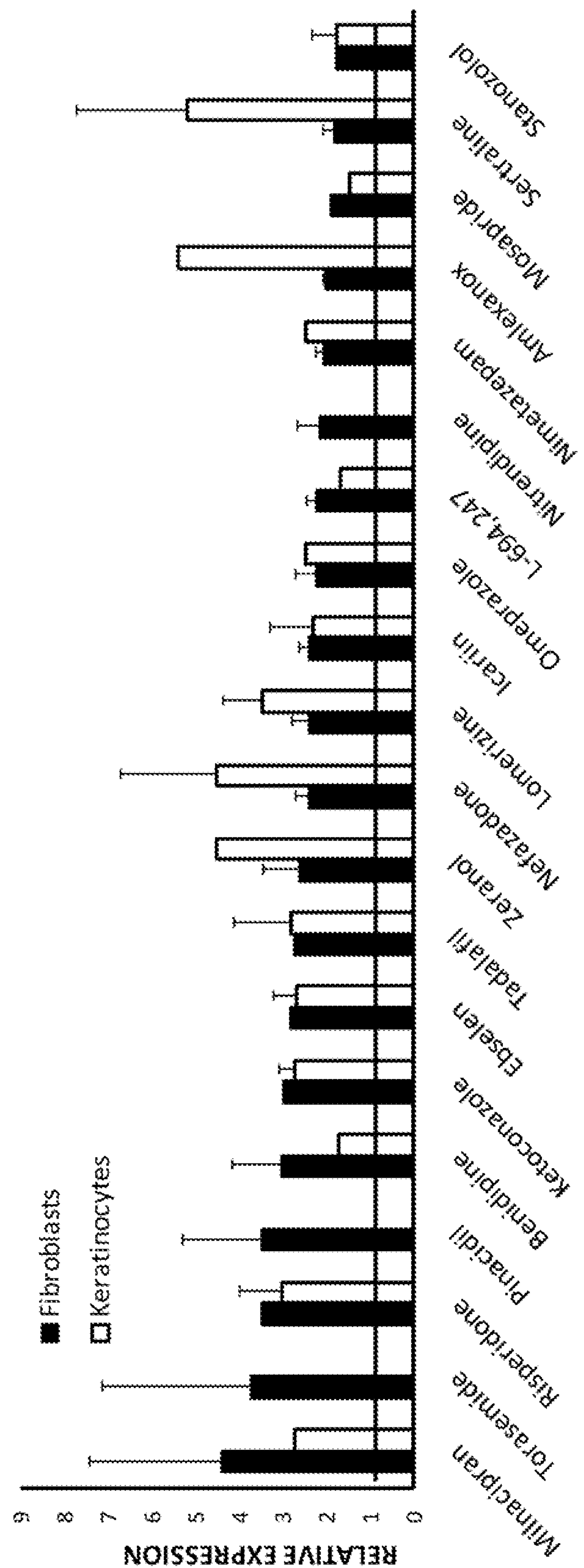
Fibroblasts
Keratinocytes
RELATIVE EXPRESSION
0
1
2
3
4
5
6
7
8
9
Milnacipran
Torasemide
Risperidone
Pinacidil
Benidipine
Ketoconazole
Ebselen
Tadalafil
Zeranol
Nefazadone
Lomerizine
Icariin
Omeprazole
L-694,247
Nitrendipine
Nimetazepam
Amlexanox
Mosapride
Sertraline
Stanozolol

SEQUENCE LISTING

```
<160> NUMBER OF SEQ ID NOS: 11

<210> SEQ ID NO 1
<211> LENGTH: 8133
<212> TYPE: DNA
<213> ORGANISM: Homo sapiens

<400> SEQUENCE: 1

aatgtgcagg atgacaagat ggagcaaaca gtgcttgtac caccaggacc tgacagcttc      60
aacttcttca ccagagaatc tcttgcggct attgaaagac gcattgcaga agaaaaggca     120
aagaatccca aaccagacaa aaaagatgac gacgaaaatg gcccaaagcc aaatagtgac     180
ttggaagctg gaaagaacct tccatttatt tatggagaca ttcctccaga gatggtgtca     240
gagcccctgg aggacctgga cccctactat atcaataaga aaacttttat agtattgaat     300
aaagggaagg ccatcttccg gttcagtgcc acctctgccc tgtacatttt aactcccttc     360
aatcctctta ggaaaatagc tattaagatt ttggtacatt cattattcag catgctaatt     420
atgtgcacta ttttgacaaa ctgtgtgttt atgacaatga gtaaccctcc tgattggaca     480
aagaatgtag aatacacctt cacaggaata tatacttttg aatcacttat aaaaattatt     540
gcaaggggat tctgtttaga agattttact ttccttcggg atccatggaa ctggctcgat     600
ttcactgtca ttacatttgc gtacgtcaca gagtttgtgg acctgggcaa tgtctcggca     660
ttgagaacat tcagagttct ccgagcattg aagacgattt cagtcattcc aggcctgaaa     720
accattgtgg gagccctgat ccagtctgtg aagaagctct cagatgtaat gatcctgact     780
gtgttctgtc tgagcgtatt tgctctaatt gggctgcagc tgttcatggg caacctgagg     840
aataaatgta tacaatggcc tcccaccaat gcttccttgg aggaacatag tatagaaaag     900
```

```
aatataactg tgaattataa tggtacactt ataaatgaaa ctgtctttga gtttgactgg    960
aagtcatata ttcaagattc aagatatcat tatttcctgg agggtttttt agatgcacta   1020
ctatgtggaa atagctctga tgcaggccaa tgtccagagg gatatatgtg tgtgaaagct   1080
ggtagaaatc ccaattatgg ctacacaagc tttgatacct tcagttgggc ttttttgtcc   1140
ttgtttcgac taatgactca ggacttctgg gaaaatcttt atcaactgac attacgtgct   1200
gctgggaaaa cgtacatgat attttttgta ttggtcattt tcttgggctc attctaccta   1260
ataaatttga tcctggctgt ggtggccatg gcctacgagg aacagaatca ggccaccttg   1320
gaagaagcag aacagaaaga ggccgaattt cagcagatga ttgaacagct taaaaagcaa   1380
caggaggcag ctcagcaggc agcaacggca actgcctcag aacattccag agagcccagt   1440
gcagcaggca ggctctcaga cagctcatct gaagcctcta agttgagttc caagagtgct   1500
aaggaaagaa gaaatcggag gaagaaaaga aaacagaaag agcagtctgg tggggaagag   1560
aaagatgagg atgaattcca aaaatctgaa tctgaggaca gcatcaggag gaaaggtttt   1620
cgcttctcca ttgaagggaa ccgattgaca tatgaaaaga ggtactcctc cccacaccag   1680
tctttgttga gcatccgtgg ctccctattt tcaccaaggc gaaatagcag aacaagcctt   1740
ttcagcttta gagggcgagc aaaggatgtg ggatctgaga acgacttcgc agatgatgag   1800
cacagcacct ttgaggataa cgagagccgt agagattcct tgtttgtgcc ccgacgacac   1860
ggagagagac gcaacagcaa cctgagtcag accagtaggt catcccggat gctggcagtg   1920
tttccagcga atgggaagat gcacagcact gtggattgca atggtgtggt ttccttggtt   1980
ggtggacctt cagttcctac atcgcctgtt ggacagcttc tgccagaggt gataatagat   2040
aagccagcta ctgatgacaa tggaacaacc actgaaactg aaatgagaaa gagaaggtca   2100
agttctttcc acgtttccat ggactttcta gaagatcctt cccaaaggca acgagcaatg   2160
agtatagcca gcattctaac aaatacagta gaagaacttg aagaatccag gcagaaatgc   2220
ccaccctgtt ggtataaatt ttccaacata ttcttaatct gggactgttc tccatattgg   2280
ttaaaagtga aacatgttgt caacctggtt gtgatggacc catttgttga cctggccatc   2340
accatctgta ttgtcttaaa tactcttttc atggccatgg agcactatcc aatgacggac   2400
catttcaata atgtgcttac agtaggaaac ttggttttca ctgggatctt tacagcagaa   2460
atgtttctga aaattattgc catggatcct tactattatt tccaagaagg ctggaatatc   2520
tttgacggtt ttattgtgac gcttagcctg gtagaacttg gactcgccaa tgtggaagga   2580
ttatctgttc tccgttcatt tcgattgctg cgagttttca agttggcaaa atcttggcca   2640
acgttaaata tgctaataaa gatcatcggc aattccgtgg gggctctggg aaatttaacc   2700
ctcgtcttgg ccatcatcgt cttcattttt gccgtggtcg gcatgcagct ctttggtaaa   2760
agctacaaag attgtgtctg caagatcgcc agtgattgtc aactcccacg ctggcacatg   2820
aatgacttct tccactcctt cctgattgtg ttccgcgtgc tgtgtgggga gtggatagag   2880
accatgtggg actgtatgga ggttgctggt caagccatgt gccttactgt cttcatgatg   2940
gtcatggtga ttggaaacct agtggtcctg aatctctttc tggccttgct tctgagctca   3000
tttagtgcag acaaccttgc agccactgat gatgataatg aaatgaataa tctccaaatt   3060
gctgtggata ggatgcacaa aggagtagct tatgtgaaaa gaaaaatata tgaatttatt   3120
caacagtcct tcattaggaa acaaaagatt ttagatgaaa ttaaaccact tgatgatcta   3180
aacaacaaga aagacagttg tatgtccaat catacagcag aaattgggaa agatcttgac   3240
```

```
tatcttaaag atgtaaatgg aactacaagt ggtataggaa ctggcagcag tgttgaaaaa   3300
tacattattg atgaaagtga ttacatgtca ttcataaaca accccagtct tactgtgact   3360
gtaccaattg ctgtaggaga atctgacttt gaaaatttaa acacggaaga ctttagtagt   3420
gaatcggatc tggaagaaag caaagagaaa ctgaatgaaa gcagtagctc atcagaaggt   3480
agcactgtgg acatcggcgc acctgtagaa gaacagcccg tagtggaacc tgaagaaact   3540
cttgaaccag aagcttgttt cactgaaggc tgtgtacaaa gattcaagtg ttgtcaaatc   3600
aatgtggaag aaggcagagg aaaacaatgg tggaacctga gaaggacgtg tttccgaata   3660
gttgaacata actggtttga gaccttcatt gttttcatga ttctccttag tagtggtgct   3720
ctggcatttg aagatatata tattgatcag cgaaagacga ttaagacgat gttggaatat   3780
gctgacaagg ttttcactta cattttcatt ctggaaatgc ttctaaaatg ggtggcatat   3840
ggctatcaaa catatttcac caatgcctgg tgttggctgg acttcttaat tgttgatgtt   3900
tcattggtca gtttaacagc aaatgccttg ggttactcag aacttggagc catcaaatct   3960
ctcaggacac taagagctct gagacctcta agagccttat ctcgatttga agggatgagg   4020
gtggttgtga atgccctttt aggagcaatt ccatccatca tgaatgtgct tctggtttgt   4080
cttatattct ggctaatttt cagcatcatg ggcgtaaatt tgtttgctgg caaattctac   4140
cactgtatta acaccacaac tggtgacagg tttgacatcg aagacgtgaa taatcatact   4200
gattgcctaa aactaataga aagaaatgag actgctcgat ggaaaaatgt gaaagtaaac   4260
tttgataatg taggatttgg gtatctctct ttgcttcaag ttgccacatt caaaggatgg   4320
atggatataa tgtatgcagc agttgattcc agaaatgtgg aactccagcc taagtatgaa   4380
gaaagtctgt acatgtatct ttactttgtt attttcatca tctttgggtc cttcttcacc   4440
ttgaacctgt ttattggtgt catcatagat aatttcaacc agcagaaaaa gaagtttgga   4500
ggtcaagaca tctttatgac agaagaacag aagaaatact ataatgcaat gaaaaaatta   4560
ggatcgaaaa aaccgcaaaa gcctatacct cgaccaggaa acaaatttca aggaatggtc   4620
tttgacttcg taaccagaca agtttttgac ataagcatca tgattctcat ctgtcttaac   4680
atggtcacaa tgatggtgga aacagatgac cagagtgaat atgtgactac cattttgtca   4740
cgcatcaatc tggtgttcat tgtgctattt actggagagt gtgtactgaa actcatctct   4800
ctacgccatt attattttac cattggatgg aatatttttg attttgtggt tgtcattctc   4860
tccattgtag gtatgtttct tgccgagctg atagaaaagt atttcgtgtc ccctaccctg   4920
ttccgagtga tccgtcttgc taggattggc cgaatcctac gtctgatcaa aggagcaaag   4980
gggatccgca cgctgctctt tgctttgatg atgtcccttc ctgcgttgtt taacatcggc   5040
ctcctactct tcctagtcat gttcatctac gccatctttg ggatgtccaa ctttgcctat   5100
gttaagaggg aagttgggat cgatgacatg ttcaactttg agacctttgg caacagcatg   5160
atctgcctat tccaaattac aacctctgct ggctgggatg gattgctagc acccattctc   5220
aacagtaagc cacccgactg tgaccctaat aaagttaacc ctggaagctc agttaaggga   5280
gactgtggga acccatctgt tggaattttc tttttgtca gttacatcat catatccttc   5340
ctggttgtgg tgaacatgta catcgcggtc atcctggaga acttcagtgt tgctactgaa   5400
gaaagtgcag agcctctgag tgaggatgac tttgagatgt tctatgaggt ttgggagaag   5460
tttgatcccg atgcaactca gttcatggaa tttgaaaaat tatctcagtt tgcagctgcg   5520
cttgaaccgc ctctcaatct gccacaacca aacaaactcc agctcattgc catggatttg   5580
cccatggtga gtggtgaccg gatccactgt cttgatatct tatttgcttt tacaaagcgg   5640
```

```
gttctaggag agagtggaga gatggatgct ctacgaatac agatggaaga gcgattcatg   5700
gcttccaatc cttccaaggt ctcctatcag ccaatcacta ctactttaaa acgaaaacaa   5760
gaggaagtat ctgctgtcat tattcagcgt gcttacagac gccacctttt aaagcgaact   5820
gtaaaacaag cttcctttac gtacaataaa aacaaaatca aaggtggggc taatcttctt   5880
ataaaagaag acatgataat tgacagaata aatgaaaact ctattacaga aaaaactgat   5940
ctgaccatgt ccactgcagc ttgtccacct tcctatgacc gggtgacaaa gccaattgtg   6000
gaaaaacatg agcaagaagg caaagatgaa aaagccaaag ggaaataaat gaaaataaat   6060
aaaaataatt gggtgacaaa ttgtttacag cctgtgaagg tgatgtattt ttatcaacag   6120
gactccttta ggaggtcaat gccaaactga ctgtttttac acaaatctcc ttaaggtcag   6180
tgcctacaat aagacagtga ccccttgtca gcaaactgtg actctgtgta aaggggagat   6240
gaccttgaca ggaggttact gttctcacta ccagctgaca ctgctgaaga taagatgcac   6300
aatggctagt cagactgtag ggaccagttt caaggggtgc aaacctgtga ttttggggtt   6360
gtttaacatg aaacacttta gtgtagtaat tgtatccact gtttgcattt caactgccac   6420
atttgtcaca tttttatgga atctgttagt ggattcatct ttttgttaat ccatgtgttt   6480
attatatgtg actatttttg taaacgaagt ttctgttgag aaataggcta aggacctcta   6540
taacaggtat gccacctggg gggtatggca accacatggc cctcccagct acacaaagtc   6600
gtggtttgca tgagggcatg ctgcacttag agatcatgca tgagaaaaag tcacaagaaa   6660
aacaaattct taaatttcac catatttctg ggaggggtaa ttgggtgata agtggaggtg   6720
ctttgttgat cttgttttgc gaaatccagc ccctagacca agtagattat ttgtgggtag   6780
gccagtaaat cttagcaggt gcaaacttca ttcaaatgtt tggagtcata aatgttatgt   6840
ttctttttgt tgtattaaaa aaaaaacctg aatagtgaat attgcccctc accctccacc   6900
gccagaagac tgaattgacc aaaattactc tttataaatt tctgcttttt cctgcacttt   6960
gtttagccat cttcggctct cagcaaggtt gacactgtat atgttaatga aatgctattt   7020
attatgtaaa tagtcatttt accctgtggt gcacgtttga gcaaacaaat aatgacctaa   7080
gcacagtatt tattgcatca aatatgtacc acaagaaatg tagagtgcaa gctttacaca   7140
ggtaataaaa tgtattctgt accatttata gatagtttgg atgctatcaa tgcatgttta   7200
tattaccatg ctgctgtatc tggtttctct cactgctcag aatctcattt atgagaaacc   7260
atatgtcagt ggtaaagtca aggaaattgt tcaacagatc tcatttattt aagtcattaa   7320
gcaatagttt gcagcacttt aacagctttt tggttatttt tacattttaa gtggataaca   7380
tatggtatat agccagactg tacagacatg tttaaaaaaa cacactgctt aacctattaa   7440
atatgtgttt agaattttat aagcaaatat aaatactgta aaaagtcact ttattttatt   7500
tttcagcatt atgtacataa atatgaagag gaaattatct tcaggttgat atcacaatca   7560
cttttcttac tttctgtcca tagtactttt tcatgaaaga aatttgctaa ataagacatg   7620
aaaacaagac tgggtagttg tagatttctg ctttttaaat tacatttgct aattttagat   7680
tatttcacaa ttttaaggag caaaataggt tcacgattca tatccaaatt atgctttgca   7740
attggaaaag ggtttaaaat tttatttata tttctggtag tacctgcact aactgaattg   7800
aaggtagtgc ttatgttatt tttgttcttt ttttctgact tcggtttatg ttttcatttc   7860
tttggagtaa tgctgctcta gattgttcta aatagaatgt gggcttcata attttttttt   7920
ccacaaaaac agagtagtca acttatatag tcaattacat caggacattt tgtgtttctt   7980
```

```
acagaagcaa accataggct cctcttttcc ttaaaactac ttagataaac tgtattcgtg   8040

aactgcatgc tggaaaatgc tactattatg ctaaataatg ctaaccaaca tttaaaatgt   8100

gcaaaactaa taaagattac atttttttatt tta                                 8133


<210> SEQ ID NO 2
<211> LENGTH: 8876
<212> TYPE: DNA
<213> ORGANISM: Homo sapiens

<400> SEQUENCE: 2

ggctgcttca gacatatgtc tgtgtgtacg ctgtgaaggt gtttctcttc acagttcccc     60

gccctctagt ggtagttaca ataatgccat tttgtagtcc ctgtacagga aatgcctctt    120

cttacttcag ttaccagaat ccttttacag gaagttaggt gtggtctttg aaggagaatt    180

aaaaaaaaaa aaaaaaaaaa aaaaaaaaga tttttttttt tttaaagcat gatggaattt    240

tagctgcagt cttcttggtg ccagcttatc aatcccaaac tctgggtgta aaagattcta    300

cagggcactt tcttatgcaa ggagctaaac agtgattaaa ggagcaggat gaaaagatgg    360

cacagtcagt gctggtaccg ccaggacctg acagcttccg cttctttacc agggaatccc    420

ttgctgctat tgaacaacgc attgcagaag agaaagctaa gagacccaaa caggaacgca    480

aggatgagga tgatgaaaat ggcccaaagc caaacagtga cttggaagca ggaaaatctc    540

ttccatttat ttatggagac attcctccag agatggtgtc agtgcccctg gaggatctgg    600

acccctacta tatcaataag aaaacgttta tagtattgaa taaagggaaa gcaatctctc    660

gattcagtgc cacccctgcc ctttacattt taactccctt caaccctatt agaaaattag    720

ctattaagat tttggtacat tctttattca atatgctcat tatgtgcacg attcttacca    780

actgtgtatt tatgaccatg agtaaccctc cagactggac aaagaatgtg gagtatacct    840

ttacaggaat ttatactttt gaatcactta ttaaaatact tgcaaggggc ttttgtttag    900

aagatttcac atttttacgg gatccatgga attggttgga tttcacagtc attacttttg    960

catatgtgac agagtttgtg gacctgggca atgtctcagc gttgagaaca ttcagagttc   1020

tccgagcatt gaaaacaatt tcagtcattc caggcctgaa gaccattgtg gggggccctga   1080

tccagtcagt gaagaagctt tctgatgtca tgatcttgac tgtgttctgt ctaagcgtgt   1140

ttgcgctaat aggattgcag ttgttcatgg gcaacctacg aaataaatgt ttgcaatggc   1200

ctccagataa ttcttccttt gaaataaata tcacttcctt ctttaacaat tcattggatg   1260

ggaatggtac tactttcaat aggacagtga gcatatttaa ctgggatgaa tatattgagg   1320

ataaaagtca cttttatttt ttagaggggc aaaatgatgc tctgctttgt ggcaacagct   1380

cagatgcagg ccagtgtcct gaaggataca tctgtgtgaa ggctggtaga aaccccaact   1440

atggctacac gagctttgac acctttagtt gggccttttt gtccttattt cgtctcatga   1500

ctcaagactt ctgggaaaac ctttatcaac tgacactacg tgctgctggg aaaacgtaca   1560

tgatattttt tgtgctggtc attttcttgg gctcattcta tctaataaat ttgatcttgg   1620

ctgtggtggc catggcctat gaggaacaga atcaggccac attggaagag gctgaacaga   1680

aggaagctga atttcagcag atgctcgaac agttgaaaaa gcaacaagaa gaagctcagg   1740

cggcagctgc agccgcatct gctgaatcaa gagacttcag tggtgctggt gggataggag   1800

ttttttcaga gagttcttca gtagcatcta agttgagctc caaaagtgaa aaagagctga   1860

aaaacagaag aaagaaaaag aaacagaaag aacagtctgg agaagaagag aaaaatgaca   1920

gagtccgaaa atcggaatct gaagacagca taagaagaaa aggtttccgt ttttccttgg   1980
```

```
aaggaagtag gctgacatat gaaaagagat tttcttctcc acaccagtcc ttactgagca   2040
tccgtggctc ccttttctct ccaagacgca acagtagggc gagccttttc agcttcagag   2100
gtcgagcaaa ggacattggc tctgagaatg actttgctga tgatgagcac agcacctttg   2160
aggacaatga cagccgaaga gactctctgt tcgtgccgca cagacatgga gaacggcgcc   2220
acagcaatgt cagccaggcc agccgtgcct ccagggtgct ccccatcctg cccatgaatg   2280
ggaagatgca tagcgctgtg gactgcaatg gtgtggtctc cctggtcggg ggcccttcta   2340
ccctcacatc tgctgggcag ctcctaccag agggcacaac tactgaaaca gaaataagaa   2400
agagacggtc cagttcttat catgtttcca tggatttatt ggaagatcct acatcaaggc   2460
aaagagcaat gagtatagcc agtattttga ccaacaccat ggaagaactt gaagaatcca   2520
gacagaaatg cccaccatgc tggtataaat ttgctaatat gtgtttgatt tgggactgtt   2580
gtaaaccatg gttaaaggtg aaacaccttg tcaacctggt tgtaatggac ccatttgttg   2640
acctggccat caccatctgc attgtcttaa atacactctt catggctatg gagcactatc   2700
ccatgacgga gcagttcagc agtgtactgt ctgttggaaa cctggtcttc acagggatct   2760
tcacagcaga aatgtttctc aagataattg ccatggatcc atattattac tttcaagaag   2820
gctggaatat ttttgatggt tttattgtga gccttagttt aatggaactt ggtttggcaa   2880
atgtggaagg attgtcagtt ctccgatcat tccggctgct ccgagttttc aagttggcaa   2940
aatcttggcc aactctaaat atgctaatta agatcattgg caattctgtg ggggctctag   3000
gaaacctcac cttggtattg gccatcatcg tcttcatttt tgctgtggtc ggcatgcagc   3060
tctttggtaa gagctacaaa gaatgtgtct gcaagatttc caatgattgt gaactcccac   3120
gctggcacat gcatgacttt ttccactcct tcctgatcgt gttccgcgtg ctgtgtggag   3180
agtggataga gaccatgtgg gactgtatgg aggtcgctgg ccaaaccatg tgccttactg   3240
tcttcatgat ggtcatggtg attggaaatc tagtggttct gaacctcttc ttggccttgc   3300
ttttgagttc cttcagttct gacaatcttg ctgccactga tgatgataac gaaatgaata   3360
atctccagat tgctgtggga aggatgcaga aaggaatcga ttttgttaaa agaaaaatac   3420
gtgaatttat tcagaaagcc tttgttagga agcagaaagc tttagatgaa attaaaccgc   3480
ttgaagatct aaataataaa aaagacagct gtatttccaa ccataccacc atagaaatag   3540
gcaaagacct caattatctc aaagacggaa atggaactac tagtggcata ggcagcagtg   3600
tagaaaaata tgtcgtggat gaaagtgatt acatgtcatt tataaacaac cctagcctca   3660
ctgtgacagt accaattgct gttggagaat ctgactttga aaatttaaat actgaagaat   3720
tcagcagcga gtcagatatg gaggaaagca aagagaagct aaatgcaact agttcatctg   3780
aaggcagcac ggttgatatt ggagctcccg ccgagggaga acagcctgag gttgaacctg   3840
aggaatccct tgaacctgaa gcctgtttta cagaagactg tgtacggaag ttcaagtgtt   3900
gtcagataag catagaagaa ggcaaaggga aactctggtg gaatttgagg aaaacatgct   3960
ataagatagt ggagcacaat tggttcgaaa ccttcattgt cttcatgatt ctgctgagca   4020
gtggggctct ggcctttgaa gatatataca ttgagcagcg aaaaaccatt aagaccatgt   4080
tagaatatgc tgacaaggtt ttcacttaca tattcattct ggaaatgctg ctaaagtggg   4140
ttgcatatgg ttttcaagtg tattttacca atgcctggtg ctggctagac ttcctgattg   4200
ttgatgtctc actggttagc ttaactgcaa atgccttggg ttactcagaa cttggtgcca   4260
tcaaatccct cagaacacta agagctctga ggccactgag agctttgtcc cggtttgaag   4320
```

```
gaatgagggt tgttgtaaat gctcttttag gagccattcc atctatcatg aatgtacttc   4380
tggtttgtct gatcttttgg ctaatattca gtatcatggg agtgaatctc tttgctggca   4440
agttttacca ttgtattaat tacaccactg gagagatgtt tgatgtaagc gtggtcaaca   4500
actacagtga gtgcaaagct ctcattgaga gcaatcaaac tgccaggtgg aaaaatgtga   4560
aagtaaactt tgataacgta ggacttggat atctgtctct acttcaagta gccacgttta   4620
agggatggat ggatattatg tatgcagctg ttgattcacg aaatgtagaa ttacaaccca   4680
agtatgaaga caacctgtac atgtatcttt attttgtcat ctttattatt tttggttcat   4740
tctttacctt gaatcttttc attggtgtca tcatagataa cttcaaccaa cagaaaaaga   4800
agtttggagg tcaagacatt tttatgacag aagaacagaa gaaatactac aatgcaatga   4860
aaaaactggg ttcaaagaaa ccacaaaaac ccatacctcg acctgctaac aaattccaag   4920
gaatggtctt tgattttgta accaaacaag tctttgatat cagcatcatg atcctcatct   4980
gccttaacat ggtcaccatg atggtggaaa ccgatgacca gagtcaagaa atgacaaaca   5040
ttctgtactg gattaatctg gtgtttattg ttctgttcac tggagaatgt gtgctgaaac   5100
tgatctctct tcgttactac tatttcacta ttggatggaa tatttttgat tttgtggtgg   5160
tcattctctc cattgtagga atgtttctgg ctgaactgat agaaaagtat tttgtgtccc   5220
ctaccctgtt ccgagtgatc cgtcttgcca ggattggccg aatcctacgt ctgatcaaag   5280
gagcaaaggg gatccgcacg ctgctctttg ctttgatgat gtcccttcct gcgttgttta   5340
acatcggcct ccttcttttc ctggtcatgt tcatctacgc catctttggg atgtccaatt   5400
ttgcctatgt taagagggaa gttgggatcg atgacatgtt caactttgag acctttggca   5460
acagcatgat ctgcctgttc caaattacaa cctctgctgg ctgggatgga ttgctagcac   5520
ctattcttaa tagtggacct ccagactgtg accctgacaa agatcaccct ggaagctcag   5580
ttaaaggaga ctgtgggaac ccatctgttg ggattttctt ttttgtcagt tacatcatca   5640
tatccttcct ggttgtggtg aacatgtaca tcgcggtcat cctggagaac ttcagtgttg   5700
ctactgaaga aagtgcagag cctctgagtg aggatgactt tgagatgttc tatgaggttt   5760
gggagaagtt tgatcccgat gcgacccagt ttatagagtt tgccaaactt tctgattttg   5820
cagatgccct ggatcctcct cttctcatag caaaacccaa caaagtccag ctcattgcca   5880
tggatctgcc catggtgagt ggtgaccgga tccactgtct tgacatctta tttgctttta   5940
caaagcgtgt tttgggtgag agtggagaga tggatgccct tcgaatacag atggaagagc   6000
gattcatggc atcaaacccc tccaaagtct cttatgagcc cattacgacc acgttgaaac   6060
gcaaacaaga ggaggtgtct gctattatta tccagagggc ttacagacgc tacctcttga   6120
agcaaaaagt taaaaaggta tcaagtatat acaagaaaga caaaggcaaa gaatgtgatg   6180
gaacacccat caaagaagat actctcattg ataaactgaa tgagaattca actccagaga   6240
aaaccgatat gacgccttcc accacgtctc caccctcgta tgatagtgtg accaaaccag   6300
aaaaagaaaa atttgaaaaa gacaaatcag aaaaggaaga caaagggaaa gatatcaggg   6360
aaagtaaaaa gtaaaaagaa accaagaatt ttccattttg tgatcaattg tttacagccc   6420
gtgatggtga tgtgtttgtg tcaacaggac tcccacagga ggtctatgcc aaactgactg   6480
tttttacaaa tgtatactta aggtcagtgc ctataacaag acagagacct ctggtcagca   6540
aactggaact cagtaaactg gagaaatagt atcgatggga ggtttctatt ttcacaacca   6600
gctgacactg ctgaagagca gaggcgtaat ggctactcag acgataggaa ccaatttaaa   6660
ggggggaggg aagttaaatt tttatgtaaa ttcaacatgt gacacttgat aatagtaatt   6720
```

```
gtcaccagtg tttatgtttt aactgccaca cctgccatat ttttacaaaa cgtgtgctgt   6780
gaatttatca cttttctttt taattcacag gttgtttact attatatgtg actatttttg   6840
taaatgggtt tgtgtttggg gagagggatt aaagggaggg aattctacat ttctctattg   6900
tattgtataa ctggatatat tttaaatgga ggcatgctgc aattctcatt cacacataaa   6960
aaaatcacat cacaaaaggg aagagtttac ttcttgtttc aggatgtttt tagatttttg   7020
aggtgcttaa atagctattc gtatttttaa ggtgtctcat ccagaaaaaa tttaatgtgc   7080
ctgtaaatgt tccatagaat cacaagcatt aaagagttgt tttattttta cataacccat   7140
taaatgtaca tgtatatatg tatatatgta tatgtgcgtg tatatacata tatatgtata   7200
cacacatgca cacacagaga tatacacata ccattacatt gtcattcaca gtcccagcag   7260
catgactatc acatttttga taagtgtcct ttggcataaa ataaaaatat cctatcagtc   7320
ctttctaaga agcctgaatt gaccaaaaaa catccccacc accactttat aaagttgatt   7380
ctgctttatc ctgcagtatt gtttagccat cttctgctct tggtaaggtt gacatagtat   7440
atgtcaattt aaaaaataaa agtctgcttt gtaaatagta attttaccca gtggtgcatg   7500
tttgagcaaa caaaaatgat gatttaagca cactacttat tgcatcaaat atgtaccaca   7560
gtaagtatag tttgcaagct ttcaacaggt aatatgatgt aattggttcc attatagttt   7620
gaagctgtca ctgctgcatg tttatcttgc ctatgctgct gtatcttatt ccttccactg   7680
ttcagaagtc taatatggga agccatatat cagtggtaaa gtgaagcaaa ttgttctacc   7740
aagacctcat tcttcatgtc attaagcaat aggttgcagc aaacaaggaa gagcttcttg   7800
ctttttattc ttccaacctt aattgaacac tcaatgatga aaagcccgac tgtacaaaca   7860
tgttgcaagc tgcttaaatc tgtttaaaat atatggttag agttttctaa gaaaatataa   7920
atactgtaaa aagttcattt tattttattt ttcagccttt tgtacgtaaa atgagaaatt   7980
aaaagtatct tcaggtggat gtcacagtca ctattgttag tttctgttcc tagcactttt   8040
aaattgaagc acttcacaaa ataagaagca aggactagga tgcagtgtag gtttctgctt   8100
ttttattagt actgtaaact tgcacacatt tcaatgtgaa acaaatctca aactgagttc   8160
aatgtttatt tgctttcaat agtaatgcct tatcattgaa agaggcttaa agaaaaaaaa   8220
aatcagctga tactcttggc attgcttgaa tccaatgttt ccacctagtc tttttattca   8280
gtaatcatca gtcttttcca atgtttgttt acacagatag atcttattga cccatatggc   8340
actagaactg tatcagatat aatatgggat cccagctttt tttcctctcc cacaaaacca   8400
ggtagtgaag ttatattacc agttacagca aaatactttg tgtttcacaa gcaacaataa   8460
atgtagattc tttatactga agctattgac ttgtagtgtg ttggtgaaat gcatgcagga   8520
aaatgctgtt accataaaga acggtaaacc acattacaat caagccaaaa gaataaaggt   8580
ttcgcttttg tttttgtatt taattgttgt ctttgtttct atctttgaaa tgccatttaa   8640
aggtagattt ctatcatgta aaaataatct atctgaaaaa caaatgtaaa gaacacacat   8700
taattactat aattcatctt tcaatttttt catggaatgg aagttaatta agaagagtgt   8760
attggataac tactttaata ttggccaaaa agctagatat ggcatcaggt agactagtgg   8820
aaagttacaa aaattaataa aaaattgact aacattttaa aaaaaaaaaa aaaaaa       8876
```

<210> SEQ ID NO 3
<211> LENGTH: 9141
<212> TYPE: DNA
<213> ORGANISM: Homo sapiens

<400> SEQUENCE: 3

```
accatagagt gaatctcaga acaggaagcg gaggcataag cagagaggat tctggaaagg     60
tctctttgtt ttcttatcca cagagaaaga aagaaaaaaa attgtaacta atttgtaaac    120
ctctgtggtc aaaaaaaaaa aaaaaaaaaa aagctgaaca gctgcagagg aagacacgtt    180
ataccctaac catcttggat gctgggcttt gttatgctgt aattcataag gctctgtttt    240
atcagagatt atggagcaag aaaactgaag ccaagccaca tcaaggtttg acagggatga    300
gatacctgtc aaggattcat agtagagtgg cttactggga aaggagcaaa gaatctcttc    360
tagggatatt gtaagaataa atgagataat tcacagaagg gacctggagc ttttccggaa    420
aaaggtgctg tgactatcta aggtaattcg tatgcaagaa gctacacgta attaaatgtg    480
caggatgaaa agatggcaca ggcactgttg gtacccccag gacctgaaag cttccgcctt    540
tttactagag aatctcttgc tgctatcgaa aaacgtgctg cagaagagaa agccaagaag    600
cccaaaaagg aacaagataa tgatgatgag aacaaaccaa agccaaatag tgacttggaa    660
gctggaaaga accttccatt tatttatgga gacattcctc cagagatggt gtcagagccc    720
ctggaggacc tggatcccta ctatatcaat aagaaaactt ttatagtaat gaataaagga    780
aaggcaattt tccgattcag tgccacctct gccttgtata ttttaactcc actaaaccct    840
gttaggaaaa ttgctatcaa gattttggta cattctttat tcagcatgct tatcatgtgc    900
actattttga ccaactgtgt atttatgacc ttgagcaacc ctcctgactg gacaaagaat    960
gtagagtaca cattcactgg aatctatacc tttgagtcac ttataaaaat cttggcaaga   1020
gggttttgct tagaagattt tacgtttctt cgtgatccat ggaactggct ggatttcagt   1080
gtcattgtga tggcatatgt gacagagttt gtggacctgg gcaatgtctc agcgttgaga   1140
acattcagag ttctccgagc actgaaaaca atttcagtca ttccaggttt aaagaccatt   1200
gtgggggccc tgatccagtc ggtaaagaag ctttctgatg tgatgatcct gactgtgttc   1260
tgtctgagcg tgtttgctct cattgggctg cagctgttca tgggcaatct gaggaataaa   1320
tgtttgcagt ggcccccaag cgattctgct tttgaaacca acaccacttc ctactttaat   1380
ggcacaatgg attcaaatgg gacatttgtt aatgtaacaa tgagcacatt taactggaag   1440
gattacattg gagatgacag tcacttttat gttttggatg ggcaaaaaga ccctttactc   1500
tgtggaaatg gctcagatgc aggccagtgt ccagaaggat acatctgtgt gaaggctggt   1560
cgaaacccca actatggcta cacaagcttt gacaccttta gctgggcttt cctgtctcta   1620
tttcgactca tgactcaaga ctactgggaa aatctttacc agttgacatt acgtgctgct   1680
gggaaaacat acatgatatt ttttgtcctg gtcattttct tgggctcatt ttatttggtg   1740
aatttgatcc tggctgtggt ggccatggcc tatgaggagc agaatcaggc caccttggaa   1800
gaagcagaac aaaaagaggc cgaatttcag cagatgctcg aacagcttaa aaagcaacag   1860
gaagaagctc aggcagttgc ggcagcatca gctgcttcaa gagatttcag tggaataggt   1920
gggttaggag agctgttgga aagttcttca gaagcatcaa agttgagttc caaaagtgct   1980
aaagaatgga ggaaccgaag gaagaaaaga agacagagag agcaccttga aggaaacaac   2040
aaaggagaga gagacagctt tcccaaatcc gaatctgaag acagcgtcaa aagaagcagc   2100
ttccttttct ccatggatgg aaacagactg accagtgaca aaaaattctg ctcccctcat   2160
cagtctctct tgagtatccg tggctccctg ttttccccaa gacgcaatag caaaacaagc   2220
attttcagtt tcagaggtcg ggcaaaggat gttggatctg aaaatgactt tgctgatgat   2280
gaacacagca catttgaaga cagcgaaagc aggagagact cactgtttgt gccgcacaga   2340
```

```
catggagagc gacgcaacag taacgttagt caggccagta tgtcatccag gatggtgcca   2400
gggcttccag caaatgggaa gatgcacagc actgtggatt gcaatggtgt ggtttccttg   2460
gtgggtggac cttcagctct aacgtcacct actggacaac ttcccccaga gggcaccacc   2520
acagaaacgg aagtcagaaa gagaaggtta agctcttacc agatttcaat ggagatgctg   2580
gaggattcct ctggaaggca aagagccgtg agcatagcca gcattctgac caacacaatg   2640
gaagaacttg aagaatctag acagaaatgt ccgccatgct ggtatagatt tgccaatgtg   2700
ttcttgatct gggactgctg tgatgcatgg ttaaaagtaa aacatcttgt gaatttaatt   2760
gttatggatc catttgttga tcttgccatc actatttgca ttgtcttaaa taccctcttt   2820
atggccatgg agcactaccc catgactgag caattcagta gtgtgttgac tgtaggaaac   2880
ctggtcttta ctgggatttt cacagcagaa atggttctca agatcattgc catggatcct   2940
tattactatt tccaagaagg ctggaatatc tttgatggaa ttattgtcag cctcagttta   3000
atggagcttg gtctgtcaaa tgtggaggga ttgtctgtac tgcgatcatt cagactgctt   3060
agagttttca agttggcaaa atcctggccc acactaaata tgctaattaa gatcattggc   3120
aattctgtgg gggctctagg aaacctcacc ttggtgttgg ccatcatcgt cttcattttt   3180
gctgtggtcg gcatgcagct ctttggtaag agctacaaag aatgtgtctg caagatcaat   3240
gatgactgta cgctcccacg gtggcacatg aacgacttct tccactcctt cctgattgtg   3300
ttccgcgtgc tgtgtggaga gtggatagag accatgtggg actgtatgga ggtcgctggc   3360
caaaccatgt gccttattgt tttcatgttg gtcatggtca ttggaaacct tgtggttctg   3420
aacctctttc tggccttatt gttgagttca tttagctcag acaaccttgc tgctactgat   3480
gatgacaatg aaatgaataa tctgcagatt gcagtaggaa gaatgcaaaa gggaattgat   3540
tatgtgaaaa ataagatgcg ggagtgtttc caaaaagcct tttttagaaa gccaaaagtt   3600
atagaaatcc atgaaggcaa taagatagac agctgcatgt ccaataatac tggaattgaa   3660
ataagcaaag agcttaatta tcttagagat gggaatggaa ccaccagtgg tgtaggtact   3720
ggaagcagtg ttgaaaaata cgtaatcgat gaaaatgatt atatgtcatt cataaacaac   3780
cccagcctca ccgtcacagt gccaattgct gttggagagt ctgactttga aaacttaaat   3840
actgaagagt tcagcagtga gtcagaacta gaagaaagca aagagaaatt aaatgcaacc   3900
agctcatctg aaggaagcac agttgatgtt gttctacccc gagaaggtga acaagctgaa   3960
actgaacccg aagaagacct taaaccggaa gcttgtttta ctgaaggatg tattaaaaag   4020
tttccattct gtcaagtaag tacagaagaa ggcaaaggga agatctggtg gaatcttcga   4080
aaaacctgct acagtattgt tgagcacaac tggtttgaga ctttcattgt gttcatgatc   4140
cttctcagta gtggtgcatt ggcctttgaa gatatataca ttgaacagcg aaagactatc   4200
aaaaccatgc tagaatatgc tgacaaagtc tttacctata tattcattct ggaaatgctt   4260
ctcaaatggg ttgcttatgg atttcaaaca tatttcacta atgcctggtg ctggctagat   4320
ttcttgatcg ttgatgtttc tttggttagc ctggtagcca atgctcttgg ctactcagaa   4380
ctcggtgcca tcaaatcatt acggacatta agagctttaa gacctctaag agccttatcc   4440
cggtttgaag gcatgagggt ggttgtgaat gctcttgttg gagcaattcc ctctatcatg   4500
aatgtgctgt tggtctgtct catcttctgg ttgatcttta gcatcatggg tgtgaatttg   4560
tttgctggca agttctacca ctgtgttaac atgacaacgg gtaacatgtt tgacattagt   4620
gatgttaaca atttgagtga ctgtcaggct cttggcaagc aagctcggtg gaaaaacgtg   4680
```

```
aaagtaaact ttgataatgt tggcgctggc tatcttgcac tgcttcaagt ggccacattt   4740
aaaggctgga tggatattat gtatgcagct gttgattcac gagatgttaa acttcagcct   4800
gtatatgaag aaaatctgta catgtattta tactttgtca tctttatcat ctttgggtca   4860
ttcttcactc tgaatctatt cattggtgtc atcatagata acttcaacca gcagaaaaag   4920
aagtttggag gtcaagacat ctttatgaca gaggaacaga aaaaatatta caatgcaatg   4980
aagaaacttg gatccaagaa acctcagaaa cccatacctc gcccagcaaa caaattccaa   5040
ggaatggtct ttgattttgt aaccagacaa gtctttgata tcagcatcat gatcctcatc   5100
tgcctcaaca tggtcaccat gatggtggaa acggatgacc agggcaaata catgacccta   5160
gttttgtccc ggatcaacct agtgttcatt gttctgttca ctggagaatt tgtgctgaag   5220
ctcgtctccc tcagacacta ctacttcact ataggctgga acatctttga ctttgtggtg   5280
gtgattctct ccattgtagg tatgtttctg gctgagatga tagaaaagta ttttgtgtcc   5340
cctaccttgt tccgagtgat ccgtcttgcc aggattggcc gaatcctacg tctgatcaaa   5400
ggagcaaagg ggatccgcac gctgctcttt gctttgatga tgtcccttcc tgcgttgttt   5460
aacatcggcc tcctgctctt cctggtcatg tttatctatg ccatctttgg gatgtccaac   5520
tttgcctatg ttaaaaagga agctggaatt gatgacatgt tcaactttga gacctttggc   5580
aacagcatga tctgcttgtt ccaaattaca acctctgctg gctgggatgg attgctagca   5640
cctattctta atagtgcacc acccgactgt gaccctgaca caattcaccc tggcagctca   5700
gttaagggag actgtgggaa cccatctgtt gggattttct tttttgtcag ttacatcatc   5760
atatccttcc tggttgtggt gaacatgtac atcgcggtca tcctggagaa cttcagtgtt   5820
gctactgaag aaagtgcaga gcccctgagt gaggatgact ttgagatgtt ctatgaggtt   5880
tgggaaaagt ttgatcccga tgcgacccag tttatagagt tctctaaact ctctgatttt   5940
gcagctgccc tggatcctcc tcttctcata gcaaaaccca acaaagtcca gcttattgcc   6000
atggatctgc ccatggtcag tggtgaccgg atccactgtc ttgatatttt atttgccttt   6060
acaaagcgtg ttttgggtga gagtggagag atggatgccc ttcgaataca gatggaagac   6120
aggtttatgg catcaaaccc ctccaaagtc tcttatgagc ctattacaac cactttgaaa   6180
cgtaaacaag aggaggtgtc tgccgctatc attcagcgta atttcagatg ttatctttta   6240
aagcaaaggt taaaaaatat atcaagtaac tataacaaag aggcaattaa agggaggatt   6300
gacttaccta taaaacaaga catgattatt gacaaactaa atgggaactc cactccagaa   6360
aaaacagatg ggagttcctc taccacctct cctccttcct atgatagtgt aacaaaacca   6420
gacaaggaaa agtttgagaa agacaaacca gaaaaagaaa gcaaaggaaa agaggtcaga   6480
gaaaatcaaa agtaaaaaga aacaaagaat tatctttgtg atcaattgtt tacagcctat   6540
gaaggtaaag tatatgtgtc aactggactt caagaggagg tccatgccaa actgactgtt   6600
ttaacaaata ctcatagtca gtgcctatac aagacagtga agtgacctct ctgtcactgc   6660
aactctgtga agcagggtat caacattgac aagaggttgc tgtttttatt accagctgac   6720
actgctgagg agaaacccaa tggctaccta gactataggg atagttgtgc aaagtgaaca   6780
ttgtaactac accaaacacc tttagtacag tccttgcatc cattctattt ttaacttcca   6840
tatctgccat atttttacaa aatttgttct agtgcatttc catggtcccc aattcatagt   6900
ttattcataa tgctatgtca ctatttttgt aaatgaggtt tacgttgaag aaacagtata   6960
caagaaccct gtctctcaaa tgatcagaca aaggtgtttt gccagagaga taaaattttt   7020
gctcaaaacc agaaaaagaa ttgtaatggc tacagtttca gttacttcca ttttctagat   7080
```

```
ggctttaatt ttgaaagtat tttagtctgt tatgtttgtt tctatctgaa cagttatgtg   7140

cctgtaaagt ctcctctaat atttaaagga ttatttttat gcaaagtatt ctgtttcagc   7200

aagtgcaaat tttattctaa gtttcagagc tctatattta atttaggtca aatgctttcc   7260

aaaaagtaat ctaataaatc cattctagaa aaatatatct aaagtattgc tttagaatag   7320

ttgttccact ttctgctgca gtattgcttt gccatcttct gctctcagca aagctgatag   7380

tctatgtcaa ttaaataccc tatgttatgt aaatagttat tttatcctgt ggtgcatgtt   7440

tgggcaaata tatatatagc ctgataaaca acttctatta aatcaaatat gtaccacagt   7500

gtatgtgtct tttgcaagct tccaacaggg atgtatcctg tatcattcat taaacatagt   7560

ttaaaggcta tcactaatgc atgttaatat tgcctatgct gctctatttt actcaatcca   7620

ttcttcacaa gtcttggtta aagaatgtca catattggtg atagaatgaa ttcaacctgc   7680

tctgtccatt atgtcaagca gaataatttg aagctattta caaacacctt tacttttgca   7740

cttttaattc aacatgagta tcatatggta tctctctaga tttcaaggaa acacactgga   7800

tactgcctac tgacaaaacc tattcttcat attttgctaa aaatatgtct aaaacttgtt   7860

taaatataaa taatgtaaaa atataatcaa ctttatttgt cagcattttg tacataagaa   7920

aattattttc aggttgatga catcacaatt tattttactt tatgcttttg cttttgattt   7980

ttaatcacaa ttccaaactt ttgaatccat aagatttttc aatggataat ttcctaaaat   8040

aaaagttaga taatgggttt tatggatttc tttgttataa tatattttct accattccaa   8100

taggagatac attggtcaaa cactcaaacc tagatcattt tctaccaact atggttgcct   8160

caatataacc ttttattcat agatgttttt ttttattcaa cttttgtagt atttacgtat   8220

gcagactagt cttatttttt taattcctgc tgcactaaag ctattacaaa tataacatgg   8280

actttgttct ttttagccat gaacaaagtg gcaaagttgt gcaattacct aacatgatat   8340

aaatttttgt tttttgcaca aaccaaaagt ttaatgttaa ttctttttac aaaactattt   8400

actgtagtgt attgaagaac tgcatgcagg gaattgctat tgctaaaaag aatggtgagc   8460

tacgtcatta ttgagccaaa agaataaatt tcatttttta ttgcatttca cttattggcc   8520

tctggggttt tttgtttttg ttttttgctg ttggcagttt aaaatatata taattaataa   8580

aacctgtgct tgatctgaca tttgtataca taaaagttta catgaatttt acaacaaact   8640

agtgcatgat tcaccaagca gtactacaga acaaaggcaa attaaaagca gctttgtgaa   8700

cttttatgtg tgcaaaggat caagttcaca tgttccaact ttcaggtttg ataataatag   8760

tagtaaccac ctacaatagc tttcaatttc aattaactcc cttggctata agcatctaaa   8820

ctcatcttct ttcaatataa ttgatgctat ctcctaatta cttggtggct aataaatgtt   8880

acattctttg ttacttaaat gcattatata aactcctatg tatacataag gtattaatga   8940

tatagttatt gagaatttat attaactttt ttttcaagaa cccttggatt tatgtgaggt   9000

caaaaccaaa ctcttattct cagtggaaaa ctccagttgt aatgcatatt tttaaagaca   9060

atttggatct aaatatgtat ttcataattc tcccataata aattatataa ggtggctaat   9120

tggaaaaaaa aaaaaaaaaa a                                               9141
```

<210> SEQ ID NO 4
<211> LENGTH: 7805
<212> TYPE: DNA
<213> ORGANISM: Homo sapiens

<400> SEQUENCE: 4

-continued

```
ccagcacccc ggggctgcgc actgcagctc cccaggccac ccaccaccct tctggtctct     60
gagcccagga tgcgaggatg gccagaccat ctctgtgcac cctggtgcct ctgggccctg    120
agtgcttgcg ccccttcacc cgggagtcac tggcagccat agaacagcgg gcggtggagg    180
aggaggcccg gctgcagcgg aataagcaga tggagattga ggagcccgaa cggaagccac    240
gaagtgactt ggaggctggc aagaacctac ccatgatcta cggagacccc ccgccggagg    300
tcatcggcat cccccctggag gacctggatc cctactacag caataagaag accttcatcg    360
tactcaacaa gggcaaggcc atcttccgct tctccgccac acctgctctc tacctgctga    420
gcccttcag cgtagtcagg cgcggggcca tcaaggtgct catccatgcg ctgttcagca    480
tgttcatcat gatcaccatc ttgaccaact gcgtattcat gaccatgagt gacccgcctc    540
cctggtccaa gaatgtggag tacaccttca cagggatcta cacctttgag tccctcatca    600
agatactggc ccgaggcttc tgtgtcgacg acttcacatt cctccgggac ccctggaact    660
ggctggactt cagtgtcatc atgatggcgt acctgacaga gtttgtggac ttgggcaaca    720
tctcagccct gaggaccttc cgggtgctgc gggccctcaa aaccatcacg gtcatcccag    780
ggctgaagac gatcgtgggg gccctgatcc agtcggtgaa aaagctgtcg gatgtgatga    840
tcctcactgt cttctgcctg agcgtctttg cgctggtagg actgcagctc ttcatgggaa    900
acctgaggca gaagtgtgtg cgctggcccc cgccgttcaa cgacaccaac accacgtggt    960
acagcaatga cacgtggtac ggcaatgaca catggtatgg caatgagatg tggtacggca   1020
atgactcatg gtatgccaac gacacgtgga acagccatgc aagctgggcc accaacgata   1080
cctttgattg ggacgcctac atcagtgatg aagggaactt ctacttcctg gagggctcca   1140
acgatgccct gctctgtggg aacagcagtg atgctgggca ctgccctgag ggttatgagt   1200
gcatcaagac cgggcggaac cccaactatg gctacaccag ctatgacacc ttcagctggg   1260
ccttcttggc tctcttccgc ctcatgacac aggactattg ggagaacctc ttccagctga   1320
cccttcgagc agctggcaag acctacatga tcttcttcgt ggtcatcatc ttcctgggct   1380
ctttctacct catcaatctg atcctggccg tggtggccat ggcatatgcc gagcagaatg   1440
aggccaccct ggccgaggat aaggagaaag aggaggagtt tcagcagatg cttgagaagt   1500
tcaaaaagca ccaggaggag ctggagaagg ccaaggccgc ccaagctctg gaaggtgggg   1560
aggcagatgg ggacccagcc catggcaaag actgcaatgg cagcctggac acatcgcaag   1620
gggagaaggg agccccgagg cagagcagca gcggagacag cggcatctcc gacgccatgg   1680
aagaactgga agaggcccac caaaagtgcc caccatggtg gtacaagtgc gcccacaaag   1740
tgctcatatg gaactgctgc gccccgtggc tgaagttcaa gaacatcatc cacctgatcg   1800
tcatggaccc gttcgtggac ctgggcatca ccatctgcat cgtgctcaac accctcttca   1860
tggccatgga acattacccc atgacggagc actttgacaa cgtgctcact gtgggcaacc   1920
tggtcttcac aggcatcttc acagcagaga tggttctgaa gctgattgcc atggacccct   1980
acgagtattt ccagcagggt tggaatatct tcgacagcat catcgtcacc ctcagcctgg   2040
tagagctagg cctggccaac gtacagggac tgtctgtgct acgctccttc cgtctgctgc   2100
gggtcttcaa gctggccaag tcgtggccaa cgctgaacat gctcatcaag atcattggca   2160
attcagtggg ggcgctgggt aacctgacgc tggtgctggc tatcatcgtg ttcatcttcg   2220
ccgtggtggg catgcagctg tttggcaaga gctacaagga gtgcgtgtgc aagattgcct   2280
tggactgcaa cctgccgcgc tggcacatgc atgatttctt ccactccttc ctcatcgtct   2340
tccgcatcct gtgcggggag tggatcgaga ccatgtggga ctgcatggag gtggccggcc   2400
```

```
aagccatgtg cctcaccgtc ttcctcatgg tcatggtcat cggcaatctt gtggtcctga   2460
acctgttcct ggctctgctg ctgagctcct tcagcgccga cagtctggca gcctcggatg   2520
aggatggcga gatgaacaac ctgcagattg ccatcgggcg catcaagttg ggcatcggct   2580
ttgccaaggc cttcctcctg ggctgctgc atggcaagat cctgagcccc aaggacatca   2640
tgctcagcct cggggaggct gacggggccg gggaggctgg agaggcgggg gagactgccc   2700
ccgaggatga gaagaaggag ccgcccgagg aggacctgaa gaaggacaat cacatcctga   2760
accacatggg cctggctgac ggcccccat ccagcctcga gctggaccac cttaacttca   2820
tcaacaaccc ctacctgacc atacaggtgc ccatcgcctc cgaggagtcc gacctggaga   2880
tgcccaccga ggaggaaacc gacactttct cagagcctga ggatagcaag aagccgccgc   2940
agcctctcta tgatgggaac tcgtccgtct gcagcacagc tgactacaag cccccgagg   3000
aggaccctga ggagcaggca gaggagaacc ccgagggga gcagcctgag gagtgcttca   3060
ctgaggcctg cgtgcagcgc tggccctgcc tctacgtgga catctcccag ggccgtggga   3120
agaagtggtg gactctgcgc agggcctgct tcaagattgt cgagcacaac tggttcgaga   3180
ccttcattgt cttcatgatc ctgctcagca gtggggctct ggccttcgag gacatctaca   3240
ttgagcagcg gcgagtcatt cgcaccatcc tagaatatgc cgacaaggtc ttcacctaca   3300
tcttcatcat ggagatgctg ctcaaatggg tggcctacgg ctttaaggtg tacttcacca   3360
acgcctggtg ctggctcgac ttcctcatcg tggatgtctc catcatcagc ttggtggcca   3420
actggctggg ctactcggag ctgggaccca tcaaatccct gcggacactg cgggccctgc   3480
gtcccctgag ggcactgtcc cgattcgagg gcatgagggt ggtggtgaac gccctcctag   3540
gcgccatccc ctccatcatg aatgtgctgc ttgtctgcct catcttctgg ctgatcttca   3600
gcatcatggg tgtcaacctg tttgccggca agttctacta ctgcatcaac accaccacct   3660
ctgagaggtt cgacatctcc gaggtcaaca acaagtctga gtgcgagagc ctcatgcaca   3720
caggccaggt ccgctggctc aatgtcaagg tcaactacga caacgtgggt ctgggctacc   3780
tctccctcct gcaggtggcc accttcaagg gttggatgga catcatgtat gcagccgtgg   3840
actcccggga gaaggaggag cagccgcagt acgaggtgaa cctctacatg tacctctact   3900
ttgtcatctt catcatcttt ggctccttct tcaccctcaa cctcttcatt ggcgtcatca   3960
ttgacaactt caaccagcag aagaagaagt taggggggaa agacatcttt atgacggagg   4020
aacagaagaa atactataac gccatgaaga agcttggctc caagaagcct cagaagccaa   4080
ttccccggcc ccagaacaag atccagggca tggtgtatga cctcgtgacg aagcaggcct   4140
tcgacatcac catcatgatc ctcatctgcc tcaacatggt caccatgatg gtggagacag   4200
acaaccagag ccagctcaag gtggacatcc tgtacaacat caacatgatc ttcatcatca   4260
tcttcacagg ggagtgcgtg ctcaagatgc tcgccctgcg ccagtactac ttcaccgttg   4320
gctggaacat ctttgacttc gtggtcgtca tcctgtccat tgtgggcctt gccctctctg   4380
acctgatcca gaagtacttc gtgtcaccca cgctgttccg tgtgatccgc ctggcgcgga   4440
ttgggcgtgt cctgcggctg atccgcgggg ccaagggcat ccggacgctg ctgttcgccc   4500
tcatgatgtc gctgcctgcc ctcttcaaca tcggcctcct cctcttcctg gtcatgttca   4560
tctactccat cttcggcatg tccaactttg cctacgtcaa gaaggagtcg ggcatcgatg   4620
atatgttcaa cttcgagacc ttcggcaaca gcatcatctg cctgttcgag atcaccacgt   4680
cggccggctg ggacgggctc ctcaacccca tcctcaacag cgggccccca gactgtgacc   4740
```

```
ccaacctgga gaacccgggc accagtgtca agggtgactg cggcaacccc tccatcggca   4800
tctgcttctt ctgcagctat atcatcatct ccttcctcat cgtggtcaac atgtacatcg   4860
ccatcatcct ggagaacttc aatgtggcca cagaggagag cagcgagccc cttggtgaag   4920
atgactttga gatgttctac gagacatggg agaagttcga ccccgacgcc acccagttca   4980
tcgcctacag ccgcctctca gacttcgtgg acaccctgca ggaaccgctg aggattgcca   5040
agcccaacaa gatcaagctc atcacactgg acttgcccat ggtgccaggg gacaagatcc   5100
actgcctgga catcctcttt gccctgacca aagaggtcct gggtgactct ggggaaatgg   5160
acgccctcaa gcagaccatg gaggagaagt tcatggcagc caacccctcc aaggtgtcct   5220
acgagcccat caccaccacc ctcaagagga agcacgagga ggtgtgcgcc atcaagatcc   5280
agagggccta ccgccggcac ctgctacagc gctccatgaa gcaggcatcc tacatgtacc   5340
gccacagcca cgacggcagc ggggatgacg cccctgagaa ggaggggctg cttgccaaca   5400
ccatgagcaa gatgtatggc cacgagaatg ggaacagcag ctcgccaagc ccggaggaga   5460
agggcgaggc aggggacgcc ggacccacta tggggctgat gcccatcagc ccctcagaca   5520
ctgcctggcc tcccgcccct cccccagggc agactgtgcg cccaggtgtc aaggagtctc   5580
ttgtctagca ggcagcatcg ggtggcccca ctgagtctcg gcatagtccc cagagctccc   5640
ccgtggtgcc tgcacacaga gtgagggagg agggctttga atctgggact gtgcctggct   5700
ccctgatggg ggacaggatt tggccacact ggggctgaca cccaggcccg agcgcctgcg   5760
ttcccagacc atgggaaatg ggaattgcgc tcaggggctc catgctgggt ctgaggcccc   5820
tgcctccaag atttaacctg caagttgctc tgacctcctc tgggccctgt cgcccctcct   5880
tttggcctgg gggaggtcag aacattcgaa tctctgcccc tcacttgagg aggagctggc   5940
ctgcggtgga gggatcagtt gccccccatc accagagtct taagggtcac tggcctctcc   6000
ccaggaagtg gctcagaccc ctcagcccca gcccagacaa agatgtctta acctcaggga   6060
gtgcagacac ctaaccccag ggcactgcca gcccaccccc tttgactctg gggtgcagct   6120
tcacccacca ggccagctca ggaattccct ggaaaaggga aatgtgactg gttcagaaat   6180
agctcctcaa agcctcaaaa cctgattggc cactggatcc tgctgctttg ggctgggatg   6240
gtgactcctg aaacctcttc ctaggccacg tccaggtccg tagctcccct ggctggctcc   6300
taggggaaga gcagaaggaa ggatgccact tgggaatgaa ttgtcctttt ctaggaagca   6360
cgggggagtg agacaggctg ggtcctgcca gctggatcgc tgcacatggc ctgagcatcc   6420
agacctgagc gggagtcagg gacctgctgc tcagtaagaa gattctcgcc ccttccctct   6480
ctccctgcct cactcctccg tgagcaccac cagggctcca ggagcctcat ccagcctcag   6540
agatctccct tctcatctcc ccacgcccgt ctctttctca cctttcccac ctctctcccc   6600
aaagtgatcc taagaatgta cagttgagct caggttagat atttcgaccc tggggcgtgc   6660
agcagggaag gcccaactgg ttcaggctca accttccaac ttcctgtggc ctgaagaagc   6720
acttctgctg catcgctgtt ctgggcatgg cagggccagg cctctgctgg ctcaggagga   6780
ggggtgagag acctgctcag gcgtcgctgg atttattcac ttgtgtgtgt acctgtggct   6840
gtgtgtctgc ttgtatgctt ttataggcct gtgtgtatag ctgtgtgtgt gttcaagtgc   6900
gtgactgtat gtgtgtgtgt gaaccactgt gtactggagc ctgcattatg cacgtgtctg   6960
ggtatctttg tatatatgtg tatatatgtg tgccctggac tgtttcaagg tccatggagt   7020
acggctggtg tgtcatactg tgcaggcctg tccctgggag tgttcccgtg cctgggagag   7080
tggacctgtg ctgtgagtgt gtggatgcgt gtgaacgcat gtggtaaggt gtgtactcag   7140
```

```
ggcattctgt tggcctaagt gcctcttctt tttcttcttg tttctcatga aaagtttgat   7200
taaaattcag gaagcagcaa aaccttcaaa acaagacatg tatgtgtgct tgagtgtgtg   7260
aacacgtgtg tgtgtgtgca catctacatg ccatgcctat gggccagagt tgtctttatt   7320
gtccaccatg ctctctcacc tgctcccagt cctgcctgaa cagccctctc tctcactccc   7380
ctctcctccc cttcctgttt ctcgttgtca cacccatggc ctcagccctg ctccctgcct   7440
cctgcctatg tctcctctat ggaaggaggc ctccactcct tccatctctt ccttcagaag   7500
tttcgtctaa tgggggcagt ctccccttcc tggcacattg cccctctgcc ttgccctcct   7560
gggccctggg ctggcacagc ccctggagcc tcagaaatct gtttgattgg atattctcct   7620
cggactgtgt gcaggttgca gaggaagagt agatgagccg ggtccggcct ctccctgcct   7680
gtggcccctc ccctgcagac ggatgcccat tcctgcctgg tccagtgggg aacaggtccc   7740
acgccaggcc agcaggcggg ctcctttgta cagttcttac aataaaccct ccttggtgcc   7800
tctgg                                                               7805
```

```
<210> SEQ ID NO 5
<211> LENGTH: 8504
<212> TYPE: DNA
<213> ORGANISM: Homo sapiens

<400> SEQUENCE: 5

agacggcggc ggcgcccgta ggatgcaggg atcgctcccc cggggccgct gagcctgcgc     60
ccagtgcccc gagccccgcg ccgagccgag tccgcgccaa gcagcagccg cccaccccgg    120
ggcccggccg ggggaccagc agcttcccca caggcaacgt gaggagagcc tgtgcccaga    180
agcaggatga gaagatggca aacttcctat tacctcgggg caccagcagc ttccgcaggt    240
tcacacggga gtccctggca gccatcgaga agcgcatggc agagaagcaa gcccgcggct    300
caaccacctt gcaggagagc cgagaggggc tgcccgagga ggaggctccc cggccccagc    360
tggacctgca ggcctccaaa aagctgccag atctctatgg caatccaccc caagagctca    420
tcggagagcc cctggaggac ctggacccct tctatagcac ccaaaagact ttcatcgtac    480
tgaataaagg caagaccatc ttccggttca gtgccaccaa cgccttgtat gtcctcagtc    540
ccttccaccc catccggaga gcggctgtga agattctggt tcactcgctc ttcaacatgc    600
tcatcatgtg caccatcctc accaactgcg tgttcatggc ccagcacgac cctccaccct    660
ggaccaagta tgtcgagtac accttcaccg ccatttacac ctttgagtct ctggtcaaga    720
ttctggctcg aggcttctgc ctgcacgcgt tcactttcct tcgggaccca tggaactggc    780
tggactttag tgtgattatc atggcataca caactgaatt tgtggacctg ggcaatgtct    840
cagccttacg caccttccga gtcctccggg ccctgaaaac tatatcagtc atttcagggc    900
tgaagaccat cgtgggggcc ctgatccagt ctgtgaagaa gctggctgat gtgatggtcc    960
tcacagtctt ctgcctcagc gtctttgccc tcatcggcct gcagctcttc atgggcaacc   1020
taaggcacaa gtgcgtgcgc aacttcacag cgctcaacgg caccaacggc tccgtggagg   1080
ccgacggctt ggtctgggaa tccctggacc tttacctcag tgatccagaa aattacctgc   1140
tcaagaacgg cacctctgat gtgttactgt gtgggaacag ctctgacgct gggacatgtc   1200
cggagggcta ccggtgccta aaggcaggcg agaaccccga ccacggctac accagcttcg   1260
attcctttgc ctgggccttt cttgcactct tccgcctgat gacgcaggac tgctgggagc   1320
gcctctatca gcagaccctc aggtccgcag ggaagatcta catgatcttc ttcatgcttg   1380
```

```
tcatcttcct ggggtccttc tacctggtga acctgatcct ggccgtggtc gcaatggcct   1440
atgaggagca aaaccaagcc accatcgctg agaccgagga gaaggaaaag cgcttccagg   1500
aggccatgga aatgctcaag aaagaacacg aggccctcac catcaggggt gtggataccg   1560
tgtcccgtag ctccttggag atgtcccctt tggccccagt aaacagccat gagagaagaa   1620
gcaagaggag aaaacggatg tcttcaggaa ctgaggagtg tggggaggac aggctcccca   1680
agtctgactc agaagatggt cccagagcaa tgaatcatct cagcctcacc cgtggcctca   1740
gcaggacttc tatgaagcca cgttccagcc gcgggagcat tttcaccttt cgcaggcgag   1800
acctgggttc tgaagcagat tttgcagatg atgaaaacag cacagcgggg gagagcgaga   1860
gccaccacac atcactgctg gtgccctggc ccctgcgccg gaccagtgcc cagggacagc   1920
ccagtcccgg aacctcggct cctggccacg ccctccatgg caaaaagaac agcactgtgg   1980
actgcaatgg ggtggtctca ttactggggg caggcgaccc agaggccaca tccccaggaa   2040
gccacctcct ccgccctgtg atgctagagc acccgccaga cacgaccacg ccatcggagg   2100
agccaggcgg gccccagatg ctgacctccc aggctccgtg tgtagatggc ttcgaggagc   2160
caggagcacg gcagcgggcc ctcagcgcag tcagcgtcct caccagcgca ctggaagagt   2220
tagaggagtc tcgccacaag tgtccaccat gctggaaccg tctcgcccag cgctacctga   2280
tctgggagtg ctgcccgctg tggatgtcca tcaagcaggg agtgaagttg gtggtcatgg   2340
acccgtttac tgacctcacc atcactatgt gcatcgtact caacacactc ttcatggcgc   2400
tggagcacta caacatgaca agtgaattcg aggagatgct gcaggtcgga aacctggtct   2460
tcacagggat tttcacagca gagatgacct tcaagatcat tgccctcgac ccctactact   2520
acttccaaca gggctggaac atcttcgaca gcatcatcgt catccttagc ctcatggagc   2580
tgggcctgtc ccgcatgagc aacttgtcgg tgctgcgctc cttccgcctg ctgcgggtct   2640
tcaagctggc caaatcatgg cccaccctga acacactcat caagatcatc gggaactcag   2700
tgggggcact ggggaacctg acactggtgc tagccatcat cgtgttcatc tttgctgtgg   2760
tgggcatgca gctctttggc aagaactact cggagctgag ggacagcgac tcaggcctgc   2820
tgcctcgctg gcacatgatg gacttctttc atgccttcct catcatcttc cgcatcctct   2880
gtggagagtg gatcgagacc atgtgggact gcatggaggt gtcggggcag tcattatgcc   2940
tgctggtctt cttgcttgtt atggtcattg gcaaccttgt ggtcctgaat ctcttcctgg   3000
ccttgctgct cagctccttc agtgcagaca acctcacagc ccctgatgag gacagagaga   3060
tgaacaacct ccagctggcc ctggcccgca tccagagggg cctgcgcttt gtcaagcgga   3120
ccacctggga tttctgctgt ggtctcctgc ggcagcggcc tcagaagccc gcagcccttg   3180
ccgcccaggg ccagctgccc agctgcattg ccacccccta ctccccgcca cccccagaga   3240
cggagaaggt gcctcccacc cgcaaggaaa cacggtttga ggaaggcgag caaccaggcc   3300
agggcacccc cggggatcca gagcccgtgt gtgtgcccat cgctgtggcc gagtcagaca   3360
cagatgacca agaagaagat gaggagaaca gcctgggcac ggaggaggag tccagcaagc   3420
agcaggaatc ccagcctgtg tccggtggcc cagaggcccc tccggattcc aggacctgga   3480
gccaggtgtc agcgactgcc tcctctgagg ccgaggccag tgcatctcag gccgactggc   3540
ggcagcagtg gaaagcggaa ccccaggccc cagggtgcgg tgagacccca gaggacagtt   3600
gctccgaggg cagcacagca gacatgacca acaccgctga gctcctggag cagatccctg   3660
acctcggcca ggatgtcaag gacccagagg actgcttcac tgaaggctgt gtccggcgct   3720
gtccctgctg tgcggtggac accacacagg ccccagggaa ggtctggtgg cggttgcgca   3780
```

```
agacctgcta ccacatcgtg gagcacagct ggttcgagac attcatcatc ttcatgatcc   3840
tactcagcag tggagcgctg gccttcgagg acatctacct agaggagcgg aagaccatca   3900
aggttctgct tgagtatgcc gacaagatgt tcacatatgt cttcgtgctg gagatgctgc   3960
tcaagtgggt ggcctacggc ttcaagaagt acttcaccaa tgcctggtgc tggctcgact   4020
tcctcatcgt agacgtctct ctggtcagcc tggtggccaa caccctgggc tttgccgaga   4080
tgggccccat caagtcactg cggacgctgc gtgcactccg tcctctgaga gctctgtcac   4140
gatttgaggg catgagggtg gtggtcaatg ccctggtggg cgccatcccg tccatcatga   4200
acgtcctcct cgtctgcctc atcttctggc tcatcttcag catcatgggc gtgaacctct   4260
ttgcggggaa gtttgggagg tgcatcaacc agacagaggg agacttgcct ttgaactaca   4320
ccatcgtgaa caacaagagc cagtgtgagt ccttgaactt gaccggagaa ttgtactgga   4380
ccaaggtgaa agtcaacttt gacaacgtgg gggccgggta cctggccctt ctgcaggtgg   4440
caacatttaa aggctggatg gacattatgt atgcagctgt ggactccagg gggtatgaag   4500
agcagcctca gtgggaatac aacctctaca tgtacatcta ttttgtcatt ttcatcatct   4560
ttgggtcttt cttcaccctg aacctcttta ttggtgtcat cattgacaac ttcaaccaac   4620
agaagaaaaa gttagggggc caggacatct tcatgacaga ggagcagaag aagtactaca   4680
atgccatgaa gaagctgggc tccaagaagc cccagaagcc catcccacgg cccctgaaca   4740
agtaccaggg cttcatattc gacattgtga ccaagcaggc ctttgacgtc accatcatgt   4800
ttctgatctg cttgaatatg gtgaccatga tggtggagac agatgaccaa agtcctgaga   4860
aaatcaacat cttggccaag atcaacctgc tctttgtggc catcttcaca ggcgagtgta   4920
ttgtcaagct ggctgccctg cgccactact acttcaccaa cagctggaat atcttcgact   4980
tcgtggttgt catcctctcc atcgtgggca ctgtgctctc ggacatcatc cagaagtact   5040
tcttctcccc gacgctcttc cgagtcatcc gcctggcccg aataggccgc atcctcagac   5100
tgatccgagg ggccaagggg atccgcacgc tgctctttgc cctcatgatg tccctgcctg   5160
ccctcttcaa catcgggctg ctgctcttcc tcgtcatgtt catctactcc atctttggca   5220
tggccaactt cgcttatgtc aagtgggagg ctggcatcga cgacatgttc aacttccaga   5280
ccttcgccaa cagcatgctg tgcctcttcc agatcaccac gtcggccggc tgggatggcc   5340
tcctcagccc catcctcaac actgggccgc cctactgcga ccccactctg cccaacagca   5400
atggctctcg gggggactgc gggagcccag ccgtgggcat cctcttcttc accacctaca   5460
tcatcatctc cttcctcatc gtggtcaaca tgtacattgc catcatcctg gagaacttca   5520
gcgtggccac ggaggagagc accgagcccc tgagtgagga cgacttcgat atgttctatg   5580
agatctggga gaaatttgac ccagaggcca ctcagtttat tgagtattcg gtcctgtctg   5640
actttgccga tgccctgtct gagccactcc gtatcgccaa gcccaaccag ataagcctca   5700
tcaacatgga cctgcccatg gtgagtgggg accgcatcca ttgcatggac attctctttg   5760
ccttcaccaa aagggtcctg ggggagtctg gggagatgga cgccctgaag atccagatgg   5820
aggagaagtt catggcagcc aacccatcca agatctccta cgagcccatc accaccacac   5880
tccggcgcaa gcacgaagag gtgtcggcca tggttatcca gagagccttc cgcaggcacc   5940
tgctgcaacg ctctttgaag catgcctcct tcctcttccg tcagcaggcg ggcagcggcc   6000
tctccgaaga ggatgcccct gagcgagagg gcctcatcgc ctacgtgatg agtgagaact   6060
tctcccgacc ccttggccca ccctccagct cctccatctc ctccacttcc ttcccaccct   6120
```

```
cctatgacag tgtcactaga gccaccagcg ataacctcca ggtgcggggg tctgactaca   6180
gccacagtga agatctcgcc gacttccccc cttctccgga cagggaccgt gagtccatcg   6240
tgtgagcctc ggcctggctg gccaggacac actgaaaagc agcctttttc accatggcaa   6300
acctaaatgc agtcagtcac aaaccagcct ggggccttcc tggctttggg agtaagaaat   6360
gggcctcagc cccgcggatc aaccaggcag agttctgtgg cgccgcgtgg acagccggag   6420
cagttggcct gtgcttggag gcctcagata gacctgtgac ctggtctggt caggcaatgc   6480
cctgcggctc tggaaagcaa cttcatccca gctgctgagg cgaaatataa aactgagact   6540
gtatatgttg tgaatgggct ttcataaatt tattatattt gatatttttt tacttgagca   6600
aagaactaag gatttttcca tggacatggg cagcaattca cgctgtctct tcttaaccct   6660
gaacaagagt gtctatggag cagccggaag tctgttctca aagcagaagt ggaatccagt   6720
gtggctccca caggtcttca ctgcccaggg gtcgaatggg gtccccctcc cacttgacct   6780
gagatgctgg gagggctgaa cccccactca cacaagcaca cacacacagt cctcacacac   6840
ggaggccaga cacaggccgt gggacccagg ctcccagcct aagggagaca ggcctttccc   6900
tgccggcccc ccaaggatgg ggttcttgtc cacggggctc actctggccc cctattgtct   6960
ccaaggtccc attttccccc tgtgttttca cgcaggtcat attgtcagtc ctacaaaaat   7020
aaaaggcttc cagaggagag tggcctgggt cccagggctg gccctaggca ctgatagttg   7080
ccttttcttc ccctcctgta agagtattaa caaaaccaaa ggacacaagg gtgcaagccc   7140
cattcacggc ctggcatgca gcttgtcctt gctcctggaa cctggcaggc cctgcccagc   7200
cagccatcgg aagagagggc tgagccatgg gggtttgggg ctaagaagtt caccagccct   7260
gagccatggc ggcccctcag cctgcctgaa gagaggaaac tggcgatctc ccagggctct   7320
ctggaccata cgcggaggag ttttctgtgt ggtctccagc tcctctccag acacagagac   7380
atgggagtgg ggagcggagc ttggccctgc gccctgtgca gggaaaggga tggtcaggcc   7440
cagttctcgt gcccttagag gggaatgaac catggcacct ttgagagagg gggcactgtg   7500
gtcaggccca gcctctctgg ctcagcccgg gatcctgatg gcacccacac agaggacctc   7560
tttggggcaa gatccaggtg gtcccatagg tcttgtgaaa aggctttttc agggaaaaat   7620
attttactag tccaatcacc cccaggacct cttcagctgc tgacaatcct atttagcata   7680
tgcaaatctt ttaacataga gaactgtcac cctgaggtaa cagggtcaac tggcgaagcc   7740
tgagcaggca ggggcttggc tgccccattc cagctctccc atggagcccc tccaccgggc   7800
gcatgcctcc caggccacct cagtctcacc tgccggctct gggctggctg ctcctaacct   7860
acctcgccga gctgtcggag ggctggacat ttgtggcagt gctgaagggg gcattgccgg   7920
cgagtaaagt attatgtttc ttcttgtcac cccagttccc ttggtggcaa ccccagaccc   7980
aacccatgcc cctgacagat ctagttctct tctcctgtgt tccctttgag tccagtgtgg   8040
gacacggttt aactgtccca gcgacatttc tccaagtgga aatcctattt ttgtagatct   8100
ccatgctttg ctctcaaggc ttggagaggt atgtgcccct cctgggtgct caccgcctgc   8160
tacacaggca ggaatgcggt tgggaggcag gtcgggctgc cagcccagct ggccggaagg   8220
agactgtggt ttttgtgtgt gtggacagcc cgggagcttt gagacaggtg cctggggctg   8280
gctgcagacg gtgtggttgg gggtgggagg tgagctagac ccaaccctta gcttttagcc   8340
tggctgtcac ctttttaatt tccagaactg cacaatgacc agcaggaggg aaggacagac   8400
atcaagtgcc agatgttgtc tgaactaatc gagcacttct caccaaactt catgtataaa   8460
taaaatacat atttttaaaa caaaccaata aatggcttac atga                    8504
```

<210> SEQ ID NO 6
<211> LENGTH: 7186
<212> TYPE: DNA
<213> ORGANISM: Homo sapiens

<400> SEQUENCE: 6
caggtcctcc accatgtgaa tgccaacatg gccaggtcat tagagctgag ggaaaactag 60
tgcccaaaga tatgaaaaga gtgtggatct tctggagaag tgctgttgtt caacaggtac 120
aaaattggaa atgttggctt caccagaacc taagggcctt gttcccttca ctaaagagtc 180
ttttgaactt ataaaacagc atattgctaa aacacataat gaagaccatg aagaagaaga 240
cttaaagcca actcctgatt tggaagttgg caaaaagctt ccatttattt atggaaacct 300
ttctcaagga atggtgtcag agcccttgga agatgtggac ccatattact acaagaaaaa 360
aaatactttc atagtattaa ataaaaatag aacaatcttc agattcaatg cggcttccat 420
cttgtgtaca ttgtctcctt tcaattgtat tagaagaaca actatcaagg ttttggtaca 480
tccctttttc caactgttta ttctaattag tgtcctgatt gattgcgtat tcatgtccct 540
gactaatttg ccaaaatgga gaccagtatt agagaatact ttgcttggaa tttacacatt 600
tgaaatactt gtaaaactct ttgcaagagg tgtctgggca ggatcatttt ccttcctcgg 660
tgatccatgg aactggctcg atttcagcgt aactgtgttt gaggttatta taagatactc 720
acctctggac ttcattccaa cgcttcaaac tgcaagaact ttgagaattt taaaaattat 780
tcctttaaat caaggtctga aatcccttgt aggggtcctg atccactgct tgaagcagct 840
tattggtgtc attatcctaa ctctgttttt tctgagcata ttttctctaa ttgggatggg 900
gctcttcatg ggcaacttga aacataaatg ttttcgatgg ccccaagaga atgaaaatga 960
aaccctgcac aacagaactg gaaacccata ttatattcga gaaacagaaa acttttatta 1020
tttggaagga gaaagatatg ctctcctttg tggcaacagg acagatgctg gtcagtgtcc 1080
tgaaggatat gtgtgtgtaa aagctggcat aaatcctgat caaggcttca caaattttga 1140
cagttttggc tgggccttat ttgccctatt tcggttaatg gctcaggatt accctgaagt 1200
actttatcac cagatacttt atgcttctgg gaaggtctac atgatatttt ttgtggtggt 1260 aagtttttttg ttttcctttt atatggcaag tttgttctta ggcatacttg ccatggccta 1320
tgaagaagaa aagcagagag ttggtgaaat atctaagaag attgaaccaa aatttcaaca 1380
gactggaaaa gaacttcaag aaggaaatga aacagatgag gccaagacca tacaaataga 1440
aatgaagaaa aggtcaccaa tttccacaga cacatcattg gatgtgttgg aagatgctac 1500
tctcagacat aaggaagaac ttgaaaaatc caagaagata tgcccattat actggtataa 1560
gtttgctaaa actttcttga tctggaattg ttctccctgt tggttaaaat tgaaagagtt 1620
tgtccatagg attataatgg caccatttac tgatcttttc cttatcatat gcataatttt 1680
aaacgtatgt tttctgacct tggagcatta tccaatgagt aaacaaacta acactcttct 1740
caacattgga aacctggttt tcattggaat tttcacagca gaaatgattt ttaaaataat 1800
tgcaatgcat ccatatgggt atttccaagt aggttggaac atttttgata gcatgatagt 1860
gttccatggt ttaatagaac tttgtctagc aaatgttgca ggaatggctc ttcttcgatt 1920
attcaggatg ttaagaattt tcaagttggg aaagtattgg ccaacattcc agattttgat 1980
gtggtctctt agtaactcat gggtggccct gaaagacttg gtcctgttgt tgttcacatt 2040
catcttcttt tctgctgcat tcggcatgaa gctgtttggt aagaattatg aagaatttgt 2100

```
ctgccacata gacaaagact gtcaactccc acgctggcac atgcatgact ttttccactc   2160
cttcctgaat gtgttccgaa ttctctgtgg agagtgggta gagaccttgt gggactgtat   2220
ggaggttgca ggccaatcct ggtgtattcc tttttacctg atggtcattt taattggaaa   2280
tttactggta ctttacctgt ttctggcatt ggtgagctca tttagttcat gcaaggatgt   2340
aacagctgaa gagaataatg aagcaaaaaa tctccagctt gcagtggcaa gaattaaaaa   2400
aggaataaac tatgtgcttc ttaaaatact atgcaaaaca caaaatgtcc caaaggacac   2460
aatggaccat gtaaatgagg tatatgttaa agaagatatt tctgaccata ccctttctga   2520
attgagcaac acccaagatt ttctcaaaga taaggaaaaa agcagtggca cagagaaaaa   2580
cgctactgaa aatgagagcc aatcacttat ccccagtcct agtgtctcag aaactgtacc   2640
aattgcttca ggagaatctg atatagaaaa tctggataat aaggagattc agagtaagtc   2700
tggtgatgga ggcagcaaag agaaaataaa gcaatctagc tcatctgaat gcagtactgt   2760
tgatattgct atctctgaag aagaagaaat gttctatgga ggtgaaagat caaagcatct   2820
gaaaaatggt tgcagacgcg gatcttcact tggtcaaatc agtggagcat ccaagaaagg   2880
aaaaatctgg cagaacatca ggaaaacctg ctgcaagatt gtagagaaca attggtttaa   2940
gtgttttatt gggcttgtta ctctgctcag cactggcact ctggcttttg aagatatata   3000
tatggatcag agaaagacaa ttaaaatttt attagaatat gctgacatga tctttactta   3060
tatcttcatt ctggaaatgc ttctaaaatg gatggcatat ggttttaagg cctatttctc   3120
taatggctgg tacaggctgg acttcgtggt tgttattgtg ttttgtctta gcttaatagg   3180
caaaactcgg gaagaactaa aacctcttat ttccatgaaa ttccttcggc cctcagagt    3240
tctatctcaa tttgaaagaa tgaaggtggt tgtgagagct ttgatcaaaa caaccttacc   3300
cactttgaat gtgtttcttg tctgcctgat gatctggctg atttttagta tcatgggagt   3360
agacttattt gctggcagat tctatgaatg cattgaccca acaagtggag aaaggtttcc   3420
ttcatctgaa gtcatgaata agagtcggtg tgaaagcctt ctgtttaacg aatccatgct   3480
atgggaaaat gcaaaaatga actttgataa tgttggaaat ggtttccttt ctctgcttca   3540
agtagcaaca tttaatggat ggatcactat tatgaattca gcaattgatt ctgttgctgt   3600
taatatacag cctcattttg aagtcaacat ctacatgtat tgttacttta tcaactttat   3660
tatatttgga gtatttctcc ctctgagtat gctgattact gttattattg ataatttcaa   3720
caagcataaa ataaagctgg gaggctcaaa tatctttata acggttaaac agagaaaaca   3780
gtaccgcagg ctgaagaagc taatgtatga ggattctcaa agaccagtac ctcgcccatt   3840
aaacaagctc caaggattca tctttgatgt ggtaacaagc caagctttta atgtcattgt   3900
tatggttctt atatgtttcc aagcaatagc catgatgata gacactgatg ttcagagtct   3960
acaaatgtcc attgctctct actggattaa ctcaattttt gttatgctat atactatgga   4020
atgtatactg aagctcatcg ctttccgttg tttttatttc accattgcgt ggaacatttt   4080
tgattttatg gtggttattt tctccatcac aggactatgt ctgcctatga cagtaggatc   4140
ctaccttgtg cctccttcac ttgtgcaact gatacttctc tcacggatca ttcacatgct   4200
gcgtcttgga aaaggaccaa aggtgtttca taatctgatg cttcctttga tgctgtccct   4260
cccagcatta ttgaacatca ttcttctcat cttcctggtc atgttcatct atgccgtatt   4320
tggaatgtat aattttgcct atgttaaaaa agaagctgga attaatgatg tgtctaattt   4380
tgaaaccttt ggcaacagta tgctctgtct tttcaagtt gcaatatttg ctggttggga    4440
tgggatgctt gatgcaattt tcaacagtaa atggtctgac tgtgatcctg ataaaattaa   4500
```

```
ccctgggact caagttagag gagattgtgg gaacccctct gttgggattt tttattttgt   4560
cagttatatc ctcatatcat ggctgatcat tgtaaatatg tacattgttg ttgtcatgga   4620
gtttttaaat attgcttcta agaagaaaaa caagaccttg agtgaagatg attttaggaa   4680
attctttcag gtatggaaaa ggtttgatcc tgataggacc cagtacatag actctagcaa   4740
gctttcagat tttgcagctg ctcttgatcc tcctcttttc atggcaaaac caaacaaggg   4800
ccagctcatt gctttggacc tccccatggc tgttggggac agaattcatt gcctcgatat   4860
cttacttgct tttacaaaga gagttatggg tcaagatgtg aggatggaga aagttgtttc   4920
agaaatagaa tcagggtttt tgttagccaa ccccttttaag atcacatgtg agccaattac   4980
gactactttg aaacgaaaac aagaggcagt ttcagcaacc atcattcaac gtgcttataa   5040
aaattaccgc ttgaggcgaa atgacaaaaa tacatcagat attcatatga tagatggtga   5100
cagagatgtt catgctacta aagaaggtgc ctattttgac aaagctaagg aaaagtcacc   5160
tattcaaagc cagatctaat accacttacc acctcttttc atatttcttc acatatctga   5220
aaaatgttga aagcctaagc caggaataaa agaaaagtag agataataat cagttcttta   5280
caaccgatgg taattaagct tgtattcaca agacttcatg ccaaattcac tttttagcat   5340
tatatctaac aaatcaagag aatccttaat attgctgcag tgagtttaaa gtgggttaaa   5400
gtggccattt gacaatctca tatttgtttt ctctacatgg cttatatgat gtgtgccttc   5460
tagggaatga agggaagtgg tgatagagat cagcagcagc aggggctttc ttttatattt   5520
tatgtataat ttaatgggct ttaagtcacc actattaaga cttacaaata agcaaatact   5580
ttcctgatgt gggatggtga aatgctaatg gccattaaat cataaacttg cctagacaaa   5640
agccaattgg aagaagggag agagcagttc tttagaaagt gcctttgaga tcaacctcag   5700
agattcttgg gctgattaaa actgcatttg aaaaagattg gttgaagctc tgtgtttatt   5760
tttgtatgtt cttgttttca tttggaactg ggaatgaata ggatttcatt gtgctcaagc   5820
tcctggtttc tcatctctgg atagtttcac ctaagctctg gctcttaagc aggacagatt   5880
cgtaaaacaa gaagcataaa ggagaggtat agcctttttt tttttttttt ttttcatttt   5940
cttctcattt acacctattt ttttaaaaag tatacattta ctaaaatgat gtaataaata   6000
acatgttaat agactcaagc tttaccttat gaaattgatg tatttttacc agttatttct   6060
aatgtaacat tgaatatata agatctgaca aatgtatgtt taaacatgaa ttagaagagt   6120
tgagaactac cattatgtat agggattctc atagtgtctt ggcccttaat tggaaagttg   6180
tggcaacttt aaagtacttt ttactgtatg ttataattct ttataactta gagagagaca   6240
atggtcactc aaactatgag aactatgaat taggagataa aagtttaaat ttgttgttgt   6300
tttataacag tatgtacaag ttagttttcc cttatatatt tacgttttca agttttttaa   6360
tctcatcata tacatccata ctctataaaa tgttttatat tcaaagaact gtaaaatcct   6420
aaacattagt tttcactatt gaaattgttt tttaaagata ggcataaata gttgtcctta   6480
gacttattca tacaaatata gtcatttact tctatgtagt ttgagattct gagagttatt   6540
ccaactttat gaagattgat ttcaatgtgc ctgctaagtc ctaaaagatt cagaaagaaa   6600
atttatatat tattgattta aatatcatcc tttaaatatg ttgtataaca ttcaatatag   6660
tttatgtatc agtgattgta ttttattctg aatgcatgat ctcaagcctt aactactata   6720
atctttttct gcccctcaga aattgaataa cctaaccaag atgcctttag ggatgccct   6780
aagtaaatgt aatttcagat ttcagggttt tttttttttc ctctctaagt gttccttccc   6840
```

```
tttcttctcc tgctctccat catgttatgg agaccagtga ggaaccagtg ttaacttggt   6900

gacaatgtga cagctggtgc tttatctaag ctccgttttc tatttcttgg gaatgcttta   6960

ttgtggaaac tgcttcagat acttaaattg aatcataact tgcttctgta aattgcgtaa   7020

agacaacaaa ctgattttag tttgaaaagt ttatctttta cttgtaaacc ttgtttgcca   7080

gttaccttcc gaaagctgtg taaagagtta tttttaacaa agtcttaaca atatatgtta   7140

ctttttagat actatagaaa ataataaata taacctgtaa accaca                 7186


<210> SEQ ID NO 7
<211> LENGTH: 7215
<212> TYPE: DNA
<213> ORGANISM: Homo sapiens

<400> SEQUENCE: 7

gagcgctcca agatggcgcc caccgcagtc ccgcccgccg catcctcggc gcctttgcag     60

tccggccgcg cctcccgggc cccgcgttag ggccgccgct gcctccctcg ccgccgccgc    120

tgccagctga cctgtcctgg acgcagcata actaacgaag ctgctgcagg atgagaagat    180

ggcagcgcgg ctgcttgcac caccaggccc tgatagtttc aagcctttca cccctgagtc    240

actggcaaac attgagaggc gcattgctga gagcaagctc aagaaaccac caaaggccga    300

tggcagtcat cgggaggacg atgaggacag caagcccaag ccaaacagcg acctggaagc    360

agggaagagt ttgcctttca tctacgggga catcccccaa ggcctggttg cagttcccct    420

ggaggacttt gacccatact atttgacgca gaaaaccttt gtagtattaa acagagggaa    480

aactctcttc agatttagtg ccacgcctgc cttgtacatt ttaagtcctt ttaacctgat    540

aagaagaata gctattaaaa ttttgataca ttcagtattt agcatgatca ttatgtgcac    600

tattttgacc aactgtgtat tcatgacttt tagtaaccct cctgactggt cgaagaatgt    660

ggagtacacg ttcacaggga tttatacatt tgaatcacta gtgaaaatca ttgcaagagg    720

tttctgcata gatggcttta cctttttacg ggacccatgg aactggttag atttcagtgt    780

catcatgatg gcgtatataa cagagtttgt aaacctaggc aatgtttcag ctctacgcac    840

tttcagggta ctgagggctt tgaaaactat ttcggtaatc ccaggcctga agacaattgt    900

gggtgccctg attcagtctg tgaagaaact gtcagatgtg atgatcctga cagtgttctg    960

cctgagtgtt tttgccttga tcggactgca gctgttcatg ggaaccttc gaaacaagtg   1020

tgttgtgtgg cccataaact tcaacgagag ctatcttgaa aatggcacca aaggctttga   1080

ttgggaagag tatatcaaca ataaaacaaa tttctacaca gttcctggca tgctggaacc   1140

tttactctgt gggaacagtt ctgatgctgg gcaatgccca gagggatacc agtgtatgaa   1200

agcaggaagg aaccccaact atggttacac aagttttgac acttttagct gggccttctt   1260

ggcattattt cgccttatga cccaggacta ttgggaaaac ttgtatcaat tgactttacg   1320

agcagccggg aaaacataca tgatcttctt cgtcttggtc atctttgtgg gttctttcta   1380

tctggtgaac ttgatcttgg ctgtggtggc catggcttat gaagaacaga atcaggcaac   1440

actggaggag gcagaacaaa aagaggctga atttaaagca atgttggagc aacttaagaa   1500

gcaacaggaa gaggcacagg ctgctgcgat ggccacttca gcaggaactg tctcagaaga   1560

tgccatagag gaagaaggtg aagaaggagg gggctcccct cggagctctt ctgaaatctc   1620

taaactcagc tcaaagagtg caaaggaaag acgtaacagg agaaagaaga ggaagcaaaa   1680

ggaactctct gaaggagagg agaaagggga tcccgagaag gtgtttaagt cagagtcaga   1740

agatggcatg agaaggaagg cctttcggct gccagacaac agaataggga ggaaattttc   1800
```

```
catcatgaat cagtcactgc tcagcatccc aggctcgccc ttcctctccc gccacaacag   1860
caagagcagc atcttcagtt tcaggggacc tgggcggttc cgagacccgg gctccgagaa   1920
tgagttcgcg gatgacgagc acagcacggt ggaggagagc gagggccgcc gggactccct   1980
cttcatcccc atccgggccc gcgagcgccg gagcagctac agcggctaca gcggctacag   2040
ccagggcagc cgctcctcgc gcatcttccc cagcctgcgg cgcagcgtga agcgcaacag   2100
cacggtggac tgcaacggcg tggtgtccct catcggcggc cccggctccc acatcggcgg   2160
gcgtctcctg ccagaggcta caactgaggt ggaaattaag aagaaaggcc ctggatctct   2220
tttagtttcc atggaccaat tagcctccta cgggcggaag gacagaatca acagtataat   2280
gagtgttgtt acaaatacac tagtagaaga actggaagag tctcagagaa agtgcccgcc   2340
atgctggtat aaatttgcca acactttcct catctgggag tgccacccct actggataaa   2400
actgaaagag attgtgaact tgatagttat ggacccttt gtggatttag ccatcaccat   2460
ctgcatcgtc ctgaatacac tgtttatggc aatggagcac catcctatga caccacaatt   2520
tgaacatgtc ttggctgtag gaaatctggt tttcactgga attttcacag cggaaatgtt   2580
cctgaagctc atagccatgg atccctacta ttatttccaa gaaggttgga acatttttga   2640
cggatttatt gtctccctca gtttaatgga actgagtcta gcagacgtgg aggggctttc   2700
agtgctgcga tctttccgat tgctccgagt cttcaaattg gccaaatcct ggcccaccct   2760
gaacatgcta atcaagatta ttggaaattc agtgggtgcc ctgggcaacc tgacactggt   2820
gctggccatt attgtcttca tctttgccgt ggtggggatg caactctttg gaaaaagcta   2880
caaagagtgt gtctgcaaga tcaaccagga ctgtgaactc cctcgctggc atatgcatga   2940
ctttttccat tccttcctca ttgtctttcg agtgttgtgc ggggagtgga ttgagaccat   3000
gtgggactgc atggaagtgg caggccaggc catgtgcctc attgtcttta tgatggtcat   3060
ggtgattggc aacttggtgg tgctgaacct gtttctggcc ttgctcctga gctccttcag   3120
tgcagacaac ctggctgcca cagatgacga tggggaaatg aacaacctcc agatctcagt   3180
gatccgtatc aagaagggtg tggcctggac caaactaaag gtgcacgcct tcatgcaggc   3240
ccactttaag cagcgtgagg ctgatgaggt gaagcctctg gatgagttgt atgaaaagaa   3300
ggccaactgt atcgccaatc acaccggtgc agacatccac cggaatggtg acttccagaa   3360
gaatggcaat ggcacaacca gcggcattgg cagcagcgtg gagaagtaca tcattgatga   3420
ggaccacatg tccttcatca acaaccccaa cttgactgta cgggtaccca ttgctgtggg   3480
cgagtctgac tttgagaacc tcaacacaga ggatgttagc agcgagtcgg atcctgaagg   3540
cagcaaagat aaactagatg acaccagctc ctctgaagga agcaccattg atatcaaacc   3600
agaagtagaa gaggtccctg tggaacagcc tgaggaatac ttggatccag atgcctgctt   3660
cacagaaggt tgtgtccagc ggttcaagtg ctgccaggtc aacatcgagg aagggctagg   3720
caagtcttgg tggatcctgc ggaaaacctg cttcctcatc gtggagcaca actggtttga   3780
gaccttcatc atcttcatga ttctgctgag cagtggcgcc ctggccttcg aggacatcta   3840
cattgagcag agaaagacca tccgcaccat cctggaatat gctgacaaag tcttcaccta   3900
tatcttcatc ctggagatgt tgctcaagtg gacagcctat ggcttcgtca agttcttcac   3960
caatgcctgg tgttggctgg acttcctcat tgtggctgtc tctttagtca gccttatagc   4020
taatgccctg ggctactcgg aactaggtgc cataaagtcc cttaggaccc taagagcttt   4080
gagaccctta agagccttat cacgatttga agggatgagg gtggtggtga atgccttggt   4140
```

```
gggcgccatc ccctccatca tgaatgtgct gctggtgtgt ctcatcttct ggctgatttt   4200
cagcatcatg ggagttaact tgtttgcggg aaagtaccac tactgcttta atgagacttc   4260
tgaaatccga tttgaaattg aagatgtcaa caataaaact gaatgtgaaa agcttatgga   4320
ggggaacaat acagagatca gatggaagaa cgtgaagatc aactttgaca atgttggggc   4380
aggatacctg gcccttcttc aagtagcaac cttcaaaggc tggatggaca tcatgtatgc   4440
agctgtagat tcccggaagc ctgatgagca gcctaagtat gaggacaata tctacatgta   4500
catctatttt gtcatcttca tcatcttcgg ctccttcttc accctgaacc tgttcattgg   4560
tgtcatcatt gataacttca atcaacaaaa gaaaaagttc ggaggtcagg acatcttcat   4620
gaccgaagaa cagaagaagt actacaatgc catgaaaaag ctgggctcaa agaagccaca   4680
gaaacctatt ccccgcccct tgaacaaaat ccaaggaatc gtctttgatt ttgtcactca   4740
gcaagccttt gacattgtta tcatgatgct catctgcctt aacatggtga caatgatggt   4800
ggagacagac actcaaagca agcagatgga gaacatcctc tactggatta acctggtgtt   4860
tgttatcttc ttcacctgtg agtgtgtgct caaaatgttt gcgttgaggc actactactt   4920
caccattggc tggaacatct tcgacttcgt ggtagtcatc ctctccattg tgggaatgtt   4980
cctggcagat ataattgaga aatactttgt ttccccaacc ctattccgag tcatccgatt   5040
ggcccgtatt gggcgcatct tgcgtctgat caaaggcgcc aaagggattc gtaccctgct   5100
ctttgcctta atgatgtcct tgcctgccct gttcaacatc ggccttctgc tcttcctggt   5160
catgttcatc ttctccattt ttgggatgtc caattttgca tatgtgaagc acgaggctgg   5220
tatcgatgac atgttcaact ttgagacatt tggcaacagc atgatctgcc tgtttcaaat   5280
cacaacctca gctggttggg atggcctgct gctgcccatc ctaaaccgcc cccctgactg   5340
cagcctagat aaggaacacc cagggagtgg ctttaaggga gattgtggga acccctcagt   5400
gggcatcttc ttctttgtaa gctacatcat catctctttc ctaattgtcg tgaacatgta   5460
cattgccatc atcctggaga acttcagtgt agccacagag gaaagtgcag accctctgag   5520
tgaggatgac tttgagacct tctatgagat ctgggagaag ttcgaccccg atgccaccca   5580
gttcattgag tactgtaagc tggcagactt tgcagatgcc ttggagcatc ctctccgagt   5640
gcccaagccc aataccattg agctcatcgc tatggatctg ccaatggtga gcggggatcg   5700
catccactgc ttggacatcc tttttgcctt caccaagcgg gtcctgggag atagcgggga   5760
gttggacatc ctgcggcagc agatggaaga gcggttcgtg gcatccaatc cttccaaagt   5820
gtcttacgag ccaatcacaa ccacactgcg tcgcaagcag gaggaggtat ctgcagtggt   5880
cctgcagcgt gcctaccggg gacatttggc aaggcggggc ttcatctgca aaaagacaac   5940
ttctaataag ctggagaatg gaggcacaca ccgggagaaa aaagagagca ccccatctac   6000
agcctccctc ccgtcctatg acagtgtaac taaacctgaa aaggagaaac agcagcgggc   6060
agaggaagga agaagggaaa gagccaaaag acaaaaagag gtcagagaat ccaagtgtta   6120
gaggagaaca aaaattcagt attatacaga tctaaaactc gcaagtgaaa gattgtttac   6180
aaacttcctg aatattatca atgcagaaca gctgtggaga ctctaacctg aagatctata   6240
ccaaacgtcg tctgcttacc acgtaacaca gctgcatctt gagcagtgac ctgccaaggg   6300
caaaggaccc cgctccctag acttacagat tttctaatgc ttgggcaggt ggttactgca   6360
tgttccacat cagtcaatgc aacttaggac aaaactaacc agatacagaa acagaagaga   6420
ggctgccggg accagcatat ttccgttgca gccaaatgga ttttattttt tcattttatt   6480
gattctcaga agcagaaagc atcactttaa aagttcgttt gttcatgcaa actatatttg   6540
```

cattcttaca ttagttaagc taagcagcaa aaagaaaaca cacacacaca ctcacattta 6600
gcccatgtca tttaattgtc agtttctttg acataaagcg catcttctcc acatgggctt 6660
cacgtggttt ggagatgggt gggggaaaac aatcaggttt cttcaggctg aggaggactt 6720
gctcaggccg attccaaaca ttgtgctcgt tcaatgcgta gaaatgattt gcatgatggc 6780
atgccgtgat cagaagtcat gcatgagatc catacaccac aggacactac taatctagtc 6840
ccttgcactg ggtcagcctt tggacaggac ccagccctgc accgttcact gtatttggag 6900
aaaatggtaa gagttccata ccggctacaa ttctttgagt tcttaaaagt ccttcataca 6960
ccttctgggt agggaaacaa ccaactaatt gactaacacc accaacaaca aaaaacaaac 7020
ccaatccaac aagcagatgg atccgttgcg tgtatatgtt taacagacat ctctaacata 7080
cagccattgt tgcacatttt gcaagatgaa ctatttaatg ctgctctgtg tccagtacat 7140
gggggagact ttgatcccaa atggcttgta ctatttatgt cactgtaaaa ccaaatccta 7200
gggctaaaaa aaaaa 7215

<210> SEQ ID NO 8
<211> LENGTH: 9771
<212> TYPE: DNA
<213> ORGANISM: Homo sapiens

<400> SEQUENCE: 8
cggggctgct acctccacgg gcgcgccctg gcaggagggg cgcagtctgc ttgcaggcgg 60
tcgccagcgc tccagcggcg gctgtcggct ttccaattcc gccagctcgg ctgaggctgg 120
gctagcctgg gtgccagtgg ctgctagcgg caggcgtccc ctgagcaaca ggagcccaga 180
gaaaaagaag cagccctgag agagcgccgg ggaaggagag gcccgcgccc tctcctggag 240
ccagattctg caggtgcact gggtggggat gatcggcggg ctaggttgca agcctcttat 300
gtgaggagct gaagaggaat taaaatatac aggatgaaaa gatggcaatg ttgcctcccc 360
caggacctca gagctttgtc catttcacaa aacagtctct tgccctcatt gaacaacgca 420
ttgctgaaag aaaatcaaag gaacccaaag aagaaaagaa agatgatgat gaagaagccc 480
caaagccaag cagtgacttg gaagctggca aacagctgcc cttcatctat ggggacattc 540
ctcccggcat ggtgtcagag cccctggagg acttggaccc ctactatgca gacaaaaaga 600
ctttcatagt attgaacaaa gggaaaacaa tcttccgttt caatgccaca cctgctttat 660
atatgctttc tcctttcagt cctctaagaa gaatatctat taagatttta gtacactcct 720
tattcagcat gctcatcatg tgcactattc tgacaaactg catatttatg accatgaata 780
acccaccgga ctggaccaaa aatgtcgagt acacttttac tggaatatat acttttgaat 840
cacttgtaaa aatccttgca agaggcttct gtgtaggaga attcactttt cttcgtgacc 900
cgtggaactg gctggatttt gtcgtcattg tttttgcgta tttaacagaa tttgtaaacc 960
taggcaatgt ttcagctctt cgaactttca gagtattgag agctttgaaa actatttctg 1020
taatcccagg cctgaagaca attgtagggg ctttgatcca gtcagtgaag aagctttctg 1080
atgtcatgat cctgactgtg ttctgtctga gtgtgtttgc actaattgga ctacagctgt 1140
tcatgggaaa cctgaagcat aaatgttttc gaaattcact tgaaaataat gaaacattag 1200
aaagcataat gaatacccta gagagtgaag aagactttag aaaatatttt tattacttgg 1260
aaggatccaa agatgctctc ctttgtggtt tcagcacaga ttcaggtcag tgtccagagg 1320
ggtacacctg tgtgaaaatt ggcagaaacc ctgattatgg ctacacgagc tttgacactt 1380

```
tcagctgggc cttcttagcc ttgtttaggc taatgaccca agattactgg gaaaaccttt   1440
accaacagac gctgcgtgct gctggcaaaa cctacatgat cttctttgtc gtagtgattt   1500
tcctgggctc cttttatcta ataaacttga tcctggctgt ggttgccatg gcatatgaag   1560
aacagaacca ggcaaacatt gaagaagcta aacagaaaga attagaattt caacagatgt   1620
tagaccgtct taaaaaagag caagaagaag ctgaggcaat tgcagcggca gcggctgaat   1680
atacaagtat taggagaagc agaattatgg gcctctcaga gagttcttct gaaacatcca   1740
aactgagctc taaaagtgct aaagaaagaa gaaacagaag aaagaaaaag aatcaaaaga   1800
agctctccag tggagaggaa aagggagatg ctgagaaatt gtcgaaatca gaatcagagg   1860
acagcatcag aagaaaaagt ttccaccttg gtgtcgaagg gcataggcga gcacatgaaa   1920
agaggttgtc taccccccaat cagtcaccac tcagcattcg tggctccttg ttttctgcaa   1980
ggcgaagcag cagaacaagt ctttttagtt tcaaaggcag aggaagagat ataggatctg   2040
agactgaatt tgccgatgat gagcacagca tttttggaga caatgagagc agaaggggct   2100
cactgtttgt gccccacaga ccccaggagc gacgcagcag taacatcagc caagccagta   2160
ggtccccacc aatgctgccg gtgaacggga aaatgcacag tgctgtggac tgcaacggtg   2220
tggtctccct ggttgatgga cgctcagccc tcatgctccc caatggacag cttctgccag   2280
agggcacgac caatcaaata cacaagaaaa ggcgttgtag ttcctatctc ctttcagagg   2340
atatgctgaa tgatcccaac ctcagacaga gagcaatgag tagagcaagc atattaacaa   2400
acactgtgga agaacttgaa gagtccagac aaaaatgtcc accttggtgg tacagatttg   2460
cacacaaatt cttgatctgg aattgctctc catattggat aaaattcaaa aagtgtatct   2520
attttattgt aatggatcct tttgtagatc ttgcaattac catttgcata gttttaaaca   2580
cattatttat ggctatggaa caccacccaa tgactgagga attcaaaaat gtacttgcta   2640
taggaaattt ggtctttact ggaatctttg cagctgaaat ggtattaaaa ctgattgcca   2700
tggatccata tgagtatttc caagtaggct ggaatatttt tgacagcctt attgtgactt   2760
taagtttagt ggagctcttt ctagcagatg tggaaggatt gtcagttctg cgatcattca   2820
gactgctccg agtcttcaag ttggcaaaat cctggccaac attgaacatg ctgattaaga   2880
tcattggtaa ctcagtaggg gctctaggta acctcacctt agtgttggcc atcatcgtct   2940
tcatttttgc tgtggtcggc atgcagctct ttggtaagag ctacaaagaa tgtgtctgca   3000
agatcaatga tgactgtacg ctcccacggt ggcacatgaa cgacttcttc cactccttcc   3060
tgattgtgtt ccgcgtgctg tgtggagagt ggatagagac catgtgggac tgtatggagg   3120
tcgctggtca agctatgtgc cttattgttt acatgatggt catggtcatt ggaaacctgg   3180
tggtcctaaa cctatttctg gccttattat tgagctcatt tagttcagac aatcttacag   3240
caattgaaga agaccctgat gcaaacaacc tccagattgc agtgactaga attaaaaagg   3300
gaataaatta tgtgaaacaa accttacgtg aatttattct aaaagcattt tccaaaaagc   3360
caaagatttc cagggagata agacaagcag aagatctgaa tactaagaag gaaaactata   3420
tttctaacca tacacttgct gaaatgagca aaggtcacaa tttcctcaag gaaaaagata   3480
aaatcagtgg ttttggaagc agcgtggaca aacacttgat ggaagacagt gatggtcaat   3540
catttattca caatcccagc ctcacagtga cagtgccaat tgcacctggg gaatccgatt   3600
tggaaaatat gaatgctgag gaacttagca gtgattcgga tagtgaatac agcaaagtga   3660
gattaaaccg gtcaagctcc tcagagtgca gcacagttga taacccctttg cctggagaag   3720
gagaagaagc agaggctgaa cctatgaatt ccgatgagcc agaggcctgt ttcacagatg   3780
```

```
gttgtgtacg gaggttctca tgctgccaag ttaacataga gtcagggaaa ggaaaaatct   3840
ggtggaacat caggaaaacc tgctacaaga ttgttgaaca cagttggttt gaaagcttca   3900
ttgtcctcat gatcctgctc agcagtggtg ccctggcttt tgaagatatt tatattgaaa   3960
ggaaaaagac cattaagatt atcctggagt atgcagacaa gatcttcact tacatcttca   4020
ttctggaaat gcttctaaaa tggatagcat atggttataa aacatatttc accaatgcct   4080
ggtgttggct ggatttccta attgttgatg tttctttggt tactttagtg gcaaacactc   4140
ttggctactc agatcttggc cccattaaat cccttcggac actgagagct ttaagacctc   4200
taagagcctt atctagattt gaaggaatga gggtcgttgt gaatgcactc ataggagcaa   4260
ttccttccat catgaatgtg ctacttgtgt gtcttatatt ctggctgata ttcagcatca   4320
tgggagtaaa tttgtttgct ggcaagttct atgagtgtat taacaccaca gatgggtcac   4380
ggtttcctgc aagtcaagtt ccaaatcgtt ccgaatgttt tgcccttatg aatgttagtc   4440
aaaatgtgcg atggaaaaac ctgaaagtga actttgataa tgtcggactt ggttacctat   4500
ctctgcttca agttgcaact tttaagggat ggacgattat tatgtatgca gcagtggatt   4560
ctgttaatgt agacaagcag cccaaatatg aatatagcct ctacatgtat atttattttg   4620
tcgtctttat catctttggg tcattcttca ctttgaactt gttcattggt gtcatcatag   4680
ataatttcaa ccaacagaaa aagaagcttg gaggtcaaga catctttatg acagaagaac   4740
agaagaaata ctataatgca atgaaaaagc tggggtccaa gaagccacaa aagccaattc   4800
ctcgaccagg gaacaaaatc caaggatgta tatttgacct agtgacaaat caagcctttg   4860
atattagtat catggttctt atctgtctca acatggtaac catgatggta gaaaaggagg   4920
gtcaaagtca acatatgact gaagttttat attggataaa tgtggttttt ataatccttt   4980
tcactggaga atgtgtgcta aaactgatct ccctcagaca ctactacttc actgtaggat   5040
ggaatatttt tgattttgtg gttgtgatta tctccattgt aggtatgttt ctagctgatt   5100
tgattgaaac gtattttgtg tcccctaccc tgttccgagt gatccgtctt gccaggattg   5160
gccgaatcct acgtctagtc aaaggagcaa aggggatccg cacgctgctc tttgctttga   5220
tgatgtccct tcctgcgttg tttaacatcg gcctcctgct cttcctggtc atgttcatct   5280
acgccatctt tggaatgtcc aactttgcct atgttaaaaa ggaagatgga attaatgaca   5340
tgttcaattt tgagaccttt ggcaacagta tgatttgcct gttccaaatt acaacctctg   5400
ctggctggga tggattgcta gcacctattc ttaacagtaa gccacccgac tgtgacccaa   5460
aaaaagttca tcctggaagt tcagttgaag gagactgtgg taacccatct gttggaatat   5520
tctactttgt tagttatatc atcatatcct tcctggttgt ggtgaacatg tacattgcag   5580
tcatactgga gaattttagt gttgccactg aagaaagtac tgaacctctg agtgaggatg   5640
actttgagat gttctatgag gtttgggaga agtttgatcc cgatgcgacc cagtttatag   5700
agttctctaa actctctgat tttgcagctg ccctggatcc tcctcttctc atagcaaaac   5760
ccaacaaagt ccagctcatt gccatggatc tgcccatggt tagtggtgac cggatccatt   5820
gtcttgacat cttatttgct tttacaaagc gtgttttggg tgagagtggg gagatggatt   5880
ctcttcgttc acagatggaa gaaaggttca tgtctgcaaa tccttccaaa gtgtcctatg   5940
aacccatcac aaccacacta aaacggaaac aagaggatgt gtctgctact gtcattcagc   6000
gtgcttatag acgttaccgc ttaaggcaaa atgtcaaaaa tatatcaagt atatacataa   6060
aagatggaga cagagatgat gatttactca ataaaaaaga tatggctttt gataatgtta   6120
```

```
atgagaactc aagtccagaa aaaacagatg ccacttcatc caccacctct ccaccttcat   6180
atgatagtgt aacaaagcca gacaaagaga aatatgaaca agacagaaca gaaaaggaag   6240
acaaagggaa agacagcaag gaaagcaaaa aatagagctt catttttgat atattgttta   6300
cagcctgtga aagtgattta tttgtgttaa taaaactctt ttgaggaagt ctatgccaaa   6360
atccttttta tcaaaatatt ctcgaaggca gtgcagtcac taactctgat ttcctaagaa   6420
aggtgggcag cattagcaga tggttatttt tgcactgatg attctttaag aatcgtaaga   6480
gaactctgta ggaattattg attatagcat acaaaagtga ttcagttttt tggtttttaa   6540
taaatcagaa gaccatgtag aaaactttta catctgcctt gtcatctttt cacaggattg   6600
taattagtct tgtttcccat gtaaataaac aacacacgca tacagaaaaa tctattattt   6660
atctattatt tggaaatcaa caaaagtatt tgccttggct ttgcaatgaa atgcttgata   6720
gaagtaatgg acattagtta tgaatgttta gttaaaatgc attattaggg agcttgactt   6780
tttatcaatg tacagaggtt attctatatt ttgaggtgct taaatttatt ctacattgca   6840
tcagaaccaa tttatatgtg cctataaaat gccatgggat taaaaatata tgtaggctat   6900
tcatttctac aaatgttttt cattcatctt gactcacatg ccaacaagga taagacttac   6960
ctttagagta ttgtgtttca tagcctttct tctttcatat ccctttttgt tcatagaata   7020
accacagaac ttgaaaaatt attctaagta catattacac tcctcaaaaa aaacaaagat   7080
aactgagaaa aaagttattg acagaagttc tatttgctat tatttacata gcctaacatt   7140
tgactgtgct gcccaaaata ctgataatag tctcttaaac tcttttgtca aattttcctg   7200
ctttcttatg cagtattgtt tagtcatcct ttcgctgtaa gcaaagttga tgaaatcctt   7260
cctgatatgc agttagttgt ttgaccacgg tacatacttg agcagataat aacttgggca   7320
cagtatttat tgcatcactt gtatacaatc ccgtgtttgg caagctttca aatcatgtaa   7380
tatgacagac tttacacaga tatgtgttta gtatgaataa aaaagcattg aaatagggat   7440
tcttgccaac ttgctctctt gccaccaact tactttccta aattatggaa gtaatctttt   7500
ttggatatac ttcaatgtat acaatgagga agatgtcacc ttctccttaa aattctatga   7560
tgtgaaatat attttgcctc aatcaacaca gtaccatggg cttctaattt atcaagcaca   7620
tattcatttt gcattagctg tagacatcta gttttttgaa aacacctatt aatagtaatt   7680
tgaaaagaaa taaccataat gctttttttc gtgagtttat ttcaggaata tgagatcttt   7740
cttctataaa gttattcatg cacaggcaaa aattgagcta cacaggtaga atgtagtttt   7800
acttagaaga tttttgtggg aggttttgaa gcaaatatat aaaacaactt tcactaattt   7860
gctttccata tttaaaaaat aataaattac atttatataa taaatgttta aagcacatat   7920
tttttgttgt tctggcaatt taaaaagaaa gaggatttaa acgtacctat agaaacaaag   7980
atttatggtt aaagaatgag atcagaagtc tagaatgttt ttaaattgtg atatatttta   8040
caacatccgt tattactttg agacatttgt cctaatctac gtataaaact caatctaggg   8100
ctaaagattc tttataccat cttaggttca ttcatcttag gctatttgaa ccactttttta   8160
atttaatatg aaagacacca tgcagtgttt tccgagacta catagatcat tttatcacat   8220
acctaccaag cctgttggaa ataggttttg ataatttaag tagggaccta tacaaaatat   8280
attacattta tcagattttt aaatacattc aattaagaat ttaacatcac cttaaatttg   8340
aattcaatct accgttattt caaactcaca aatataactg cattatgaat acttacataa   8400
tgtagtaaga caagatgttt gacaggttcg tgtgtaattt tctattaatg tttttacatt   8460
gccttgtttt tatgtaaaat aaaaaaatatg ggcaactggt ttgttaacaa cacaatttct   8520
```

```
tcttagcatt tcaaaaatat atataaagtt gttctttttc ctatttcatg aactatgttt   8580

tttttaaaa taacatggtt aagttttata tatatttacg tttgtttcag gaatgtctac   8640

ttgtgacttt ttatcaatta aaaataatat ttggaagaaa gagcttatta agtataagct   8700

tgaagtaaaa ttagacctct ctttccatgt agattactgt ttgtactgat ggtttcaccc   8760

ttcagaaggc actgtcatat taatatttaa attttataat cgctgaactt attacaccca   8820

acaatacaga aaggcagtta cactgaagaa cttaacttag aataaaatgg aagcaaacag   8880

gttttctaaa aactttttta agtgaccagg tctcgctctg tcacccaggc tagagtgcaa   8940

tggcatgatc atagctctct gcagcctcaa ctctgggctc aagcaaccct cctgcctcag   9000

cctcccaagt agctaagact acaggtacat gccaccatgc ctggctaata tttaaatttt   9060

tgtagataag gggtcttgct atgttgccca ggctagtctc aaactcctgg cttcaagtgt   9120

tcctactgtc atgacctgcc aacatgctgg ggttacaggc atgagccacc atgccccaaa   9180

caggtttgaa cacaaatctt tcggatgaaa attagagaac ctaattttag ctttttgata   9240

gttacctagt ttgcaaaaga tttgggtgac ttgtgagctg tttttaaatg ctgattgttg   9300

aacatcacaa cccaaaatac ttagcatgat tttatagagt tttgatagct ttattaaaaa   9360

gagtgaaaat aaaatgcata tgtaaataaa gcagttctaa atagctattt cagagaaatg   9420

ttaatagaag tgctgaaaga agggccaact aaattaggat ggccagggaa ttggcctggg   9480

tttaggacct atgtatgaag gccaccaatt ttttaaaaat atctgtggtt tattatgtta   9540

ttatcttctt gaggaaaaca atcaagaatt gcttcatgaa aataaataaa tagccatgaa   9600

tatcataaag ctgtttacat aggattcttt acaaatttca tagatctatg aatgctcaaa   9660

atgtttgagt ttgccataaa ttatattgta gttatattgt agttatactt gagactgaca   9720

cattgtaata taatctaaga ataaaagtta tacaaaataa aaaaaaaaaa a            9771
```

<210> SEQ ID NO 9
<211> LENGTH: 5874
<212> TYPE: DNA
<213> ORGANISM: Homo sapiens

<400> SEQUENCE: 9

```
atggaattcc ccattggatc cctcgaaact aacaacttcc gtcgctttac tccggagtca     60

ctggtggaga tagagaagca aattgctgcc aagcagggaa caaagaaagc cagagagaag    120

catagggagc agaaggacca agaagagaag cctcggcccc agctggactt gaaagcctgc    180

aaccagctgc ccaagttcta tggtgagctc ccagcagaac tgatcgggga gcccctggag    240

gatctagatc cgttctacag cacacaccgg acatttatgg tgctgaacaa agggaggacc    300

atttcccggt ttagtgccac tcgggccctg tggctattca gtcctttcaa cctgatcaga    360

agaacggcca tcaaagtgtc tgtccactcg tggttcagtt tatttattac ggtcactatt    420

ttggttaatt gtgtgtgcat gacccgaact gaccttccag agaaaattga atatgtcttc    480

actgtcattt acacctttga agccttgata aagatactgg caagaggatt ttgtctaaat    540

gagttcacgt acctgagaga tccttggaac tggctggatt ttagcgtcat taccctggca    600

tatgttggca cagcaataga tctccgtggg atctcaggcc tgcggacatt cagagttctt    660

agagcattaa aaacagtttc tgtgatccca ggcctgaagg tcattgtggg ggccctgatt    720

cactcagtga agaaactggc tgatgtgacc atcctcacca tcttctgcct aagtgttttt    780

gccttggtgg ggctgcaact cttcaagggc aacctcaaaa ataaatgtgt caagaatgac    840
```

```
atggctgtca atgagacaac caactactca tctcacagaa aaccagatat ctacataaat    900
aagcgaggca cttctgaccc cttactgtgt ggcaatggat ctgactcagg ccactgccct    960
gatggttata tctgccttaa aacttctgac aacccggatt ttaactacac cagctttgat   1020
tcctttgctt gggctttcct ctcactgttc cgcctcatga cacaggattc ctgggaacgc   1080
ctctaccagc agaccctgag gacttctggg aaaatctata tgatcttttt tgtgctcgta   1140
atcttcctgg gatctttcta cctggtcaac ttgatcttgg ctgtagtcac catggcgtat   1200
gaggagcaga accaggcaac cactgatgaa attgaagcaa aggagaagaa gttccaggag   1260
gccctcgaga tgctccggaa ggagcaggag gtgctagcag cactagggat tgacacaacc   1320
tctctccact cccacaatgg atcaccttta acctccaaaa atgccagtga gagaaggcat   1380
agaataaagc caagagtgtc agagggctcc acagaagaca acaaatcacc ccgctctgat   1440
ccttacaacc agcgcaggat gtcttttcta ggcctcgcct ctggaaaacg ccgggctagt   1500
catggcagtg tgttccattt ccggtcccct ggccgagata tctcactccc tgagggagtc   1560
acagatgatg gagtctttcc tggagaccac gaaagccatc ggggctctct gctgctgggt   1620
gggggtgctg gccagcaagg ccccctccct agaagccctc ttcctcaacc cagcaaccct   1680
gactccaggc atggagaaga tgaacaccaa ccgccgccca ctagtgagct tgcccctgga   1740
gctgtcgatg tctcggcatt cgatgcagga caaaagaaga ctttcttgtc agcagaatac   1800
ttagatgaac ctttccgggc ccaaagggca atgagtgttg tcagtatcat aacctccgtc   1860
cttgaggaac tcgaggagtc tgaacagaag tgcccaccct gcttgaccag cttgtctcag   1920
aagtatctga tctgggattg ctgccccatg tgggtgaagc tcaagacaat tctctttggg   1980
cttgtgacgg atccctttgc agagctcacc atcaccttgt gcatcgtggt gaacaccatc   2040
ttcatggcca tggagcacca tggcatgagc cctaccttcg aagccatgct ccagataggc   2100
aacatcgtct ttaccatatt ttttactgct gaaatggtct tcaaaatcat tgccttcgac   2160
ccatactatt atttccagaa gaagtggaat atctttgact gcatcatcgt cactgtgagt   2220
ctgctagagc tgggcgtggc caagaaggga agcctgtctg tgctgcggag cttccgcttg   2280
ctgcgcgtat tcaagctggc caaatcctgg cccaccttaa acacactcat caagatcatc   2340
ggaaactcag tgggggcact ggggaacctc accatcatcc tggccatcat tgtctttgtc   2400
tttgctctgg ttggcaagca gctcctaggg gaaaactacc gtaacaaccg aaaaaatatc   2460
tccgcgcccc atgaagactg gccccgctgg cacatgcacg acttcttcca ctctttcctc   2520
attgtcttcc gtatcctctg tggagagtgg attgagaaca tgtgggcctg catggaagtt   2580
ggccaaaaat ccatatgcct catccttttc ttgacggtga tggtgctagg gaacctggtg   2640
gtgcttaacc tgttcatcgc cctgctattg aactctttca gtgctgacaa cctcacagcc   2700
ccggaggacg atggggaggt gaacaacctg caggtggccc tggcacggat ccaggtcttt   2760
ggccatcgta ccaaacaggc tctttgcagc ttcttcagca ggtcctgccc attcccccag   2820
cccaaggcag agcctgagct ggtggtgaaa ctcccactct ccagctccaa ggctgagaac   2880
cacattgctg ccaacactgc caggggggagc tctggagggc tccaagctcc cagaggcccc   2940
agggatgagc acagtgactt catcgctaat ccgactgtgt gggtctctgt gcccattgct   3000
gagggtgaat ctgatcttga tgacttggag gatgatggtg gggaagatgc tcagagcttc   3060
cagcaggaag tgatccccaa aggacagcag gagcagctgc agcaagtcga gaggtgtggg   3120
gaccacctga cacccaggag cccaggcact ggaacatctt ctgaggacct ggctccatcc   3180
ctgggtgaga cgtggaaaga tgagtctgtt cctcaggtcc ctgctgaggg agtggacgac   3240
```

```
acaagctcct ctgagggcag cacggtggac tgcctagatc ctgaggaaat cctgaggaag   3300
atccctgagc tggcagatga cctggaagaa ccagatgact gcttcacaga aggatgcatt   3360
cgccactgtc cctgctgcaa actggatacc accaagagtc catgggatgt gggctggcag   3420
gtgcgcaaga cttgctaccg tatcgtggag cacagctggt ttgagagctt catcatcttc   3480
atgatcctgc tcagcagtgg atctctggcc tttgaagact attacctgga ccagaagccc   3540
acggtgaaag ctttgctgga gtacactgac agggtcttca cctttatctt tgtgttcgag   3600
atgctgctta agtgggtggc ctatggcttc aaaaagtact tcaccaatgc ctggtgctgg   3660
ctggacttcc tcattgtgaa tatctcactg ataagtctca cagcgaagat tctggaatat   3720
tctgaagtgg ctcccatcaa agcccttcga acccttcgcg ctctgcggcc actgcgggct   3780
ctttctcgat ttgaaggcat gcgggtggtg gtggatgccc tggtgggcgc catcccatcc   3840
atcatgaatg tcctcctcgt ctgcctcatc ttctggctca tcttcagcat catgggtgtg   3900
aacctcttcg cagggaagtt ttggaggtgc atcaactata ccgatggaga gttttccctt   3960
gtacctttgt cgattgtgaa taacaagtct gactgcaaga ttcaaaactc cactggcagc   4020
ttcttctggg tcaatgtgaa agtcaacttt gataatgttg caatgggtta ccttgcactt   4080
ctgcaggtgg caacctttaa aggctggatg gacattatgt atgcagctgt tgattcccgg   4140
gaggtcaaca tgcaacccaa gtgggaggac aacgtgtaca tgtatttgta ctttgtcatc   4200
ttcatcattt ttggaggctt cttcacactg aatctctttg ttggggtcat aattgacaac   4260
ttcaatcaac agaaaaaaaa gttagggggc caggacatct tcatgacaga ggagcagaag   4320
aaatactaca atgccatgaa gaagttgggc tccaagaagc cccagaagcc catcccacgg   4380
cccctgaaca agttccaggg ttttgtcttt gacatcgtga ccagacaagc ttttgacatc   4440
accatcatgg tcctcatctg cctcaacatg atcaccatga tggtggagac tgatgaccaa   4500
agtgaagaaa agacgaaaat tctgggcaaa atcaaccagt tctttgtggc cgtcttcaca   4560
ggcgaatgtg tcatgaagat gttcgctttg aggcagtact acttcacaaa tggctggaat   4620
gtgtttgact tcattgtggt ggttctctcc attgcgagcc tgatttttttc tgcaattctt   4680
aagtcacttc aaagttactt ctccccaacg ctcttcagag tcatccgcct ggcccgaatt   4740
ggccgcatcc tcagactgat ccgagcggcc aaggggatcc gcacactgct ctttgccctc   4800
atgatgtccc tgcctgccct cttcaacatc gggctgttgc tattccttgt catgttcatc   4860
tactctatct tcggtatgtc cagctttccc catgtgaggt gggaggctgg catcgacgac   4920
atgttcaact tccagacctt cgccaacagc atgctgtgcc tcttccagat taccacgtcg   4980
gccggctggg atggcctcct cagccccatc ctcaacacag ggccccccta ctgtgacccc   5040
aatctgccca acagcaatgg caccagaggg gactgtggga gcccagccgt aggcatcatc   5100
ttcttcacca cctacatcat catctccttc ctcatcatgg tcaacatgta cattgcagtg   5160
attctggaga acttcaatgt ggccacggag gagagcactg agcccctgag tgaggacgac   5220
tttgacatgt tctatgagac ctgggagaag tttgacccag aggccactca gtttattacc   5280
ttttctgctc tctcggactt tgcagacact ctctctggtc ccctgagaat cccaaaaccc   5340
aatcgaaata tactgatcca gatggacctg cctttggtcc ctggagataa gatccactgc   5400
ttggacatcc tttttgcttt caccaagaat gtcctaggag aatccgggga gttggattct   5460
ctgaaggcaa atatggagga gaagtttatg gcaactaatc tttcaaaatc atcctatgaa   5520
ccaatagcaa ccactctccg atggaagcaa gaagacattt cagccactgt cattcaaaag   5580
```

```
gcctatcgga gctatgtgct gcaccgctcc atggcactct ctaacacccc atgtgtgccc   5640
agagctgagg aggaggctgc atcactccca gatgaaggtt ttgttgcatt cacagcaaat   5700
gaaaattgtg tactcccaga caaatctgaa actgcttctg ccacatcatt cccaccgtcc   5760
tatgagagtg tcactagagg ccttagtgat agagtcaaca tgaggacatc tagctcaata   5820
caaaatgaag atgaagccac cagtatggag ctgattgccc ctgggcccta gtga         5874
```

<210> SEQ ID NO 10
<211> LENGTH: 6500
<212> TYPE: DNA
<213> ORGANISM: Homo sapiens

<400> SEQUENCE: 10

```
tcctgctata cccacagtgg tggtcatctc ttctgatctt cacagccaat cagctcccaa     60
ggcccctgac ctcagctcag cttttgtaga tccttatgac accatccttt aagactggaa    120
tcctagggca ggctgtttta ttcccgcctc ctgaggcctt tctgaggatc tgtggcttgt    180
ctctgtcctg agggtgaaga tggatgacag atgctaccca gtaatctttc cagatgagcg    240
gaatttccgc cccttcactt ccgactctct ggctgcaatt gagaagcgga ttgccatcca    300
aaaggagaaa aagaagtcta aagaccagac aggagaagta ccccagcctc ggcctcagct    360
tgacctaaag gcctccagga agttgcccaa gctctatggc gacattcctc gtgagctcat    420
aggaaagcct ctggaagact tggacccatt ctaccgaaat cataagacat ttatggtgtt    480
aaacagaaag aggacaatct accgcttcag tgccaagcat gccttgttca tttttgggcc    540
tttcaattca atcagaagtt tagccattag agtctcagtc cattcattgt tcagcatgtt    600
cattatcggc accgttatca tcaactgcgt gttcatggct acagggcctg ctaaaaacag    660
caacagtaac aatactgaca ttgcagagtg tgtcttcact gggatttata tttttgaagc    720
tttgattaaa atattggcaa gaggtttcat tctggatgag ttttctttcc ttcgagatcc    780
atggaactgg ctggactcca ttgtcattgg aatagcgatt gtgtcatata ttccaggaat    840
caccatcaaa ctattgcccc tgcgtacctt ccgtgtgttc agagctttga aagcaatttc    900
agtagtttca cgtctgaagg tcatcgtggg ggccttgcta cgctctgtga agaagctggt    960
caacgtgatt atcctcacct tcttttgcct cagcatcttt gccctggtag gtcagcagct   1020
cttcatggga agtctgaacc tgaaatgcat ctcgagggac tgtaaaaata tcagtaaccc   1080
ggaagcttat gaccattgct ttgaaaagaa agaaaattca cctgaattca aaatgtgtgg   1140
catctggatg ggtaacagtg cctgttccat acaatatgaa tgtaagcaca ccaaaattaa   1200
tcctgactat aattatacga attttgacaa ctttggctgg tcttttcttg ccatgttccg   1260
gctgatgacc caagattcct gggagaagct ttatcaacag accctgcgta ctactgggct   1320
ctactcagtc ttcttcttca ttgtggtcat tttcctgggc tccttctacc tgattaactt   1380
aaccctggct gttgttacca tggcatatga ggagcagaac aagaatgtag ctgcagagat   1440
agaggccaag gaaaagatgt ttcaggaagc ccagcagctg ttaaaggagg aaaaggaggc   1500
tctggttgcc atgggaattg acagaagttc acttacttcc cttgaaacat catattttac   1560
cccaaaaaag agaaagctct ttggtaataa gaaaaggaag tccttctttt tgagagagtc   1620
tgggaaagac cagcctcctg ggtcagattc tgatgaagat tgccaaaaaa agccacagct   1680
cctagagcaa accaaacgac tgtcccagaa tctatcactg gaccactttg atgagcatgg   1740
agatcctctc caaaggcaga gagcactgag tgctgtcagc atcctcacca tcaccatgaa   1800
ggaacaagaa aaatcacaag agccttgtct cccttgtgga gaaaacctgg catccaagta   1860
```

-continued

```
cctcgtgtgg aactgttgcc cccagtggct gtgcgttaag aaggtcctga gaactgtgat   1920
gactgacccg tttactgagc tggccatcac catctgcatc atcatcaaca ctgtcttctt   1980
ggccatggag catcacaaga tggaggccag ttttgagaag atgttgaata tagggaattt   2040
ggttttcact agcattttta tagcagaaat gtgcctaaaa atcattgcgc tcgatcccta   2100
ccactacttt cgccgaggct ggaacatttt tgacagcatt gttgctcttc tgagttttgc   2160
agatgtaatg aactgtgtac ttcaaaagag aagctggcca ttcttgcgtt ccttcagagt   2220
gctcagggtc ttcaagttag ccaaatcctg gccaactttg aacacactaa ttaagataat   2280
cggcaactct gtcggagccc ttggaagcct gactgtggtc ctggtcattg tgatctttat   2340
tttctcagta gttggcatgc agctttttgg ccgtagcttc aattcccaaa agagtccaaa   2400
actctgtaac ccgacaggcc cgacagtctc atgtttacgg cactggcaca tgggggattt   2460
ctggcactcc ttcctagtgg tattccgcat cctctgcggg gaatggatcg aaaatatgtg   2520
ggaatgtatg caagaagcga atgcatcatc atcattgtgt gttattgtct tcatattgat   2580
cacggtgata ggaaaacttg tggtgctcaa cctcttcatt gccttactgc tcaattcctt   2640
tagcaatgag gaaagaaatg gaaacttaga aggagaggcc aggaaaacta aagtccagtt   2700
agcactggat cgattccgcc gggctttttg ttttgtgaga cacactcttg agcatttctg   2760
tcacaagtgg tgcaggaagc aaaacttacc acagcaaaaa gaggtggcag gaggctgtgc   2820
tgcacaaagc aaagacatca ttcccctggt catggagatg aaaaggggct cagagaccca   2880
ggaggagctt ggtatactaa cctctgtacc aaagaccctg ggcgtcaggc atgattggac   2940
ttggttggca ccacttgcgg aggaggaaga tgacgttgaa ttttctggtg aagataatgc   3000
acagcgcatc acacaacctg agcctgaaca acaggcctat gagctccatc aggagaacaa   3060
gaagcccacg agccagagag ttcaaagtgt ggaaattgac atgttctctg aagatgagcc   3120
tcatctgacc atacaggatc cccgaaagaa gtctgatgtt accagtatac tatcagaatg   3180
tagcaccatt gatcttcagg atggctttgg atggttacct gagatggttc ccaaaaagca   3240
accagagaga tgtttgccca aaggctttgg ttgctgcttt ccatgctgta gcgtggacaa   3300
gagaaagcct ccctgggtca tttggtggaa cctgcggaaa acctgctacc aaatagtgaa   3360
acacagctgg tttgagagct ttattatctt tgtgattctg ctgagcagtg gggcactgat   3420
atttgaagat gttcaccttg agaaccaacc caaaatccaa gaattactaa attgtactga   3480
cattattttt acacatattt ttatcctgga gatggtacta aaatgggtag ccttcggatt   3540
tggaaagtat ttcaccagtg cctggtgctg ccttgatttc atcattgtga ttgtctctgt   3600
gaccaccctc attaacttaa tggaattgaa gtccttccgg actctacgag cactgaggcc   3660
tcttcgtgcg ctgtcccagt ttgaaggaat gaaggtggtg gtcaatgctc tcataggtgc   3720
catacctgcc attctgaatg ttttgcttgt ctgcctcatt ttctggctcg tattttgtat   3780
tctgggagta tacttctttt ctggaaaatt tgggaaatgc attaatggaa cagactcagt   3840
tataaattat accatcatta caaataaaag tcaatgtgaa agtggcaatt tctcttggat   3900
caaccagaaa gtcaactttg acaatgtggg aaatgcttac ctcgctctgc tgcaagtggc   3960
aacatttaag ggctggatgg atattatata tgcagctgtt gattccacag agaaagaaca   4020
acagccagag tttgagagca attcactcgg ttacatttac ttcgtagtct ttatcatctt   4080
tggctcattc ttcactctga atctcttcat tggcgttatc attgacaact tcaaccaaca   4140
gcagaaaaag ttaggtggcc aagacatttt tatgacagaa gaacagaaga aatactataa   4200
```

-continued

```
tgcaatgaaa aaattaggat ccaaaaaacc tcaaaaaccc attccacggc ctctgaacaa   4260
atgtcaaggt ctcgtgttcg acatagtcac aagccagatc tttgacatca tcatcataag   4320
tctcattatc ctaaacatga ttagcatgat ggctgaatca tacaaccaac ccaaagccat   4380
gaaatccatc cttgaccatc tcaactgggt ctttgtggtc atctttacgt tagaatgtct   4440
catcaaaatc tttgctttga ggcaatacta cttcaccaat ggctggaatt tatttgactg   4500
tgtggtcgtg cttctttcca ttgttagtac aatgatttct accttggaaa atcaggagca   4560
cattcctttc cctccgacgc tcttcagaat tgtccgcttg gctcggattg gccgaatcct   4620
gaggcttgtc cgggctgcac gaggaatcag gactctcctc tttgctctga tgatgtcgct   4680
tccttctctg ttcaacattg gtcttctact ctttctgatt atgtttatct atgccattct   4740
gggtatgaac tggttttcca aagtgaatcc agagtctgga atcgatgaca tattcaactt   4800
caagactttt gccagcagca tgctctgtct cttccagata agcacatcag caggttggga   4860
ttccctgctc agccccatgc tgcgatcaaa agaatcatgt aactcttcct cagaaaactg   4920
ccacctccct ggcatagcca catcctactt tgtcagttac attatcatct cctttctcat   4980
tgttgtcaac atgtacattg ctgtgatttt agagaacttc aatacagcca ctgaagaaag   5040
tgaggaccct ttgggtgaag atgactttga catattttat gaagtgtggg aaaagtttga   5100
cccagaagca acacaattta tcaaatattc tgccctttct gactttgctg atgccttgcc   5160
tgagcctttg cgtgtcgcaa agccaaataa atatcaattt ctagtaatgg acttgcccat   5220
ggtgagtgaa gatcgcctcc actgcatgga tattcttttc gccttcaccg ctagggtact   5280
cggtggctct gatggcctag atagtatgaa agcaatgatg gaagagaagt tcatggaagc   5340
caatcctctc aagaagttgt atgaacccat agtcaccacc accaagagaa aggaagagga   5400
aagaggtgct gctattattc aaaaggcctt tcgaaagtac atgatgaagg tgaccaaggg   5460
tgaccaaggt gaccaaaatg acttggaaaa cgggcctcat tcaccactcc agactctttg   5520
caatggagac ttgtctagct ttggggtggc caagggcaag gtccactgtg actgagccct   5580
cacctccacg cctacctcat agcttcacag ccttgccttc agcctctgag ctccaggggt   5640
cagcagctta gtgtatcaac agggagtgga ttcaccaaat tagccattcc attttctttt   5700
ctggctaaaa taaatgatat ttcaatttca ttttaaataa tacttacaga gatataagat   5760
aaggctactt gacaaccagt ggtactatta taataaggaa gaagacacca ggaaggactg   5820
taaaaggaca taccaatttt aggattgaaa tagttcaggc cgggcgcagt ggctcatgcc   5880
tgtaatccca gcactttgag aggccaaggc aggtggatca cgaggtcaag agatcgagac   5940
catcctggcc aacatgatga aactccgtct ctactaaaaa tacaaaaatt agctgggcat   6000
ggtggcgtgc gcctgtagtc ccagctactt gggaggctga ggcaggagaa tcgcttaaac   6060
ctgggagacg gaggttgcag tgagccaaga tcgtgccact gcactccagc ctggtgacag   6120
agtgagactc tgtttcaaaa aagaaaagaa aagaaacatg gttcaaatta tatctaaaca   6180
aaaaagaata agaaacaaaa aacacattaa aattttaagt tgtattttct atgtttctag   6240
atacatcatt tttgtttgat attttcctga tgcaagtatg tggtttatca catgtagctc   6300
ttttgcatgc taaatgaaaa ttcaaaactt gccaataaat gaatagctta ttgcagacat   6360
tttttaccaa cattaattat tttgggtttg tttaaaacct agaggcacaa tcttgacttg   6420
tcaattacta ccctttcaca agctaccatc tcagatatat atatatatat aaattcaata   6480
aagctttctg tttgtgttcc                                               6500
```

<210> SEQ ID NO 11
<211> LENGTH: 6528
<212> TYPE: DNA
<213> ORGANISM: Homo sapiens

<400> SEQUENCE: 11
tcctgctata cccacagtgg tggtcatctc ttctgatctt cacagccaat cagctcccaa 60
ggcccctgac ctcagctcag cttttgtaga tccttatgac accatccttt aagactggaa 120
tcctagggca ggctgtttta ttcccgcctc ctgaggcctt tctgaggatc tgtggcttgt 180
ctctgtcctg agggtgaaga tggatgacag atgctaccca gtaatctttc cagatgagcg 240
gaatttccgc cccttcactt ccgactctct ggctgcaatt gagaagcgga ttgccatcca 300
aaaggagaaa aagaagtcta aagaccagac aggagaagta ccccagcctc ggcctcagct 360
tgacctaaag gcctccagga agttgcccaa gctctatggc gacattcctc gtgagctcat 420
aggaaagcct ctggaagact tggacccatt ctaccgaaat cataagacat ttatggtgtt 480
aaacagaaag aggacaatct accgcttcag tgccaagcat gccttgttca tttttgggcc 540
tttcaattca atcagaagtt tagccattag agtctcagtc cattcattgt tcagcatgtt 600
cattatcggc accgttatca tcaactgcgt gttcatggct acagggcctg ctaaaaacag 660
caacagtaac aatactgaca ttgcagagtg tgtcttcact gggatttata tttttgaagc 720
tttgattaaa atattggcaa gaggtttcat tctggatgag ttttctttcc ttcgagatcc 780
atggaactgg ctggactcca ttgtcattgg aatagcgatt gtgtcatata ttccaggaat 840
caccatcaaa ctattgcccc tgcgtacctt ccgtgtgttc agagctttga aagcaatttc 900
agtagtttca cgtctgaagg tcatcgtggg ggccttgcta cgctctgtga agaagctggt 960
caacgtgatt atcctcacct tcttttgcct cagcatcttt gccctggtag gtcagcagct 1020
cttcatggga agtctgaacc tgaaatgcat ctcgagggac tgtaaaaata tcagtaaccc 1080
ggaagcttat gaccattgct ttgaaaagaa agaaaattca cctgaattca aaatgtgtgg 1140
catctggatg ggtaacagtg cctgttccat acaatatgaa tgtaagcaca ccaaaattaa 1200
tcctgactat aattatacga attttgacaa ctttggctgg tcttttcttg ccatgttccg 1260
gctgatgacc caagattcct gggagaagct ttatcaacag accctgcgta ctactgggct 1320
ctactcagtc ttcttcttca ttgtggtcat tttcctgggc tccttctacc tgattaactt 1380
aaccctggct gttgttacca tggcatatga ggagcagaac aagaatgtag ctgcagagat 1440
agaggccaag gaaaagatgt ttcaggaagc ccagcagctg ttaaaggagg aaaaggaggc 1500
tctggttgcc atgggaattg acagaagttc acttacttcc cttgaaacat catattttac 1560
cccaaaaaag agaaagctct ttggtaataa gaaaaggaag tccttctttt tgagagagtc 1620
tgggaaagac cagcctcctg ggtcagattc tgatgaagat tgccaaaaaa agccacagct 1680
cctagagcaa accaaacgac tgtcccagaa tctatcactg gaccactttg atgagcatgg 1740
agatcctctc caaaggcaga gagcactgag tgccgtcagc atcctcacca tcaccatgaa 1800
ggaacaagaa aaatcacaag agccttgtct cccttgcgga gaaaacctgg catccaagta 1860
cctcgtgtgg aactgttgcc cccagtggct gtgcgttaag aaggtcctga gaactgtgat 1920
gactgacccg tttactgagc tggccatcac catctgcatc atcatcaaca ctgtcttctt 1980
ggccatggag catcacaaga tggaggccag ttttgagaag atgttgaata tagggaattt 2040
ggttttcact agcattttta tagcagaaat gtgcctaaaa atcattgcgc tcgatcccta 2100
ccactacttt cgccgaggct ggaacatttt tgacagcatt gttgctcttc tgagttttgc 2160

-continued

```
agatgtaatg aactgtgtac ttcaaaagag aagctggcca ttcttgcgtt ccttcagggt   2220
gctcagggtc ttcaagttag ccaaatcctg gccaactttg aacacactaa ttaagataat   2280
cggcaactct gtcggagccc ttggaaacct gactgtggtc ctggtcattg tgatctttat   2340
tttctcagta gttggcatgc agctttttgg ccgtagcttc aattcccaaa agagtccaaa   2400
actctgtaac ccgacaggcc cgacagtctc atgtttacgg cactggcaca tgggggattt   2460
ctggcactcc ttcctagtgg tattccgcat cctctgcggg gaatggatcg aaaatatgtg   2520
ggaatgtatg caagaagcga atgcatcatc atcattgtgt gttattgtct tcatattgat   2580
cacggtgata ggaaaacttg tggtgctcaa cctcttcatt gccttactgc tcaattcctt   2640
tagcaatgag gaaagaaatg gaaacttaga aggagaggcc aggaaaacta aagtccagtt   2700
agcactggat cgattccgcc gggctttttg ttttgtgaga cacactcttg agcatttctg   2760
tcacaagtgg tgcaggaagc aaaacttacc acagcaaaaa gaggtggcag gaggctgtgc   2820
tgcacaaagc aaagacatca ttcccctggt catggagatg aaaaggggct cagagaccca   2880
ggaggagctt ggtatactaa cctctgtacc aaagaccctg ggcgtcaggc atgattggac   2940
ttggttggca ccacttgcgg aggaggaaga tgacgttgaa ttttctggtg aagataatgc   3000
acagcgcatc acacaacctg agcctgaaca acaggcctat gagctccatc aggagaacaa   3060
gaagcccacg agccagagag ttcaaagtgt ggaaattgac atgttctctg aagatgagcc   3120
tcatctgacc atacaggatc cccgaaagaa gtctgatgtt accagtatac tatcagaatg   3180
tagcaccatt gatcttcagg atggctttgg atggttacct gagatggttc ccaaaaagca   3240
accagagaga tgtttgccca aaggctttgg ttgctgcttt ccatgctgta gcgtggacaa   3300
gagaaagcct ccctgggtca tttggtggaa cctgcggaaa acctgctacc aaatagtgaa   3360
acacagctgg tttgagagct ttattatctt tgtgattctg ctgagcagtg gggcactgat   3420
atttgaagat gttcaccttg agaaccaacc caaaatccaa gaattactaa attgtactga   3480
cattattttt acacatattt ttatcctgga gatggtacta aaatgggtag ccttcggatt   3540
tggaaagtat ttcaccagtg cctggtgctg ccttgatttc atcattgtga ttgtctctgt   3600
gaccaccctc attaacttaa tggaattgaa gtccttccgg actctacgag cactgaggcc   3660
tcttcgtgcg ctgtcccagt ttgaaggaat gaaggtggtg gtcaatgctc tcataggtgc   3720
catacctgcc attctgaatg ttttgcttgt ctgcctcatt ttctggctcg tattttgtat   3780
tctgggagta tacttctttt ctggaaaatt tgggaaatgc attaatggaa cagactcagt   3840
tataaattat accatcatta caaataaaag tcaatgtgaa agtggcaatt tctcttggat   3900
caaccagaaa gtcaactttg acaatgtggg aaatgcttac ctcgctctgc tgcaagtggc   3960
aacatttaag ggctggatgg atattatata tgcagctgtt gattccacag agaaagaaca   4020
acagccagag tttgagagca attcactcgg ttacatttac ttcgtagtct ttatcatctt   4080
tggctcattc ttcactctga atctcttcat tggcgttatc attgacaact tcaaccaaca   4140
gcagaaaaag ttaggtggcc aagacatttt tatgacagaa gaacagaaga aatactataa   4200
tgcaatgaaa aaattaggat ccaaaaaacc tcaaaaaccc attccacggc ctctgaacaa   4260
atgtcaaggt ctcgtgttcg acatagtcac aagccagatc tttgacatca tcatcataag   4320
tctcattatc ctaaacatga ttagcatgat ggctgaatca tacaaccaac ccaaagccat   4380
gaaatccatc cttgaccatc tcaactgggt ctttgtggtc atctttacgt tagaatgtct   4440
catcaaaatc tttgctttga ggcaatacta cttcaccaat ggctggaatt tatttgactg   4500
tgtggtcgtg cttctttcca ttgttagtac aatgatttct accttggaaa atcaggagca   4560
```

-continued

```
cattcctttc cctccgacgc tcttcagaat tgtccgcttg gctcggattg gccgaatcct   4620

gaggcttgtc cgggctgcac gaggaatcag gactctcctc tttgctctga tgatgtcgct   4680

tccttctctg ttcaacattg gtcttctact ctttctgatt atgtttatct atgccattct   4740

gggtatgaac tggttttcca aagtgaatcc agagtctgga atcgatgaca tattcaactt   4800

caagactttt gccagcagca tgctctgtct cttccagata agcacatcag caggttggga   4860

ttccctgctc agccccatgc tgcgatcaaa agaatcatgt aactcttcct cagaaaactg   4920

ccacctccct ggcatagcca catcctactt tgtcagttac attatcatct cctttctcat   4980

tgttgtcaac atgtacattg ctgtgatttt agagaacttc aatacagcca ctgaagaaag   5040

tgaggaccct ttgggtgaag atgactttga catattttat gaagtgtggg aaaagtttga   5100

cccagaagca acacaattta tcaaatattc tgccctttct gactttgctg atgccttgcc   5160

tgagcctttg cgtgtcgcaa agccaaataa atatcaattt ctagtaatgg acttgcccat   5220

ggtgagtgaa gatcgcctcc actgcatgga tattcttttc gccttcaccg ctagggtact   5280

cggtggctct gatggcctag atagtatgaa agcaatgatg gaagagaagt tcatggaagc   5340

caatcctctc aagaagttgt atgaacccat agtcaccacc accaagagaa aggaagagga   5400

aagaggtgct gctattattc aaaaggcctt tcgaaagtac atgatgaagg tgaccaaggg   5460

tgaccaaggt gaccaaaatg acttggaaaa cgggcctcat tcaccactcc agactctttg   5520

caatggagac ttgtctagct ttggggtggc caagggcaag gtccactgtg actgagccct   5580

cacctccacg cctacctcat agcttcacag ccttgccctc agcctctgag ctccaggggt   5640

cagcagctta gtgtatcaac agggagtgga ttcaccaaat tagccattcc attttctttt   5700

ctggctaaat aaatgatatt tcaatttcat tttaaatgat acttacagag atataagata   5760

aggctacttg acaaccagcg gtactatttt aataaggaag aagacaccag gaaggactgt   5820

aaaaggacat tccaatttta ggattggaat agttcaagcc gggcgcagtg gctcatgcct   5880

ggaatcccag cactttgaga ggccaaggca ggtggatcac gaggtcaaga gatcgagacc   5940

atcctggcca accatgatga aactccgtct ctactaaaat acaaaaatta gctgggcatg   6000

gttgcgtgcg cctgtagtcc cagctacttg ggaggctgag gcaggagaat cgcttaaacc   6060

tgggagacgg aggttgcagt gagccaagat cgtgtcactg cactccagcc tggtgacaga   6120

gtgagactct gtttcaaaaa agaaaagaaa agaaacatgg ttcaaattat atctaaacaa   6180

aaaagaataa gaaacaaaaa acacattaaa attttaagtt gtattttcta tgtttctaga   6240

tacatcattt ttgtttgata ttttcctgat gcaagtatgt ggtttatcac atgtagctct   6300

tttgcatgct aaatgaaaat tcaagacttg ccaataaatg aatagcttat tgcagacatt   6360

ttttaccaac attaattatt ttgggtttgt ttaaaaccta gaggcacaat cttgacttgt   6420

caattactac cctttcacaa gctaccatct cagatatata tatatatata aattcaataa   6480

agctttctgt ttgtgttcca taaaaaaaaa aaaaaaaaaa aaaaaaaa                6528
```

TREATMENT OF DISEASES RELATED TO ALPHA SUBUNITS OF SODIUM CHANNELS, VOLTAGE-GATED (SCNXA) WITH SMALL MOLECULES

The present application claims the priority of U.S. Provisional Patent Application No. 61/531,361 filed Sep. 6, 2011, which is incorporated herein by reference in its entirety.

FIELD OF THE INVENTION

Embodiments of the invention comprise small molecules that modulate the expression and/or function of alpha subunits of voltage-gated sodium channels and associated molecules.

BACKGROUND

The provision of proteins which are underexpressed in biological systems using pharmaceutical agents is a promising method of treating or potentially treating a multitude of disease states. The medical and pharmaceutical community has approached the treatment of this type of disease modality by multiple mechanistic and avenues. In one approach, a natural antisense transcript (NAT) of the mRNA corresponding to a particular target protein has been selected as the target. Oligonucleotides and/or modified oligonucleotides have been designed to target the NAT and "up-regulate" the expression of the target mRNA and protein. Because of the vast number of disease states and conditions which require or need new and/or first line pharmaceutical treatment, there is a significant need for new approaches and drugs to modulate protein expression or underexpression.

The prior art in general includes gene therapy, antisense technology, siRNA technology as well as the use of small molecules to regulate protein expression. Most of the antisense technology and the siRNA technology and related patents or patent applications relates to the use of such "drugs" to mitigate (down regulate) the expression of proteins. The therapeutic target is often the mRNA or DNA coding for the particular protein or coding for the RNA which is translated into the protein of interest. Examples of various disclosures from the patent literature are provided below.

U.S. Pat. No. 5,739,119 claims antisense oligonucleotides specific for the muscarinic type 2 acetylcholine receptor mRNA. Administration results in an increase in memory and learning.

U.S. Pat. No. 5,985,663 claims antisense inhibition of interleukin-15 expression.

U.S. Pat. No. 6,165,712 claims molecules which transcriptionally modulate the expression of a gene and increase production of recombinant proteins. This reference discloses the upregulation of proteins. The modulating molecule may comprise an antisense nucleic acid. The modulating molecule may bind to a promoter region upstream of the coding sequence encoding an oncogene or tumor suppressor gene.

U.S. Pat. No. 6,165,990 claims the use of expression vectors which code for antisense nucleotides that target mRNA associated with colon cancer-Gastrin gene.

U.S. Pat. No. 6,303,374 claims antisense modulation of Caspase 3 expression. The antisense nucleotides target nucleic acids encoding caspase 3 for the treatment of Alzheimer's, Parkinson's. ALS, etc.

U.S. Pat. No. 6,376,541 claims a method of treating glaucoma by "upregulating" the production of prostaglandins by treating a patient with an agent that causes the upregulation of the prostaglandin—the agents include interleukin-1, transforming growth factor-beta 1, transforming growth factor-beta 2, platelet derived growth factor, levamisole etc. This patent discloses an example of the use of a drug to upregulate the expression of a small molecule instead of a protein.

U.S. Pat. No. 6,444,464 discloses antisense nucleotides targeted to nucleic acids encoding transcription factors E2F.

U.S. Pat. No. 6,617,122 claims polypeptides, nucleic acid molecules expressing such polypeptides, and a method of treating a human having low HDL comprising administering to such human an ABC1 polypeptide, or cholesterol regulating fragment thereof. The ABC-1 polypeptide is wild type ABC-1 or has a mutation that increases its stability or its biological activity. The patent also discloses candidate compounds that modulate (increase) the level of expression of said protein. Antisense nucleotides to the cDNA of the ABC-1 protein were disclosed. The reference discloses that using a compound to inhibit a transcription factor that represses ABC1 would be expected to result in upregulation of ABC1 and, therefore, raise HDL levels. The transcription factor is a protein.

U.S. Pat. No. 6,710,174 discloses antisense inhibition of vascular endothelial growth factor.

U.S. Pat. No. 7,144,999 discloses oligonucleotides that target hypoxia-inducible factor 1 alpha (aHIF) expression and methods for treating diseases associated with the expression of such a protein. This patent discloses the overexpression of a natural antisense transcript of aHIF that is complementary to the 3' untranslated region of HIF-1 alpha and which is associated with a human disease (non-pappilary clear-cell renal carcinoma).

U.S. Pat. No. 7,148,204 discloses antisense modulators of BCL-X expression. Modulation induces apoptosis.

U.S. Pat. No. 7,199,107 discloses antisense modulators of Kinesin-like 1 expression.

U.S. Pat. No. 7,202,357 discloses antisense compounds, compositions and methods are disclosed for modulating the expression of acyl CoA cholesterol acyltransferase-2. The compounds are antisense oligonucleotides targeted to nucleic acids encoding acyl CoA cholesterol acyltransferase-2.

U.S. Pat. No. 7,229,976 discloses antisense oligomers targeted to a nucleic acid encoding forkhead box O1A to modulate expression thereof.

U.S. Pat. No. 7,235,534 discloses antisense oligonucleotides that target the genes and mRNAs encoding mammalian estrogen receptors (ER) alpha and/or beta and modulate the receptors' responses. The treatment improves plaque stabilization and vascular healing and endothelial recovery after vascular injury.

U.S. Pat. No. 7,285,288 discloses oligonucleotides that hybridize to Bcl-2 nucleic acids, the gene products are known to interact with the tumorigenic protein Bcl-2.

U.S. Pat. No. 7,335,764 discloses antisense modulators of acyl coA cholesterol acyltransferase-2 expression.

U.S. Pat. No. 7,402,574 discloses antisense compositions and methods for treating cancer. The antisense composition comprises a substantially uncharged antisense compound having a nuclease-resistant backbone, capable of uptake by target cancer cells in the subject, containing between 10-40 nucleotide bases and having a base sequence effective to hybridize to a region of processed or preprocessed human SNAIL RNA transcript having a specific sequence ID NO: 21.

U.S. Pat. No. 7,420,050 discloses antisense molecules which inhibit the expression of TGF-beta. Kidney disease.

U.S. Pat. No. 7,425,545 discloses modulation of C-reactive Protein expression.

U.S. Pat. No. 7,456,154 discloses antisense oligonucleotides against human acetylcholinesterase and uses thereof.

U.S. Pat. No. 7,598,227 discloses modulation of apolipoprotein C-III expression.

U.S. Pat. No. 7,662,948 discloses antisense oligonucleotides against VR1 (capsaicin receptor) for the treatment of pain.

U.S. Pat. No. 7,674,895 discloses siRNAs specific for the VEGF and VEGF receptor genes.

U.S. Pat. No. 7,687,617 discloses oligonucleotides with alternating segments of locked and non-locked nucleotides.

U.S. Pat. No. 7,691,995 discloses in vivo production of small interfering RNAs.

U.S. Pat. No. 7,709,546 discloses modulation of gene expression by oligomers targeted to chromosomal DNA.

U.S. Pat. No. 7,709,630 discloses antisense modulation of connective tissue growth factor expression.

U.S. Pat. No. 7,723,508 discloses modulation of apolipoprotein (A) expression.

U.S. Pat. No. 7,732,422 discloses TRPM-2 antisense therapy for the treatment of cancer.

U.S. Pat. No. 7,732,590 discloses modulation of diacylglycerol acyltransferase 2 expression.

U.S. Pat. No. 7,737,265 discloses RNAi modulation of HIF-1 and therapeutic uses thereof.

U.S. Pat. No. 7,741,305 discloses modulation of apo A1 expression.

US2003/0191075 discloses methods of targeting gene therapy (antisense nucleotides) to specific organs using modified oligonucleotides-lipophilc oligonucleotide conjugates.

US2004/0033480 discloses the use of resveratrol (3,5,4'-trihydroxy-trans-stilbene) to upregulate the expression of apolipoprotein A1.

US2004/0137423 discloses compositions and methods for identifying agents that modulate HDL levels in animals by increasing ABCA1-gene expression.

US2004/0175803 discloses an interferon-alpha induced (upregulated) gene.

The present inventors have discovered new uses of known small molecules that result in the modulation of expression of the SCNA gene family and variants thereof.

SUMMARY

This Summary is provided to briefly indicate the nature and substance of the invention. It is submitted with the understanding that it will not be used to interpret or limit the scope or meaning of the claims.

In one embodiment, the invention comprises a method of modulating the expression of a gene encoding an alpha subunit of a voltage gated sodium channel (SCNxA) comprising administration to a patient in need thereof of at least one active ingredient selected from the group consisting of a diuretic, an atypical antipsychotic, a potassium channel opener, a calcium channel blocker, an antifungal, an antioxidant, a PDE5 inhibitor, an estrogen agonist (steroidal or non-steroidal), an antidepressant, a proton pump inhibitor, a 5HT1D receptor agonist, a hypnotic, an anti-ulcer medication, a 5HT4 agonist, a GABA agonist, an antihistamine or an anabolic steroid for the treatment of an SCNxA related disorder or disease.

In another embodiment, this invention comprises a method of modulating the expression of an SCNxA gene comprising administration of at least one small molecule selected from the group consisting of milnacipran, torsemide, risperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof.

In one embodiment, the method comprises screening a compound library of small molecules against biological systems that have an SCNxA gene expression system wherein said screening results in putative hits that up-regulate the expression of the SCNxA expression product and/or gene product. The preferred expression product target is SCN1A.

In another embodiment, the invention comprises a method of interfering with the function of an SCNxA RNA wherein said interference results in the up-regulation of the SCNxA gene product, comprising administering a small molecule selected from the group consisting of milnacipran, torsemide, risperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof wherein the functions of RNA to be interfered with include at least one vital function, such as, for example, transcription of said RNA, translocation of the RNA to the site of protein translation, translation of protein from the RNA, splicing of the RNA to yield one or more mRNA species, and catalytic activity which may be engaged in or facilitated by an enzymatic RNA.

One embodiment provides a method of modulating function and/or expression of an SCNxA polynucleotide in biological systems comprising contacting said system with a small molecule selected from the group consisting of milnacipran, torsemide, risperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof thereby modulating function and/or expression of the SCNxA polynucleotide in biological systems.

One embodiment provides a method of modulating function and/or expression of an SCNxA polynucleotide in patient cells or tissues in vivo or in vitro comprising contacting said cells or tissues with a small molecule selected from the group consisting of milnacipran, torsemide, risperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof thereby modulating function and/or expression of the SCNxA polynucleotide in patient cells or tissues in vivo or in vitro.

In another embodiment, a small molecule selected from the group consisting of milnacipran, torsemide, risperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof modifies the expression of SCNxA polynucleotides, for example, nucleotides set forth in SEQ ID NO:1, and any variants, alleles, homologs, mutants, derivatives, fragments and complementary sequences thereto.

Another embodiment provides a method of modulating function and/or expression of an SCN1A polynucleotide in patient cells or tissues in vivo or in vitro comprising contacting said cells or tissues with a small molecule selected from the group consisting of milnacipran, torsemide, risperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof thereby modulating function and/or expression of the SCN1A polynucleotide in patient cells or tissues in vivo or in vitro.

In an embodiment, the invention comprises a pharmaceutical composition comprising a small molecule selected from the group consisting of milnacipran, torsemide, risperidone, pinacidil, benidipine, ketoconazole, ebselen, tadalafil, zeranol, nefazadone, lomerizine, icariin, omeprazole, L-694, 247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof and a pharmaceutically acceptable excipient wherein said composition modulates the expression of an SCNxA polynucleotide.

In another embodiment, the small molecules are administered to a patient orally, subcutaneously, intramuscularly, intravenously or intraperitoneally.

A treatment regimen comprises administering the small molecules at least once to patient; however, this treatment can be modified to include multiple doses over a period of time. The treatment can be combined with one or more other types of therapies.

In another embodiment, the small molecules are encapsulated in a liposome or attached to a carrier molecule (e.g. cholesterol, TAT peptide) or targeted nanoparticles and/or antibody coated vesicles depending upon the physical and/or chemical properties of the particularly selected small molecule.

In an embodiment, the present invention comprises modulation of the expression of any one of the isoforms of SCNxA family members and variants thereof comprising administration to a patient in need of treatment thereof a pharmaceutically effective amount of at least one compound recited herein wherein said modulation results in the treatment of a disease associated with at least one of the SCNxA genes or expression products produced therefrom.

Other aspects are described intra.

BRIEF DESCRIPTION OF THE DRAWINGS

Sequence Listing Description

FIG. 1 shows increase in SCN1A mRNA levels in primary skin fibroblasts carrying a Dravet-associated mutation (hatched bars) and adult primary keratinocytes (empty bars) after treatment with small compounds at a concentration of 1 uM.

SEQ ID NO: 1: *Homo sapiens* sodium channel, voltage-gated, type I, alpha subunit (SCN1A), transcript variant 1, mRNA (NCBI Accession No.: NM_001165963).

SEQ ID NO: 2: *Homo sapiens* sodium channel, voltage-gated, type II, alpha subunit (SCN2A), transcript variant 1, mRNA (NCBI Accession No.: NM_021007.2).

SEQ ID NO: 3: *Homo sapiens* sodium channel, voltage-gated, type III, alpha subunit (SCN3A), transcript variant 1, mRNA (NCBI Accession No.: NM_006922.3).

SEQ ID NO: 4: *Homo sapiens* sodium channel, voltage-gated, type IV, alpha subunit (SCN4A), mRNA (NCBI Accession No.: NM_000334.4).

SEQ ID NO: 5: *Homo sapiens* sodium channel, voltage-gated, type V, alpha subunit (SCN5A), transcript variant 1, mRNA (NCBI Accession No.: NM_198056.2).

SEQ ID NO: 6: *Homo sapiens* sodium channel, voltage-gated, type VII, alpha (SCN7A), mRNA (NCBI Accession No.: NM_002976.3)

SEQ ID NO: 7: *Homo sapiens* sodium channel, voltage gated, type VIII, alpha subunit (SCN8A), transcript variant 1, mRNA (NCBI Accession No.: NM_014191.2)

SEQ ID NO: 8: *Homo sapiens* sodium channel, voltage-gated, type IX, alpha subunit (SCN9A), mRNA (NCBI Accession No.: NM_002977.3)

SEQ ID NO: 9: *Homo sapiens* sodium channel, voltage-gated, type X, alpha subunit (SCN10A), mRNA (NCBI Accession No.: NM_006514.2)

SEQ ID NO: 10: *Homo sapiens* sodium channel, voltage-gated, type XI, alpha subunit (SCN11A), mRNA (NCBI Accession No.: NM_014139.2)

SEQ ID NO: 11: *Homo sapiens* voltage-gated sodium channel alpha subunit SCN12A (SCN12A) mRNA (NCBI Accession No.: AF109737.1). The sequence listings provided in all cases are actually the cDNA version of the RNS transcript.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In an embodiment, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

As used herein "SCNxA" and "sodium channel, voltage-gated, alpha subunit" are inclusive of all family members, mutants, alleles, isoforms, fragments, species, coding and noncoding sequences, sense and antisense polynucleotide strands, etc. The SCNxA gene family consists of 11 known members (SCN1A, SCN2A, SCN3A, SCN4A. SCN5A, SCN7A (also known as SCN6A), SCN8A, SCN9A, SCN10A, SCN11A and SCN12A).

As used herein, the words 'sodium channel, voltage-gated, type I, alpha subunit', SCN1A, FEB3, FEB3A, GEFSP2, HBSC1, NAC1, Nav1.1, SCN1, SMEI, sodium channel protein brain 1 subunit alpha, sodium channel protein type 1 subunit alpha, and voltage-gated sodium channel subunit alpha Nay 1.1, are considered same in the literature and are used interchangeably in the present application.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

As used herein, "modulation" means either an increase (stimulation) or a decrease (inhibition) in the expression of a gene. The term "modulating expression" further means to either enhance or reduce the expression of a given protein by interfering with the expression, or translation of RNA. In the case of enhanced protein expression, the drug may block expression of a suppressor gene—e.g., a tumor suppressor gene or any other gene product or mutated gene that results in down regulation or under expression of a protein product. In the case of reduced protein expression, the drug may directly block expression of a given gene or contribute to the accelerated breakdown of the RNA transcribed from that gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it, (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroopthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using the small molecules, pharmaceutical compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder, autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor, Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejerine-Klumke palsy; dementia; dermatomyositis; diabetic neuropathy; diffuse sclerosis; Dravetts, dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIV associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease: Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae oflupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and 11); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; severe myoclonic epilepsy of infancy shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), peripheral vascular disease, venous thromboembolism, pulmonary embolism, stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to SCN1A activation. CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

Examples of diseases or disorders associated with sodium channel dysfunction include, but are not restricted to, malignant hyperthermia, myasthenia, episodic ataxia, neuropathic and inflammatory pain, Alzheimer's disease, Parkinson's disease, schizophrenia, hyperekplexia, SMEI, FEB3, familial hemiplegic migraine type 3, myotonias such as hypo- and hyperkalaemic periodic paralysis, paramyotonia congenita and potassium aggravated myotonia as well as cardiac arrhythmias such as long QT syndrome.

Targets:

In one embodiment, the targets for modulation comprise nucleic acid sequences of sodium channel, voltage-gated, alpha subunit family members (SCNxA), including without limitation sense and/or antisense noncoding and/or coding as well as protein sequences associated with SCNxA transcription and/or translation and/or modulation. The preferred target is the SCN1A channel.

Voltage-sensitive ion channels are a class of transmembrane proteins that provide a basis for cellular excitability and the ability to transmit information via ion-generated membrane potentials. The voltage-gated sodium channels are responsible for the generation and propagation of action potentials in most electrically excitable cells, including neurons, heart cells, and muscle. Electrical activity is triggered by depolarization of the membrane, which opens transmembrane channels that are highly selective for sodium ions. Ions are then driven intracellularly through open channels by an electrochemical gradient. Although sodium-based action potentials in different tissues are similar, electrophysiological studies have demonstrated that multiple structurally and functionally distinct sodium channels exist, and numerous genes encoding sodium channels have been cloned. The SCNA gene belongs to a gene family of voltage-gated sodium channels (SCNxA family).

Voltage-gated sodium channels play an important role in the generation of action potential in nerve cells and muscle. The alpha subunits (SCNxA) are the main components of the channels, and would be sufficient to generate an ionic current when expressed in cells in vitro. However in nature the voltage gated sodium channels include two additional regulatory beta subunits. The role of these subunits would be to modify the sodium channel localization and density as well as kinetic properties, mainly by affecting the inactivation of the sodium currents. Mutations in the SCN1B gene are associated with GEFS+, Brugada syndrome and cardiac conduction defects, nonspecific. Mutations in SCN3B is also associated with Brugada syndrome, mutations in SCN4B cause long QT syndrome-10.

In an embodiment, the small molecules are selected from the group consisting of milnacipran, torsemide, risperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof are used to prevent or treat diseases or disorders associated with SCNxA family members. Exemplary sodium channel, voltage-gated, type I, alpha subunit (SCN1A) mediated diseases and disorders which can be treated with the drugs and/or with cell/tissues regenerated from stem cells obtained using the compounds comprise: a neurological disease or disorder, convulsion, pain (including chronic pain), impaired electrical excitability involving sodium channel dysfunction, a disease or disorder associated with sodium channel dysfunction, a disease or disorder associated with misregulation of voltage-gated sodium channel alpha subunit activity (e.g., paralysis, hyperkalemic periodic paralysis, paramyotonia congenita, potassium-aggravated myotonia, long Q-T syndrome 3, motor endplate disease, ataxia etc.), a gastrointestinal tract disease due to dysfunction of the enteric nervous system (e.g., colitis, ileitis, inflammatory bowel syndrome etc.), a cardiovascular disease or disorder (e.g., hypertension, congestive heart failure etc.); a disease or disorder of the genitourinary tract involving sympathetic and parasympathetic innervation (e.g., benign prostrate hyperplasia, impotence); a disease or disorder associated with neuromuscular system (e.g., muscular dystrophy, multiple sclerosis, epilepsy, autism, migraine (e.g., sporadic and familial hemiplegic migraines etc.), severe myoclonic epilepsy of infancy (SMEI) or Dravet syndrome, generalized epilepsy with febrile seizure plus (GEFS+) etc.) and SCN1A-related seizure disorders.

In an embodiment, the small molecules upregulate polynucleotides of SCN1A. The SCN1A targets comprise variants of SCN1A; mutants of SCN1A, including SNPs; noncoding sequences of SCN1A; alleles, isoforms, fragments and the like. Preferably the small molecule is selected from the group consisting of milnacipran, torasemide, resperidone, pinacidil, benidipine, ketoconazole, ebselen, tadalafil, zeranol, nefazadone, lomerizine, icariin, omeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof:

In accordance with embodiments of the invention, a target nucleic acid molecule is not limited to SCN1A polynucleotides alone but extends to any of the isoforms, receptors, homologs, non-coding regions and the like of SCN1A—e.g., the SCNxA family.

In another embodiment, a small molecule modulates SCN1A targets, including, without limitation, variants, alleles, homologs, mutants, derivatives, fragments and complementary sequences thereto.

In an embodiment, the small molecules modulate the expression of sodium channel, voltage-gated, type I, alpha subunit (SCN1A) and modulate the expression and/or function of sodium channel, voltage-gated, type I, alpha subunit (SCN1A) (SEQ ID NO: 1).

Alternative RNA transcripts can be produced from the same genomic region of DNA. These alternative transcripts are generally known as "splice variants". More specifically, "pre-mRNA variants" are transcripts produced from genomic DNA that contain both intronic and exonic sequences.

Upon excision of one or more exon or intron regions, or portions thereof during splicing, pre-mRNA variants produce smaller "mRNA variants". These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

In a further embodiment, the "preferred target segments" identified herein may be employed in a screen for additional compounds that modulate the expression of sodium channel, voltage-gated, type I, alpha subunit (SCN1A) polynucleotides. "Modulators" are those compounds that decrease or increase the expression of a nucleic acid molecule encoding sodium channel, voltage-gated, type I, alpha subunit (SCN1A) or its corresponding protein. The screening method comprises the steps of contacting a preferred target segment of a nucleic acid molecule encoding sense or natural antisense polynucleotides of Sodium channel, voltage-gated, type I, alpha subunit (SCN1A) or its corresponding protein with one or more candidate modulators, and selecting for one or more candidate modulators which decrease or increase the expression of a nucleic acid molecule encoding Sodium channel, voltage-gated, type I, alpha subunit (SCN1A) polynucleotides or its corresponding protein. Once it is shown that the candidate modulator or modulators are capable of modulating (e.g. either decreasing or increasing) the expression of a nucleic acid molecule encoding sodium channel, voltage-gated, alpha subunit (SCNxA) polynucleotides, the modulator may then be employed in further investigative studies of the function of sodium channel, voltage-gated, alpha subunit (SCNxA) polynucleotides, or for use as a research, diagnostic, or therapeutic agent in accordance with the present invention.

The small molecules used in accordance with this invention may be conveniently and routinely made through well known synthetic methods. Any other means for such synthesis may also be employed; the actual synthesis of the small molecules is well within the talents of one of ordinary skill in the art or such molecules may be obtained from a commercial vendor or supplier. Each of the preferred molecules used in the methods of the invention are known pharmaceutical drug products and can be purchased or obtained from active pharmaceutical ingredient manufacturers. In addition, such drugs have published synthetic methods and one of ordinary skill in the art of synthetic chemistry may synthesize such drugs via known routes or one of ordinary skill in the art may design new synthetic methods. These drugs and physical and salt forms thereof may be modified by standard chemical means to make pro-drugs. Such pro-drugs include esters and/or other chemical derivatives and/or modifications wherein, upon administration, the pro-drug cleaves into the known active pharmaceutical ingredient in the dosage form (drug product). These drugs, in term, may be metabolized into known active metabolites and such metabolites are included within the scope of the invention. The invention further includes enantiomers and/or diastereomers of the drug products, various salt forms including sodium and potassium salts as well as hydrates and solvates of such products. The invention further includes the use of amorphous forms of each of the drug products or salts thereof in any suitable dosage form. If the particular drug product contains an amine moiety, the present invention further includes acid salts of such products wherein the counterion is selected from a halide salt such as chloride or bromide and the like. Recrystallization methods and other known purification methods may be utilized to prepare crystal forms of such active pharmaceutical ingredients.

Transfer of a small molecule into a host cell or organism and determination of its effect upon RNA or protein up-regulation or down regulation can be assessed by several methods well known in the art. For example, SCN1A fibroblasts and/or keratinocytes or other cell types as desired are selected and grown for the specific assays herein. One day before the experiment cells are plated at the density of approximately $4\times10^4$/well into 24 well plates in Growth Media and incubated at 37° C. and 5% $CO_2$ overnight. Next day, the media in the 24 well plates is changed to fresh Growth Media (1 ml/well) and the cells are dosed with small compounds. Compound stocks are prepared in DMSO at a concentration of 1 mM. At the time of the experiment 1 mM stock solutions are diluted to the concentration of 1 uM in Growth Media. One in 1000 dilution of DMSO is used for the control wells. After 24-48 h incubation at 37° C. and 5% $CO_2$ the media is removed and RNA is extracted from the cells using SV Total RNA Isolation System from Promega (cat # Z3105) following the manufacturers' instructions. Six hundred nanograms of purified total RNA is added to the reverse transcription reaction performed using SuperScript VILO cDNA Synthesis Kit from Invitrogen (cat #11754-250) as described in the manufacturer's protocol. The cDNA from this reverse transcription reaction is used to monitor gene expression by real time PCR using ABI Taqman Gene Expression Mix (cat #4369510) and primers/probes designed by ABI (assays Hs00374696_ml, Hs00897350_ml or Hs00897341_ml for human SCN1A). The following PCR cycle is used: 50° C. for 2 min, 95° C. for 10 min, 40 cycles of (95° C. for 15 seconds, 60° C. for 1 min) using StepOne Plus Real Time PCR system (Applied Biosystems). The assay for 18S is manufactured by ABI (cat #4319413E). Fold change in gene expression after treatment with compounds is calculated based on the difference in 18S-normalized dCt values between compound- and vehicle-treated samples.

Expression of RNA after addition of the small molecule can also be detected by measuring an enzymatic activity or a reporter protein activity. For example, a coding region from a gene can be used to build a model control gene, by inserting a reporter coding region between the gene and its poly(A) signal into a self-replicating plasmid so that the gene and the reporter will always be expressed at the same level. The effectiveness of individual small molecules would be assayed by observing the modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), lucitferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

SCNxA protein and mRNA expression can be assayed using methods known to those of skill in the art and described elsewhere herein. For example, assays such as immunohistochemistry can be used to estimate protein levels. To achieve this, the cells will be grown in 24-well plates using appropriate growth conditions. Forty eight hours after addition of small compounds, the media will be removed and the cells will be washed 3 times with Dulbecco's phosphate-buffered saline without calcium and magnesium (PBS) (Mediatech cat #21-031-CV). Then PBS will be discarded and the cells will be fixed in the 24 well plate using 300 μl of 100% methanol for 15 min at −20° C. After removing the methanol and washing with PBS, the cells will be incubated with 3% hydrogen peroxide (Fisher Chemical cat # H325-100) for 5 min at 21° C. The cells will be washed three times for 5 min with PBS, then incubated with 300 μl of bovine serum albumin (BSA) (Sigma cat # A-9647) at 0.1% in PBS for 30 min at 21° C. The cells will be washed three times for 5 min with PBS then incubated with 300 μl of avidin solution (Vector Laboratories cat # SP-2001) for 30 min at 21° C. The cells will be briefly rinsed three times with PBS then incubated with biotin solution (Vector Laboratories cat # SP-2001) for 30 min at 21° C. The cells will be washed three times with PBS and then incubated overnight at 4° C. with 300 μl per well of rabbit antibody raised against a synthetic peptide (EEQKKYYNAMKKLGSKKP) corresponding to C terminal amino acids 1491-1508 of rat Scn1a (Abcam cat # ab24820; known to recognize rat Scn1a, human SCN1A and mouse Scn1a) diluted at 1:250 in PBS/BSA 0.1%. After equilibrating the plate for 5 min at 21° C., the cells will be washed three times 5 min each with PBS then incubated with goat anti-rabbit antibody diluted 1:200 in PBS/BSA 0.1% for 30 min at 21° C. The cells will be washed three times for 5 min with PBS and then incubated with 300 μl of Vectastain Elite ABC reagent A+B solution (Vector Laboratories cat # PK-6101) for 30 min; the Vectastain Elite ABC reagent A+B solution will be prepared at 21° C. 30 min before incubation with the cells by adding and mixing successively 2 drops of reagent A to 5 ml of PBS and then 2 drops of reagent B. The cells will be washed 3 times for 5 min each with PBS at 21° C. and then incubated with Diaminobenzidine (DAB) peroxidase substrate solution (Vector Laboratories cat # SK-4105) until cells are stained; the DAB peroxidase substrate solution will be reconstituted before being added to the cells by mixing 1 ml of ImmPACT™ DAB Diluent with 30 μl of ImmPACT™ DAB Chromogen concentrate. At this time, the cells will be briefly washed three times with PBS and 300 μl of PBS will be left in each well. The staining of the cells will be analyzed directly inside the wells of the 24-well plate using an inverted Nikon Eclipse TS100 microscope equipped with a Nikon DS-Ril camera coupled with Nikon Digital-Sight equipment on the screen of a Dell Latitude D630 laptop. Photos of individual wells will be made using the software provided with the Nikon camera, the NIS-Elements D 3.0.

Additionally, SCN1A protein can be quantified by enzyme-linked immunosorbent assay (ELISA). To achieve this, the cells will be grown in 24-well plates using appropriate growth conditions. Forty eight hours after addition of small compounds, the media will be removed and the cells will be washed 3 times with Dulbecco's phosphate-buffered saline without calcium and magnesium (PBS) (Mediatech cat #21-031-CV). Then PBS will be discarded and the cells will be fixed in the 24 well plate using 100 μl of 100% methanol for 15 min at −20° C. After removing the methanol and washing with PBS, the cells will be incubated with 3% hydrogen peroxide (Fisher Chemical cat # H325-100) for 5 min at 21° C. The cells will be washed three times for 5 min with PBS, then incubated with 100 μl of bovine serum albumin (BSA) (Sigma cat # A-9647) at 0.1% in PBS for 30 min at 21° C. The cells will be washed three times for 5 min with PBS then incubated with 300 μl of avidin solution (Vector Laboratories cat # SP-2001) for 30 min at 21° C. The cells will be briefly rinsed three times with PBS then incubated with biotin solution (Vector Laboratories cat # SP-2001) for 30 min at 21° C. The cells will be washed three times with PBS and then incubated overnight at 4° C. with 100 μl per well of rabbit antibody raised against a synthetic peptide (EEQKKYYNAMKKLGSKKP) corresponding to C terminal amino acids 1491-1508 of rat Scn1a (Abcam cat # ab24820; known to recognize at least rat Scn1a, human SCN1A and also mouse Scn1a) diluted at 1:250 in PBS/BSA 0.1%. After equilibrating the plate for 5 min at 21° C., the cells will be washed three times for 5 min each with PBS then incubated with goat anti-rabbit antibody diluted 1:200 in PBS/BSA 0.1% for 30 min at 21° C. The cells will be washed three times for 5 min with PBS and then incubated with 300 μl of Vectastain Elite ABC reagent A+B solution (Vector Laboratories cat # PK-6101) for 30 min; the Vectastain Elite ABC reagent A+B solution will be prepared at 21° C. 30 min before incubation with the cells by adding and mixing successively 2 drops of reagent A to 5 ml of PBS and then 2 drops of reagent B. The cells will be washed 3 times for 5 min with PBS at 21° C. and then incubated with tetramethylbenzidine (TMB) peroxidase substrate solution (Thermo Scientific cat # N301). After the supernatant turns blue, it will be transferred to a new 96 well ELISA plate (Greiner bio one cat #65121) and 1 M sulfuric acid will be added. The absorbance will be read at 450 nm using a Multiskan Spectrum spectrophotometer (Thermo Scientific). The background signal, read in the wells stained with a rabbit anti-mouse IgG as primary antibody (Abcam cat # ab6709) will be subtracted from all SCN1A and actin readings. Rabbit anti-actin antibody from Abcam (cat # ab1801) will be used. The SCN1A signal will be normalized to actin signal for each condition and normalized values for each experimental variant will be compared.

In embodiments, SCN1A expression (e.g., mRNA or protein) in a sample (e.g., cells or tissues in vivo or in vitro) treated using a small molecule of the invention is evaluated by comparison with SCN1A expression in a control sample. For example, expression of the protein or nucleic acid can be compared using methods known to those of skill in the art with that in a mock-treated or untreated sample. Alternatively, comparison with a sample treated with a control inactive molecule can be made depending on the information desired. In another embodiment, a difference in the expression of the SCN1A protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of SCN1A mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of SCN1A mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

In addition to changes in SCN1A protein or mRNA expression, changes in the function of the Nav1.1 channel can be quantified. For example, changes in the sodium current amplitude induced by SCN1A upregulation by small compounds can be measured in dissociated hippocampal interneurons. To achieve this, hippocampal GAD-positive bipolar cells (GABAergic interneurons) will be dissociated from 11- to 16-d-old rats by digestion with pronase and then thermolysin in a buffer continuously oxygenated with 95% $O_2$ and 5% $CO_2$. Dissociated cells will be plated in tissue culture dishes and treated with selected small compounds for 24 h after which electrophysiological recordings will be performed. Currents will be recorded using the whole-cell patch-clamp technique with an EPC-9 patch-clamp amplifier (HEKA). Patch pipettes will be made using a model P-97 Flaming-Brown micropipette puller (Sutter Instrument). Stimulation and data acquisition will be performed using PULSE program (version 7.5; HEKA Elektronik). For voltage clamp experiments the perfusion buffer containing, in mm: 19.1 NaCl, 19.1 tetraethylammonium chloride, 0.95 $BaCl_2$, 1.90 $MgCl_2$, 52.4 CsCl, 0.1 $CdCl_2$, 0.95 $CaCl_2$, 9.52 HEPES, 117 glucose, pH 7.35 will be constantly perfused over the cells using peristaltic pump. The patch pipette will contain, in mm: 157 N-methyl-d-glucamine, 126 HCl, 0.90 NaCl, 3.60 $MgCl_2$, 9.01 EGTA, 1.80 ATP-$Na_2$, 9.01 HEPES, 4.50 creatine-phosphate, pH 7.2. The cells will be held at −100 mV and depolarizing steps from −60 mV to −15 mV will be applied in 5 mV increments. Maximal current density will be determined and compared between treated and untreated neurons.

In addition, changes in the sodium current characteristics induced by SCN1A upregulation in hippocampal interneurons can be assessed. Hippocampal GAD-positive bipolar cells (GABAergic interneurons) will be dissociated from 11- to 16-d-old rats by digestion with pronase and then thermolysin in a buffer continuously oxygenated with 95% $O_2$ and 5% $CO_2$. Dissociated cells will be plated in tissue culture dishes and treated with selected small compounds for 24 h after which electrophysiological recordings will be performed. Currents will be recorded using the whole-cell patch-clamp technique with an EPC-9 patch-clamp amplifier (HEKA). Patch pipettes will be made using a model P-97 Flaming-Brown micropipette puller (Sutter Instrument). Stimulation and data acquisition will be performed using PULSE program (version 7.5; HEKA Elektronik). For voltage clamp experiments the perfusion buffer containing, in mm: 19.1 NaCl, 19.1 tetraethylammonium chloride, 0.95 $BaCl_2$, 1.90 $MgCl_2$, 52.4 CsCl, 0.1 $CdCl_2$, 0.95 $CaCl_2$, 9.52 HEPES, 117 glucose, pH 7.35 will be constantly perfused over the cells using peristaltic pump. The patch pipette will contain, in mm: 157 N-methyl-d-glucamine, 126 HCl, 0.90 NaCl, 3.60 $MgCl_2$, 9.01 EGTA, 1.80 ATP-$Na_2$, 9.01 HEPES, 4.50 creatine-phosphate, pH 7.2. The cells will be held at −100 mV and depolarizing steps from −60 mV to −15 mV will be applied in 5 mV increments. Activation curves (conductance/voltage relationships) will be calculated from current/voltage relationships according to $g=I_{Na}/(V-E_{Na})$, where $I_{Na}$ represents the peak sodium current measured at potential V, and E, represents the equilibrium potential. Boltzmann function will be fitted to normalized activation and inactivation curves and the curve characteristics will be determined. Inactivation time constants will be evaluated by fitting the current decay with single exponential function. Activation and inactivation profiles will be compared between treated and untreated cells to determine if treatment changed current characteristics. For current clamp experiments cells will be held at −80 mV, and their firing patterns will be recorded after 800 ms pulses applied in increments of 10 pA. The electrode buffer will contain, in mm: 135 potassium gluconate, 20 KCl, 2 $MgCl_2$, 2 $ATPNa_2$, 0.3 GTP-Na, and 10 HEPES, 0.2 EGTA, pH 7.3. The perfusion buffer will contain, in mm: 140 NaCl, 5 KCl, 2 $CaCl_2$, 1 MgCl2, 10 HEPES, and 10 glucose, pH adjusted to 7.4 with NaOH. The input-output relationship (number of action potentials/pA injected), action potential half-width, spike amplitude, and spike decrement will be measured and compared between treated and untreated hippocampal inhibitory interneurons. Single channel current recordings will be performed in an outside/out patch configuration using the same solutions and protocols as described above for whole cell patch recordings.

SCN1A up-regulation induced by treatment with small compounds may also influence intracellular sodium levels. Such changes may be assessed in the following experiments. Cells will be grown in a 96 well plate and dosed with varying concentrations of small compounds. After 48 h, the cells will be washed with Locke's buffer (8.6 mM HEPES, 5.6 mM KCl, 154 mM NaCl, 5.6 mM glucose, 1.0 mM $MgCl_2$, 2.3 mM $CaCl_2$, 0.0001 mM glycine, pH 7.4). The fluorescence background will be measured prior to loading the dye inside the cells. The dye will be loaded inside the cells by incubating the cells with the dye for 1 h at 37° C. with 10 μM SBFI-AM (dye binding to $Na^{+}$), 0.04% Pluronic F-127 Molecular Probes, OR, USA) and 2.5 mM probenecid in Locke's buffer (50 μl/well). At this time, cells will be washed twice with 2.5 mM probenecid in Locke's buffer (150 μl/well). Plates containing the loaded cells will be placed inside a reader such as a FLEXstation™ II (Molecular Devices, Sunnyvale, Calif., USA). The cells loaded with the dye will be excited at 340 nm and 380 nm; the emission signal will be recorded at 505 nm. The signal base line will be measured at this time. After measuring the signal base line, monensin (EMD, Gibbstown, N.J., USA, cat #475895) or gramicidin (EMD, Gibbstown, N.J., USA, cat #368020-25MG will be added to individual wells with cells as positive controls. TTX (1 uM) treatment will be used as negative control. Then relative expression of active SCN1A at the plasma membrane in the cells pre-treated with active compounds compared to vehicle control will be established. The signals will be calculated as a ratio of the emission at 505 nm to 340 nm/380 nm using Excel software.

Effect of SCN1A up-regulation on sodium levels may also be assessed in a single cell. Cells will be grown on a cover slide or in a 96 well plate and dosed with varying concentrations of small compounds. After 48 h, the cells will be washed with Locke's buffer (8.6 mM HEPES, 5.6 mM KCl, 154 mM NaCl, 5.6 mM glucose, 1.0 mM $MgCl_2$, 2.3 mM $CaCl_2$, 0.0001 mM glycine, pH 7.4). The fluorescence background will be measure prior to loading the dye inside the cells. The dye will be loaded by incubating the cells with the dye for 1 h at 37° C. with 10 M SBFI-AM (dye binding to Nat), 0.04% pluronic acid F-127 and 2.5 mM probenecid in Locke's buffer (50 μl/well). At this time, cells will be washed twice with 2.5 mM probenecid in Locke's buffer (150 μl/well). The cells in the 96 well plate or on a coverslide will be placed under a epi-fluorescent microscope equipped with Hg lamp and appropriate filters for excitation and emission (from Omega Optical Inc, Brattleboro, Vt., USA cat # set X-F04-2 or from Chroma Technology Corp, Bellows Falls, Vt., USA, cat #79001). The cells loaded with the dye will be excited at 340 nm and 380 nm; the emission signal will be recorded at 505 nm. After measuring the signal base line, monensin (EMD, Gibbstown, N.J., USA, cat #475895) or gramicidin (EMD, Gibbstown, N.J., USA, cat #368020-25MG) will be added to individual wells with cells as positive control. In order to establish relative up-regulation of active SCN1A at the plasma membrane the cells pre-treated with the active compounds will be compared to vehicle controls. The data will be collected by a camera connected to the epi-fluorescente microscope and quantified using the appropriate software. The raw signals will be processed by calculating the ratio of the 505 nm emissions to 340 nm/380 nm using Excel software.

In addition to cellular assays, animal models of a particular disease state may be utilized. In each case, the animal will be selected based upon the particular target disease or condition. The animals are known to express or are able to express the SCN1A polypeptide or variant thereof. The compounds of the present invention can be utilized for diagnostics, therapeutics, and prophylaxis, and as research reagents and components of kits. Furthermore, compounds, which are able to modulate gene expression are often used by those of ordinary skill to elucidate the function of particular genes or to distinguish between functions of various members of a biological pathway. Use of the compounds in the manufacture of a medicament to treat any of the diseases recited herein is a feature of the claimed invention.

For use in kits and diagnostics and in various biological systems, the compounds of the present invention, either alone or in combination with other compounds or therapeutics, are useful as tools in differential and/or combinatorial analyses to elucidate interdependent expression patterns of a portion or the entire complement of genes expressed within cells and tissues.

As used herein the term "biological system" or "system" is defined as any organism, cell, cell culture or tissue that expresses, or is made competent to express products of the sodium channel, voltage-gated, alpha subunit (SCNxA) family of genes. These include, but are not limited to, humans, transgenic animals, cells, cell cultures, tissues, xenografts, transplants and combinations thereof.

As one non limiting example, expression patterns within cells or tissues treated with one or more compounds are compared to control cells or tissues not treated with such compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

For therapeutics, an animal, preferably a human, suspected of having a disease or disorder which can be treated by modulating the expression of sodium channel, voltage-gated, type I, alpha subunit (SCN1A) polynucleotides or proteins is treated by administering the compounds in accordance with this invention. For example, in one non-limiting embodiment, the methods comprise the step of administering to the animal in need of treatment, a therapeutically effective amount of sodium channel, voltage-gated, type 1, alpha subunit (SCN1A) modulator. The sodium channel, voltage-gated, type I, alpha subunit (SCN1A) modulators of the present invention effectively modulate the activity of the sodium channel, voltage-gated, type I, alpha subunit (SCN1A) or modulate the expression of the sodium channel, voltage-gated, type I, alpha subunit (SCN1A) protein. In one embodiment, the activity or expression of sodium channel, voltage-gated, type I, alpha subunit (SCN1A) in an animal is inhibited by about 10% as compared to a control. Preferably, the activity or expression of SCN1A in an animal is inhibited by about 30%. More preferably, the activity or expression of Sodium channel, voltage-gated, type I, alpha subunit (SCN1A) in an animal is inhibited by 50% or more. Thus, the small compounds modulate expression of sodium channel, voltage-gated, type 1, alpha subunit (SCN1A) mRNA or protein by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Sodium channel, voltage-gated, type I, alpha subunit (SCN1A) and/or in an animal is increased by about 10% as compared to a control. Preferably, the activity or expression of Sodium channel, voltage-gated, type 1, alpha subunit (SCN1A) in an animal is increased by about 30%. More preferably, the activity or expression of Sodium channel, voltage-gated, type I, alpha subunit (SCN1A) in an animal is increased by 50% or more. Thus, the compounds modulate expression of Sodium channel, voltage-gated, type I, alpha subunit (SCN1A) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% or more as compared to a control.

For example, the reduction or increase in/of the expression of sodium channel, voltage-gated, type I, alpha subunit (SCN1A) may be measured in blood, adipose tissue, liver or any other body fluid, tissue or organ of the animal. Preferably, the cells contained within said fluids, tissues or organs being analyzed contain a nucleic acid molecule encoding sodium channel, voltage-gated, type I, alpha subunit (SCN1A) peptides and/or the sodium channel, voltage-gated type I, alpha subunit (SCN1A) protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

In an embodiment, invention practice involves administering at least one of the foregoing compounds to a patient in need of treatment thereof: milnacipran, torsemide, risperidone, pinacidil, benidipine, ketoconazole, ebselen, tadalafil, zeranol, nefazadone, lomerizine, icariin, omeprazole, esomeprazole, L-694,247, nitrendipine, nimetazepam, amlexanox, mosapride, sertraline or stanozolol or pharmaceutically acceptable salts, isomers, enantiomers, isoforms, polymorphs, hydrates, solvates or prodrugs thereof.

The compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

The present invention also includes pharmaceutical compositions and formulations that include the compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid.

When it is intended that the compounds of the present invention are to be administered to cells in the central nervous system, administration can be with one or more agents capable of promoting penetration of the subject compound across the blood-brain barrier. Administration can be rapid as by injection or made over a period of time as by slow infusion or administration of slow release formulations.

The subject compounds can also be linked or conjugated or combined with agents that provide desirable pharmaceutical or pharmacodynamic properties. For example, the compounds can be coupled to any substance, known in the art to promote penetration or transport across the blood-brain barrier, such as an antibody to the transferrin receptor, and administered by intravenous injection. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(−) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," 6,294,520, "Material for passage through the blood-brain barrier," and 6,936,589, "Parenteral delivery systems," all incorporated herein by reference in their entirety.

The subject compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate compound uptake. One such composition shown to facilitate uptake is LIPOFECTIN (available from GIBCO-BRL, Bethesda, Md.).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposome slacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of the small molecules. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the compounds of the invention for the uses recited herein are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoyl-phosphatidyl ethanolamine DOTMA).

For topical or other administration, the compounds of the invention may be encapsulated within liposomes or may form complexes thereto, in particular to cationic liposomes. Alternatively, compounds may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compounds of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Compounds of the invention may be delivered orally, in granular form including sprayed dried panicles, or complexed to form micro or nanoparticles.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more compounds and one or more other active pharmaceutical ingredients. Examples of such active pharmaceutical ingredients include but are not limited to any active ingredient that is useful to treat a condition of the patient in need of treatment with a compound of the invention. Two or more combined compounds may be used together or sequentially.

In another related embodiment, compositions of the invention may contain one or more compounds, targeted to a first nucleic acid target and one or more additional compounds targeted to a second nucleic acid target. For example, the first target may be a particular antisense sequence of sodium channel, voltage-gated, type I, alpha subunit (SCN1A), and the second target may be a region from another nucleotide sequence. Alternatively, compositions of the invention may contain two or more compounds that modulate different regions of the same sodium channel, voltage-gated, type I, alpha subunit (SCN1A) nucleic acid or protein target. Two or more combined compounds may be used together or sequentially.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual active pharmaceutical ingredients, and can generally be estimated based on EC50s found to be effective in in vitro and in vivo animal models and can also be determined from the prescribing information for each of the approved and marketed drugs. In general, dosage is from 0.01 μg to 100 mg per kg of body weight, and may be given once or more daily, weekly or monthly. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the compound is administered in maintenance doses, ranging from 0.01 μg to 100 mg per kg of body weight, once or more daily.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is “prior art” to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention. The following compounds were used to assess modulation of the levels of SCN1A mRNA:

a) Milnacipran HCl (1R(S),2S(R)[-2-(aminomethyl)-N,N-diethyl-1-phenylcyclopropanecarboxamide hydrochloride);

b) Torsemide (1-isopropyl-3-[(4-m-toluidino-3-pyridyl-sulfonyl]urea);

c) Risperidone (3-[2-[4-(6-flouro-1,2-benzisoxazol-3-yl)-1-piperidinyl]-ethyl]-6,7,8,9-tetrahydro-2-methyl-4H-pyrido[,2-a]pyrimidin-4-one);

d) Pinacidil (N-cyano-N'pyridin-4-yl-N"-(1,2,2-trimethylpropyl)guanidine);

e) Benedipine HCl (5-Omethyl-3O-[(3R)-1-(phenylmethyl)-piperidin-3-yl]2,6-dimethyl-4-(3-nitrophenyl)-1,4-dihydropyridine-3,5-dicarboxylate);

f) Ketoconazole (1-[4-(4-{[(2R,4S)-2-(2,4-Dichlorophenyl)-2-(1H-imidazol-1-ylmethyl)-1,3-dioxolan-4-yl]methoxy}phenyl)piperazin-1-ylethan-1-one);

g) Ebselen (2-Phenyl-1,2-benzoselenazol-3-one);

h) Tadalafil ((6R-trans)-6-(1,3-benzodioxol-S-yl)-2,3,6,7,12,12a-hexahydro-2-methyl-pyrazino[1',2':1,6]pyrido[3,4-b]indole-1,4-dione);

i) Zeranol ((3S,7R)-7,14,16-trihydroxy-3-methyl-3,4,5,6,7,8,9,10,11,12-decahydro-1H-2-benzoxacyclotetradecin-1-one);

j) Nefazadone HCl (2-[3-[4-(3-chlorophenyl)-1-piperazinyl]propyl]-5-ethyl-2,4-dihydro-4-(2-phenoxyethyl)-3H-1,2,4-triazol-3-one monohydrochloride;

k) Lomerizine dihydrochloride (1-[bis(4-fluorophenyl)methyl]-4-[2,3,4-trimethoxyphenylmethyl]Dihydrochloride);

l) Icariin (5-hydroxy-2-(4-methoxyphenyl)-8-(3-methylbut-2-enyl)-7-[(2S,3R,4S,5S,6R)-3,4,5-trihydroxy-6-(hydroxymethyl)oxan-2-yl]oxy-3-[(2S,3R,4R,5R,6S)-3,4,5-trihydroxy-6-methyloxan-2-yl]oxychromen-4-one);

m) Omeprazole magnesium (6-methoxy-2-((4-methoxy-3,5-dimethylpyridin-2-yl)methylsulfinyl)-1H-benzo[d]imidazole Mg);

n) Esomeprazole magnesium ((S)-6-methoxy-2-((4-methoxy-3,5-dimethylpyridin-2-yl)methylsulfinyl)-1H-benzo[d]imidazole Mg);

o) L-694,247 (Methanesulfonamide,N-[4-[[5-[3-(2-aminoethyl)-1H-indol-5-yl]-1,2,4-oxadiazol-3-yl]methyl]phenyl];

p) Nitrendipine ((RS)-ethyl methyl 2,6-dimethyl-4-(3-nitrophenyl)-1,4-dihydropyridine-3,5-dicarboxylate);

q) Nimetazepam (2-methyl-9-nitro-6-phenyl-2,5-diazabicyclo[5.4.0]undeca-5,8,10,12-tetraen-3-one);

r) Amlexanox (2-amino-7-isopropyl-5-oxo-5H-chromeno[2,3-b]pyridine-3-carboxylic acid);

s) Mosapride citrate (4-Amino-5-chloro-2-ethoxy-N-[[4-[4-fluorophenyl)methyl)]-2-morpholinyl]methyl]-benzamide 2-hydroxy-1,2,3-propanetricarboxylate);

t) Sertraline hydrochloride ((1S,4S)-4-(3,4-dichlorophenyl)-N-methyl-1,2,3,4-tetrahydronaphthalen-1-amine) and u) Stanozolol (17β-Hydroxy-17-methyl-5α-androstano[3,2-c]-pyrazole).

Example 1. Upregulation of SCN1A mRNA in Primary Human Fibroblasts Carrying Dravet-Associated Mutation after Treatment with Small Compounds In Example 1 primary human skin fibroblasts carrying Dravet-associated SCN1A mutation were treated with small compounds at a final concentration of 1 uM. The data below shows that after 24-48 h treatment these compounds were able to upregulate SCN1A mRNA.

Materials and Methods

Treatment of Primary Human Fibroblasts Carrying a Dravet-Associated Mutation with Small Compounds.

Primary human skin fibroblasts carrying Dravet-associated SCN1A mutation introduced into culture by Dr. N. Kenyon (University of Miami) were grown in Growth Media consisting of a-MEM (Gibco, cat: 12561-056)+10% FBS (Mediatech, cat: 35-015 CV)+1% Antimycotic-Antibiotic (Gibco, cat: 15240-062) at 37° C. and 5% $CO_2$. One day before the experiment cells were plated at the density of approximately $4\times10^4$/well into 24 well plates in Growth Media and incubated at 37° C. and 5% $CO_2$ overnight. Next day, the media in the 24 well plates was changed to fresh Growth Media (I ml/well) and the cells were dosed with small compounds. All compounds were available from commercial sources. Compound stocks were prepared in DMSO at a concentration of 1 mM. At the time of the experiment 1 mM stock solutions were diluted to the concentration of 1 uM in Growth Media. One in 1000 dilution of DMSO was used for the control wells. After 24-48 h incubation at 37° C. and 5% $CO_2$ the media was removed and RNA was extracted from the cells using SV Total RNA Isolation System from Promega (cat # Z3105) following the manufacturers' instructions. Six hundred nanograms of purified total RNA was added to the reverse transcription reaction performed using SuperScript VILO cDNA Synthesis Kit from Invitrogen (cat #11754-250) as described in the manufacturer's protocol. The cDNA from this reverse transcription reaction was used to monitor gene expression by real time PCR using ABI Taqman Gene Expression Mix (cat #4369510) and primers/probes designed by ABI (assays Hs00374696_ml, Hs00897350_ml or Hs00897341_ml for human SCN1A). Results obtained using all three assays were very similar (data not shown). The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat #4319413E). Fold change in gene expression after treatment with compounds was calculated based on the difference in 18S-normalized dCt values between compound- and vehicle-treated samples.

Results

The results showed that small compounds of different chemistry were able to upregulate SCN1A mRNA 2-4 fold in primary skin fibroblasts carrying a Dravet-associated mutation (Table 1).

Example 2. Upregulation of SCN1A mRNA in Adult Primary Human Keratinocytes after Treatment with Small Compounds In Example 2 primary human keratinocytes were treated with small compounds at a final concentration of 1 uM. The data below shows that after 24-48 h treatment these compounds were able to upregulate SCN1A mRNA.

Materials and Methods

Treatment of Primary Human Keratinocytes with Small Compounds.

Adult primary human keratinocytes from PromoCell (Heidelberg, Germany, cat # C-12003) or LifeLine Cell Technology (Frederick, Md., cat # FC-0025) were grown in Growth Media supplied by the manufacturers at 37° C. and 5% $CO_2$. One day before the experiment cells were plated at the density of approximately $4\times10^4$/well into 24 well plates in Growth Media and incubated at 37° C. and 5% $CO_2$ overnight. Next day, the media in the 24 well plates was changed to fresh Growth Media (1 ml/well) and the cells were dosed with small compounds. All compounds were available from commercial sources.

Compound stocks were prepared in DMSO at a concentration of 1 mM. At the time of the experiment 1 mM stock solutions were diluted to the concentration of 1 uM in Growth Media. One in 1000 dilution of DMSO was used for the control wells. After 24-48 h incubation at 37° C. and 5% $CO_2$ the media was removed and RNA was extracted from the cells using SV Total RNA Isolation System from Promega (cat # Z3105) following the manufacturers' instructions. Six hundred nanograms of purified total RNA was added to the reverse transcription reaction performed using SuperScript VILO cDNA Synthesis Kit from Invitrogen (cat #11754-250) as described in the manufacturer's protocol. The cDNA from this reverse transcription reaction was used to monitor gene expression by real time PCR using ABI Taqman Gene Expression Mix (cat #4369510) and primers/probes designed by ABI (assays Hs00374696_ml, Hs00897350_ml or Hs00897341_ml for human SCN1A). Results obtained using all three assays were very similar (data not shown). The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat #4319413E). Fold change in gene expression after treatment with compounds was calculated based on the difference in 18S-normalized dCt values between compound- and vehicle-treated samples.

Results

The results showed that small compounds of different chemistry were able to upregulate SCN1A mRNA 2-5 fold in adult primary keratinocytes (Table 1).

Table shows fold increase in SCN1A mRNA levels in primary skin fibroblasts carrying a Dravet-associated mutation (Column 1) and adult primary keratinocytes (Column 2) after treatment with small compounds at a concentration of 1 uM. Avg—average upregulation; STE—standard error of the mean.

TABLE 1

| | SCN1A fibroblasts | | Keratinocytes | | |
|---|---|---|---|---|---|
| Name | Avg | STE | Avg | STE | Description |
| Milnacipran | 4.37 | 3.07 | 2.72 | 0.04 | SNRI, for fibromyalgia |
| Torsemide | 3.70 | 3.44 | | n/a | Diuretic |
| Risperidone | 3.48 | n/a | 3.02 | 1.01 | Atypical antipsychotic |
| Pinacidil | 3.48 | 1.83 | | n/a | K+ channel opener, antihypertensive |
| Benidipine | 3.01 | 1.16 | 1.69 | n/a | Ca2+ channel blocker, for hypertension |

TABLE 1-continued

| | SCN1A fibroblasts | | Keratinocytes | | |
|---|---|---|---|---|---|
| Name | Avg | STE | Avg | STE | Description |
| Ketoconazole | 2.95 | n/a | 2.73 | 0.34 | Antifungal |
| Ebselen | 2.81 | n/a | 2.67 | 0.53 | Antioxidant, for stroke |
| Tadalafil | 2.73 | n/a | 2.79 | 1.37 | Cialis |
| Zeranol | 2.60 | 0.87 | 4.51 | n/a | Non-steroidal estrogen agonist, for livestock growth |
| Nefazadone | 2.39 | 0.32 | 4.53 | 2.22 | Antidepressant |
| Lomerizine | 2.39 | 0.41 | 3.47 | 0.93 | Ca2+ channel blocker, antimigraine |
| Icariin | 2.38 | 0.23 | 2.29 | 1.02 | Stimulant, Yin Yang Huo |
| Omeprazole | 2.22 | 0.50 | 2.46 | 0.03 | Proton pump inhibitor, for dyspepsia |
| L-694,247 | 2.20 | 0.27 | 1.68 | 0.02 | 5-HT1D receptor agonist |
| Nitrendipine | 2.13 | 0.56 | | n/a | Ca2+ channel blocker, for hypertension |
| Nimetazepam | 2.03 | 0.24 | 2.47 | n/a | GABA agonist, hypnotic, anticonvulslant |
| Amlexanox | 2.01 | 0.09 | 5.41 | n/a | Histamine inhibitor, antiallergic |
| Mosapride | 1.90 | n/a | 1.47 | n/a | 5HT4 agonist, gastrokinetic |
| Sertraline | 1.79 | 0.31 | 5.18 | 2.54 | Antidepressant (Zoloft) |
| Stanozolol | 1.75 | n/a | 1.76 | 0.59 | Anabolic steroid |

Example 3. Quantification of the SCN1A Protein by Immunohistochemistry

The purpose of this experiment is to rank compounds according to their ability to upregulate the SCN1A protein expression in different cells using a technique called immunohistochemistry.

Materials and Methods.

SCN1A protein will be detected inside cells by immunohistochemistry. To achieve this, the cells will be grown in 24-well plates using appropriate growth conditions. Forty eight hours after addition of small compounds, the media will be removed and the cells will be washed 3 times with Dulbecco's phosphate-buffered saline without calcium and magnesium (PBS) (Mediatech cat #21-031-CV). Then PBS will be discarded and the cells will be fixed in the 24 well plate using 300 μl of 100% methanol for 15 min at −20° C. After removing the methanol and washing with PBS, the cells will be incubated with 3% hydrogen peroxide (Fisher Chemical cat # H325-100) for 5 min at 21° C. The cells will be washed three times for 5 min with PBS, then incubated with 300 μl of bovine serum albumin (BSA) (Sigma cat # A-9647) at 0.1% in PBS for 30 min at 21° C. The cells will be washed three times for 5 min with PBS then incubated with 300 μl of avidin solution (Vector Laboratories cat # SP-2001) for 30 min at 21° C. The cells will be briefly rinsed three times with PBS then incubated with biotin solution (Vector Laboratories cat # SP-2001) for 30 min at 21° C. The cells will be washed three times with PBS and then incubated overnight at 4° C. with 300 μl per well of rabbit antibody raised against a synthetic peptide (EEQKKYYNAMKKLGSKKP) corresponding to C terminal amino acids 1491-1508 of rat Scn1a (Abcam cat # ab24820; known to recognize rat Scn1a, human SCN1A and mouse Scn1a) diluted at 1:250 in PBS/BSA 0.1%. After equilibrating the plate for 5 min at 21° C., the cells will be washed three times 5 min each with PBS then incubated with goat anti-rabbit antibody diluted 1:200 in PBSIBSA 0.1% for 30 min at 21° C. The cells will be washed three times for 5 min with PBS and then incubated with 300 μl of Vectastain Elite ABC reagent A+B solution (Vector Laboratories cat # PK-6101) for 30 min; the Vectastain Elite ABC reagent A+B solution will be prepared at 21° C. 30 min before incubation with the cells by adding and mixing successively 2 drops of reagent A to 5 ml of PBS and then 2 drops of reagent B. The cells will be washed 3 times for 5 min each with PBS at 21° C. and then incubated with Diaminobenzidine (DAB) peroxidase substrate solution (Vector Laboratories cat # SK-4105) until cells are stained, the DAB peroxidase substrate solution will be reconstituted before being added to the cells by mixing 1 ml of ImmPACT™ DAB Diluent with 30 μl of ImmPACPT™ DAB Chromogen concentrate. At this time, the cells will be briefly washed three times with PBS and 300 μl of PBS will be left in each well. The staining of the cells will be analyzed directly inside the wells of the 24-well plate using an inverted Nikon Eclipse TS100 microscope equipped with a Nikon DS-Ril camera coupled with Nikon Digital-Sight equipment on the screen of a Dell Latitude D630 laptop. Photos of individual wells will be made using the software provided with the Nikon camera, the NIS-Elements D 3.0.

Example 4. Quantification of the SCN1A Protein by Enzyme-Linked Immunosorbent Assay (ELISA)

The purpose of this experiment is to rank compounds according to their ability to upregulate the SCN1A protein expression in different cells using a technique called enzyme-linked immunosorbent assay (ELISA).

Materials and Methods:

Amounts of SCN1A protein produced by the cells will be quantified by ELISA. To achieve this, the cells will be grown in 24-well plates using appropriate growth conditions. Forty eight hours after addition of small compounds, the media will be removed and the cells will be washed 3 times with Dulbecco's phosphate-buffered saline without calcium and magnesium (PBS) (Mediatech cat #21-031-CV). Then PBS will be discarded and the cells will be fixed in the 24 well plate using 100 μl of 100% methanol for 15 min at −20° C. After removing the methanol and washing with PBS, the cells will be incubated with 3% hydrogen peroxide (Fisher Chemical cat # H325-100) for 5 min at 21° C. The cells will be washed three times for 5 min with PBS, then incubated with 100 μl of bovine serum albumin (BSA) (Sigma cat # A-9647) at 0.1% in PBS for 30 min at 21° C. The cells will be washed three times for 5 min with PBS then incubated with 300 μl of avidin solution (Vector Laboratories cat # SP-2001) for 30 min at 21° C. The cells will be briefly rinsed three times with PBS then incubated with biotin solution (Vector Laboratories cat # SP-2001) for 30 min at 21° C. The cells will be washed three times with PBS and then incubated overnight at 4° C. with 100 μl per well of rabbit antibody raised against a synthetic peptide (EEQKKYY-NAMKKLGSKKP) corresponding to C terminal amino acids 1491-1508 of rat Scn1a (Abcam cat # ab24820; known to recognize at least rat Scn1a, human SCN1A and also mouse Scn1a) diluted at 1:250 in PBS/BSA 0.1%. After equilibrating the plate for 5 min at 21° C., the cells will be washed three times for 5 min each with PBS then incubated with goat anti-rabbit antibody diluted 1:200 in PBS/BSA 0.1% for 30 min at 21° C. The cells will be washed three times for 5 min with PBS and then incubated with 300 μl of Vectastain Elite ABC reagent A+B solution (Vector Laboratories cat # PK-6101) for 30 min; the Vectastain Elite ABC reagent A+B solution will be prepared at 21° C. 30 min before incubation with the cells by adding and mixing successively 2 drops of reagent A to 5 ml of PBS and then 2 drops of reagent B. The cells will be washed 3 times for 5 min with PBS at 21° C. and then incubated with tetramethylbenzidine (TMB) peroxidase substrate solution (Thermo Scientific cat # N301). After the supernatant turns blue, it will be transferred to a new 96 well ELISA plate (Greiner bio one cat #65121) and 1 M sulfuric acid will be added. The absorbance will be read at 450 nm using a Multiskan Spectrum spectrophotometer (Thermo Scientific). The background signal, read in the wells stained with a rabbit anti-mouse IgG as primary antibody (Abcam cat # ab6709) will be subtracted from all SCN1A and actin readings. Rabbit anti-actin antibody from Abcam (cat # ab1801) will be used. The SCN1A signal will be normalized to actin signal for each condition and normalized values for each experimental variant will be compared.

Example 5. Quantification of the ACTIN mRNA

The purpose of this experiment is to ensure that none of the compounds up-regulating SCN1A mRNA have any effect on the actin mRNA in different cells using a technique called real-time PCR.

Materials and Methods.

Total RNA will be harvested from cells grown in the appropriate culture conditions.

To achieve this, 48 h after addition of small compounds the media will be removed and RNA will be extracted from the cells using SV Total RNA Isolation System from Promega (cat # Z3105) or RNeasy Total RNA Isolation kit from Qiagen (cat #74181) following the manufacturers' instructions. Six hundred nanograms of RNA will be added to the reverse transcription reaction performed using Verso cDNA kit from Thermo Scientific (cat # AB1453B) or High Capacity cDNA Reverse Transcription Kit (cat #4368813) or SuperScript VILO cDNA Synthesis Kit from Invitrogen (cat #11754-250) as described in the manufacturer's protocol. The cDNA from this reverse transcription reaction will be used to monitor gene expression by real time PCR using ABI Taqman Gene Expression Mix (Applied Biosystems Inc., Foster City Calif., cat #4369510) and specific primers/probes for actin designed by ABI (Applied Biosystems Taqman Gene Expression Assay for human actin cat # Hs99999903_ml*, monkey actin cat # Rh03043379_gH or mouse actin cat # Mm00607939_s1*). The following PCR cycle will be used: 50° C. for 2 min, 95° C. for 10 min, 40 cycles of (95° C. for 15 seconds, 60° C. for 1 min) using StepOne Plus Real Time PCR Machine (Applied Biosystems Inc., Foster City Calif.). Fold change in gene expression after treatment with antisense oligonucleotides will be calculated based on the difference in 18S-normalized dCt values between treated and mock-transfected samples.

Example 6. Quantification of the ACTIN Protein by Immunohistochemistry

The purpose of this experiment is to ensure that none of the compounds up-regulating SCN1A protein as seen by immunohistochemistry has any effect on the ACTIN protein detected under the same conditions. If the amounts of ACTIN protein are not changed by the compounds up-regulating SCN1A, we will assume that actin can be used in ELISA quantification of SCN1A protein as control for normalization.

Materials and Methods.

Actin protein will be detected inside cells by immunohistochemistry. To achieve this, 48 h after addition of small compounds, the media will be removed and the cells will be washed 3 times with Dulbecco's phosphate-buffered saline without calcium and magnesium (PBS) (Mediatech cat #21-031-CV). Then PBS will be discarded and the cells will be fixed in the 24 well plate using 300 μl of 100% methanol for 15 min at −20° C. After removing the methanol and washing with PBS, the cells will be incubated with 3% hydrogen peroxide (Fisher Chemical cat # H325-100) for 5 min at 21° C. The cells will be washed three times for 5 min with PBS, then incubated with 300 pt of bovine serum albumin (BSA) (Sigma cat # A-9647) at 0.1% in PBS for 30 min at 21° C. The cells will be washed three times for 5 min with PBS then incubated with 300 μl of avidin solution (Vector Laboratories cat # SP-2001) for 30 min at 21° C. The cells will be briefly rinsed three times with PBS then incubated with biotin solution (Vector Laboratories cat # SP-2001) for 30 min at 21° C. The cells will be washed three times with PBS and then incubated overnight at 4° C. with 300 μl per well of rabbit antibody raised against a synthetic peptide derived from within residues 350-450 of human actin (Abcam cat # ab1801; known to recognize beta and gamma human, mouse and rat actin) diluted at 1:250 in PBS/BSA 0.1%. After equilibrating the plate for 5 min at 21° C., the cells will be washed three times 5 min each with PBS then incubated with goat anti-rabbit antibody diluted 1:200 in PBS/BSA 0.1% for 30 min at 21° C. The cells will be washed three times for 5 min with PBS and then incubated with 300 μl of Vectastain Elite ABC reagent A+B solution (Vector Laboratories cat # PK-6101) for 30 min; the Vectastain Elite ABC reagent A+B solution will be prepared at 21° C. 30 min before incubation with the cells by adding and mixing successively 2 drops of reagent A to 5 ml of PBS and then 2 drops of reagent B. The cells will be washed 3 times for 5 min with PBS at 21° C. and then incubated with Diaminobenzidine (DAB) peroxidase substrate solution (Vector Laboratories cat # SK-4105) until cells are stained; the DAB peroxidase substrate solution will be reconstituted before being added to the cells by mixing 1 ml of ImmPACT™ DAB Diluent with 30 μl of ImmPACT™ DAB Chromogen concentrate. At this time, the cells will be briefly washed three times with PBS and 300 μl of PBS will be left in each well. The staining of the cells will be analyzed directly inside the wells of the 24-well plate using an inverted Nikon Eclipse TS100 microscope equipped with a Nikon DS-Ril camera coupled with Nikon Digital-Sight equipment on the screen of a Dell Latitude D630 laptop. Photos of individual wells will be made using the software provided with the Nikon camera, the NIS-Elements D 3.0.

Example 7. Changes in the Sodium Current Amplitude Induced by SCN1A Upregulation in Hippocampal Pyramidal Cell The purpose of this experiment is to ensure that the SCN1A protein up-regulated by the small compounds increases the amplitude of the sodium current in the hippocampal GABAergic interneurons, where it is shown to be affected in Dravet syndrome.

Materials and Methods.

Hippocampal GAD-positive bipolar cells (GABAergic interneurons) will be dissociated from 11- to 16-d-old rats by digestion with pronase and then thermolysin in a buffer continuously oxygenated with 95% $O_2$ and 5% $CO_2$. Dissociated cells will be plated in tissue culture dishes and treated with selected small compounds for 24 h after which electrophysiological recordings will be performed. Currents will be recorded using the whole-cell patch-clamp technique with an EPC-9 patch-clamp amplifier (HEKA). Patch pipettes will be made using a model P-97 Flaming-Brown micropipette puller (Sutter Instrument). Stimulation and data acquisition will be performed using PULSE program (version 7.5; H EKA Elektronik).

For voltage clamp experiments the perfusion buffer containing, in mm: 19.1 NaCl, 19.1 tetraethylammonium chloride, 0.95 $BaCl_2$, 1.90 $MgCl_2$, 52.4 CsCl, 0.1 $CdCl_2$, 0.95 $CaCl_2$, 9.52 HEPES, 117 glucose, pH 7.35 will be constantly perfused over the cells using peristaltic pump. The patch pipette will contain, in mm: 157 N-methyl-d-glucamine, 126 HCl, 0.90 NaCl, 3.60 $MgCl_2$, 9.01 EGTA, 1.80 ATP-$Na_2$, 9.01 HEPES, 4.50 creatine-phosphate, pH 7.2. The cells will be held at −100 mV and depolarizing steps from −60 mV to −15 mV will be applied in 5 mV increments. Maximal current density will be determined and compared between treated and untreated neurons.

Example 8. Changes in the Sodium Current Characteristics Induced by SCN1A Upregulation in Hippocampal Pyramidal Cells The purpose of this experiment is to ensure that the SCN1A protein up-regulated by the small compounds does not change the characteristics of the sodium current in the hippocampal GABAergic interneurons, where it is shown to be affected in Dravet syndrome.

Materials and Methods.

Hippocampal GAD-positive bipolar cells (GABAergic interneurons) will be dissociated from 11- to 16-d-old rats by digestion with pronase and then thermolysin in a buffer continuously oxygenated with 95% $O_2$ and 5% $CO_2$. Dissociated cells will be plated in tissue culture dishes and treated with selected small compounds for 24 h after which electrophysiological recordings will be performed. Currents will be recorded using the whole-cell patch-clamp technique with an EPC-9 patch-clamp amplifier (HEKA). Patch pipettes will be made using a model P-97 Flaming-Brown micropipette puller (Sutter Instrument). Stimulation and data acquisition will be performed using PULSE program (version 7.5; HEKA Elektronik). For voltage clamp experiments the perfusion buffer containing, in mm: 19.1 NaCl, 19.1 tetraethylammonium chloride, 0.95 $BaCl_2$, 1.90 $MgCl_2$, 52.4 CsCl, 0.1 $CdCl_2$, 0.95 $CaCl_2$, 9.52 HEPES, 117 glucose, pH 7.35 will be constantly perfused over the cells using peristaltic pump. The patch pipette will contain, in mm: 157 N-methyl-d-glucamine, 126 HCl, 0.90 NaCl, 3.60 $MgCl_2$, 9.01 EGTA, 1.80 ATP-$Na_2$, 9.01 HEPES, 4.50 creatine-phosphate, pH 7.2. The cells will be held at −100 mV and depolarizing steps from −60 mV to −15 mV will be applied in 5 mV increments. Activation curves (conductance/voltage relationships) will be calculated from current/voltage relationships according to $g=I_{Na}/(V-E_{Na})$, where Is, represents the peak sodium current measured at potential V, and $E_{Na}$ represents the equilibrium potential. Boltzmann function will be fitted to normalized activation and inactivation curves and the curve characteristics will be determined. Inactivation time constants will be evaluated by fitting the current decay with single exponential function. Activation and inactivation profiles will be compared between treated and untreated cells to determine if treatment changed current characteristics.

For current clamp experiments cells will be held at −80 mV, and their firing patterns will be recorded after 800 ms pulses applied in increments of 10 pA. The electrode buffer will contain, in mm: 135 potassium gluconate, 20 KCl, 2 $MgCl_2$, 2 $ATPNa_2$, 0.3 GTP-Na, and 10 HEPES, 0.2 EGTA, pH 7.3. The perfusion buffer will contain, in mm: 140 NaCl, 5 KCl, 2 CaCl2, 1 MgCl2, 10 HEPES, and 10 glucose, pH adjusted to 7.4 with NaOH. The input-output relationship (number of action potentials/pA injected), action potential half-width, spike amplitude, and spike decrement will be measured and compared between treated and untreated hippocampal inhibitory interneurons.

Single channel current recordings will be performed in an outside/out patch configuration using the same solutions and protocols as described above for whole cell patch recordings.

Example 9. Effect of SCN1A Up-Regulation on Intracellular Sodium Levels

The purpose of this experiment is to check if the up-regulation of SCN1A protein in cells leads to changes in the intracellular levels of sodium. Cells expressing different amounts of SCN1A after dosing with small compounds will be loaded with a dye specific for Na+. As a positive control for Na+ concentration changes inside the cells, monensin and gramicidin which are Na+ ionophores, will be used.

Materials and Methods.

Cells will be grown in a 96 well plate and dosed with varying concentrations of small compounds. After 48 h, the cells will be washed with Locke's buffer (8.6 mM HEPES, 5.6 mM KCl, 154 mM NaCl, 5.6 mM glucose, 1.0 mM $MgCl_2$, 2.3 mM $CaCl_2$, 0.0001 mM glycine, pH 7.4). The fluorescence background will be measured prior to loading the dye inside the cells. The dye will be loaded inside the cells by incubating the cells with the dye for 1 h at 37'C with 10 μM SBFI-AM (dye binding to $Na^+$), 0.04% Pluronic F-127 Molecular Probes. OR, USA) and 2.5 mM probenecid in Locke's buffer (50 μl/well). At this time, cells will be washed twice with 2.5 mM probenecid in Locke's buffer (150 μl/well). Plates containing the loaded cells will be placed inside a reader such as a FLEXstation™ II (Molecular Devices, Sunnyvale, Calif., USA). The cells loaded with the dye will be excited at 340 nm and 380 nm; the emission signal will be recorded at 505 nm. The signal base line will be measured at this time. After measuring the signal base line, monensin (EMD, Gibbstown, N.J., USA, cat #475895) or gramicidin (EMD, Gibbstown, N.J., USA, cat #368020-25MG will be added to individual wells with cells as positive controls. TTX (1 uM) treatment will be used as negative control. Then relative expression of active SCN1A at the plasma membrane in the cells pre-treated with active compounds compared to vehicle control will be established.

The signals will be calculated as a ratio of the emission at 505 nm to 340 nm/380 nm using Excel software.

Example 10. Effect of SCN1A Up-Regulation on Sodium Levels in a Single Cell

The purpose of this experiment is to check if the up-regulation of SCN1A protein in cells leads to changes in the intracellular levels of sodium in individual cells. Cells expressing different amounts of SCN1A after dosing with small compounds will be loaded with a dye specific for Na+. As a positive control for Na+ concentration changes inside the cells, monensin and gramicidin which are Na+ ionophores, will be used.

Materials and Methods.

Cells will be grown on a cover slide or in a 96 well plate and dosed with varying concentrations of small compounds. After 48 h, the cells will be washed with Locke's buffer (8.6 mM HEPES, 5.6 mM KCl, 154 mM NaCl, 5.6 mM glucose, 1.0 mM $MgCl_2$, 2.3 mM $CaCl_2$, 0.0001 mM glycine, pH 7.4). The fluorescence background will be measure prior to loading the dye inside the cells. The dye will be loaded by incubating the cells with the dye for 1 h at 37° C. with 10 μM SBFI-AM (dye binding to Na+), 0.04% pluronic acid F-127 and 2.5 mM probenecid in Locke's buffer (50 μl/well). At this time, cells will be washed twice with 2.5 mM probenecid in Locke's buffer (150 μl/well). The cells in the 96 well plate or on a coverslide will be placed under a epi-fluorescent microscope equipped with Hg lamp and appropriate filters for excitation and emission (from Omega Optical Inc, Brattleboro, Vt., USA cat # set X-F04-2 or from Chroma Technology Corp, Bellows Falls, Vt., USA, cat #79001). The cells loaded with the dye will be excited at 340 nm and 380 nm; the emission signal will be recorded at 505 nm. After measuring the signal base line, monensin (EMD, Gibbstown, N.J., USA, cat #475895) or gramicidin (EMD, Gibbstown, N.J., USA, cat #368020-25MG) will be added to individual wells with cells as positive control. In order to establish relative up-regulation of active SCN1A at the plasma membrane the cells pre-treated with the active compounds will be compared to vehicle controls. The data will be collected by a camera connected to the epi-fluorescente microscope and quantified using the appropriate software. The raw signals will be processed by calculating the ratio of the 505 nm emissions to 340 nm/380 nm using Excel software.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of treating a patient having Dravet Syndrome comprising:

contacting said patient with at least one compound selected from the group consisting of milnacipran, torsemide, pinacidil, benidipine, ketoconazole, ebselen, tadalafil, zeranol, nefazadone, lomerizine, icariin, omeprazole, esomeprazole, 2-[5-[3-(4-Methylsulfonylamino)benzyl-1,2,4-oxadiazol-5-yl]-1H-indol-3-yl] ethanamine, nitrendipine, amlexanox, mosapride, or stanozolol or pharmaceutically acceptable salts, isomers, enantiomers, isoforms, polymorphs, hydrates, solvates thereof wherein said treatment results in the upregulation of the expression of a sodium channel, voltage-gated, alpha subunit (SCN1A) polynucleotide and treats said patient having Dravet Syndrome.

2. A method of treating a patient having generalized epilepsy with febrile seizure plus (GEFS+) with a therapeutically effective dose of at least one compound selected from the group consisting of milnacipran, torsemide, pinacidil, benidipine, ketoconazole, ebselen, tadalafil, zeranol, nefazadone, lomerizine, icariin, omeprazole, esomeprazole, 2-[5-[3-(4-Methylsulfonylamino)benzyl-1,2,4-oxadiazol-5-yl]-1H-indol-3-yl]ethanamine, nitrendipine, amlexanox, mosapride, or stanozolol or pharmaceutically acceptable salts, isomers, enantiomers, isoforms, polymorphs, hydrates or solvates thereof that upregulates the expression of a sodium channel, voltage-gated, alpha subunit (SCN 1A), and wherein the administration of said compound relieves or causes regression of said disease.

* * * * *